US012778963B2

(12) United States Patent
Liu et al.

(10) Patent No.: US 12,778,963 B2
(45) Date of Patent: Nov. 3, 2026

(54) METHOD AND PHARMACEUTICAL COMPOSITION FOR TREATING OR ALLEVIATING GLIOMAS IN A SUBJECT

(71) Applicant: Zhejiang University, Hangzhou (CN)

(72) Inventors: Chong Liu, Hangzhou (CN); Pengxiang Chen, Hangzhou (CN); Wei Wang, Hangzhou (CN); Anhao Tian, Hangzhou (CN); Changjin Xing, Hangzhou (CN); Rui Liu, Hangzhou (CN)

(73) Assignee: Zhejiang University, Hangzhou (CN)

( * ) Notice: Subject to any disclaimer, the term of this patent is extended or adjusted under 35 U.S.C. 154(b) by 670 days.

(21) Appl. No.: 18/144,990

(22) Filed: May 9, 2023

(65) Prior Publication Data

US 2024/0374610 A1 Nov. 14, 2024

(51) Int. Cl.

| | |
|---|---|
| ***A61K 31/5513*** | (2006.01) |
| ***A61K 31/138*** | (2006.01) |
| ***A61K 31/7072*** | (2006.01) |
| ***A61P 35/00*** | (2006.01) |

(52) U.S. Cl.
CPC ........ *A61K 31/5513* (2013.01); *A61K 31/138* (2013.01); *A61K 31/7072* (2013.01); *A61P 35/00* (2018.01)

(58) Field of Classification Search
CPC .................................................. A61K 31/5513
See application file for complete search history.

(56) References Cited

PUBLICATIONS

Tian, Anhao, et al. "Oncogenic state and cell identity combinatorially dictate the susceptibility of cells within glioma development hierarchy to IGF1R targeting." Advanced Science 7.21 (2020): 2001724. (Year: 2020).*
Olfactory Sensory Experience Regulates Gliomagenesis via Neuronal IGF1; Pengxlang Chen, et al. May 11, 2022; 24 Pgs.; https://doi.org/10.1038/s41586-022-04719-9.

* cited by examiner

*Primary Examiner* — Andrew D Kosar
*Assistant Examiner* — Connor K English
(74) *Attorney, Agent, or Firm* — Cooper Legal Group, LLC

(57) ABSTRACT

A method for treating or alleviating gliomas in a subject is provided, including inhibiting olfactory inputs in the subject. A pharmaceutical composition applicable for treating or alleviating gliomas in a subject is further provided, including at least one inhibitor of an olfactory neuronal circuit in a brain of the subject.

8 Claims, 44 Drawing Sheets
(42 of 44 Drawing Sheet(s) Filed in Color)
Specification includes a Sequence Listing.

g

METHOD AND PHARMACEUTICAL COMPOSITION FOR TREATING OR ALLEVIATING GLIOMAS IN A SUBJECT

TECHNICAL FIELD

The present application relates to a field of cancer treatment, and in particular, relates to a method for treating or alleviating gliomas in a subject and a pharmaceutical composition applicable for treating or alleviating gliomas in a subject.

REFERENCE TO AN ELECTRONIC SEQUENCE LISTING

The contents of the electronic sequence listing (SequenceListing.xml; Size: 28,059 bytes; and Date of Creation: Aug. 31, 2023) is herein incorporated by reference.

BACKGROUND ART

As the most common type of cancer in the central nervous system (CNS), high-grade gliomas (HGGs), particularly glioblastoma, are currently incurable, even with aggressive surgical resection and radiotherapies. The brain is composed of many types of cells that must be precisely orchestrated to maintain the integrity of a normal brain function. In parallel, glioma cells communicate with multiple normal cell types, such as astrocytes, endothelial cells, pericytes, immune cells, and neurons, to form unique microenvironments that are critical for the progression and invasion of tumor cells. Understanding the organization of the tumor microenvironment and its development are highly relevant to the prevention and treatment of HGGs.

The nervous system plays a key role in the pathogenesis of cancer. Initially reported in the peripheral nervous system (PNS), and later in the central nervous system (CNS), distinct types of neuronal cells influence the growth and metastasis of various cancers. In the CNS, glioma cells or brain metastatic cancer cells have been reported to intimately interact with neurons via synapse-like structures to promote the growth of glioma cells, either by paracrine factors such as neuroligin-3 (Nlgn3), or neurotransmitters. Although these studies revealed that neuronal activity plays a critical role in the progression of established tumor cells, it remains largely unclear whether neuronal activity affects the transformation of the cell-of-origin for HGG in their native microenvironments. Furthermore, it is largely unknown whether functional neuronal circuits in the brain under normal physiological conditions contribute to this process.

In brief, there is a need for a means which can be used for effectively treating or at least alleviating a gliomas in a subject in need thereof.

SUMMARY

In view of this, the present application is aimed to provides a means which can be used for effectively treating or at least alleviating a gliomas in a subject in need thereof.

In a first aspect, a method for treating or alleviating gliomas in a subject is provided, including blocking neuron-derived IGF-1 from neurons in the subject, or a receptor thereof. In some embodiments, the neuron is one selected from a group consisting of interneuron and sensory neuron. In some embodiments, the sensory neuron is the olfactory neuron. In some embodiments, the blocking includes inhibiting olfactory signaling in the subject.

In some embodiments, in the method for treating or alleviating gliomas in a subject, inhibiting olfactory signaling in the subject includes one selected from a group consisting of depriving olfactory experience and administering to the subject in need thereof a therapeutically effective amount of an agent which inhibits activities of an olfactory neuronal circuit in a brain of the subject, inhibiting IGF-1 from M/T cells and Gad2 positive neurons, and inhibiting IGF-1 receptor signaling in pre-cancerous mutant oligodendrocyte precursor cells.

In some embodiments, depriving olfactory experience includes naris occlusion.

In some embodiments, the functional neuronal circuits include neuronal circuits responsible for sensory inputs of external environmental stimuli.

In some embodiments, the gliomas is a gliomas in neuronal circuits responsible for sensory inputs of external environmental stimuli.

In some embodiments, the subject is a mammal, for example, human.

In some embodiments, inhibiting activities of an olfactory neuronal circuit includes pharmaceutical and genetical inhibiting the activities of neurons in the olfactory neuronal circuits.

In some embodiments, inhibiting IGF-1 from M/T cells and Gad2 positive neurons includes pharmaceutically and genetically inhibiting the transcription, translation, transportation, modification and secretion of IGF-1 and the IGF-1 in the extracellular space.

In some embodiments, inhibiting IGF-1 receptor signaling in pre-cancerous mutant oligodendrocyte precursor cells includes pharmacologically and genetically inhibiting the IGF-1 receptor, PI3K/AKT/mTOR signaling and Ras/Raf/MEK/MAPK pathways.

In some embodiments, the genetical methods include knocking out genes by CRISPR/Cas9, inhibiting RNAs by shRNA, miRNA, siRNA and ASO and inhibiting proteins by neutralization antibody.

In a second aspect, a pharmaceutical composition applicable for treating or alleviating gliomas in a subject is provided, containing at least one inhibitor of an olfactory neuronal circuit in a brain of the subject.

In some embodiments, the inhibitor of exocytosis is one selected from a group consisting of Eeyarestatin I, Cotransins, CI-976, Dispergo, Apogossypol, FLI-06, AMF-26, Golgicide A, Exo2 and LG186, Exo1, AG1478, LM11, Secramine A, ZCL278, Pitstop-1 and pitstop-2, Dynasore, MiTMAB, 16D10, Compound A5, Vacuolin-1, Retro-1 and Retro-2, Compoun 75 and 134, and UYM201636.

In some embodiments, the inhibitor of IGF-1R signaling is one selected from a group consisting of Linsitinib (OSI-906), Ceritinib, Picropodophyllin, BMS-754807, GSK1838705A, BMS-536924, GSK1904529A, NVP-AEW541 (AEW541), AZD-3463, Ceritinib dihydrochloride (LDK378 dihydrochloride), NVP-TAE 226 (TAE226), AG1024 (Tyrphostin AG 1024), NVP-ADW742 (ADW742), XL228, AZ7550 Mesylate, Ginsenoside Rg5, PQ401, Indirubin Derivative E804, I-OMe-Tyrphostin AG 538 (I-OMe-AG 538), Chromeceptin, is AZ7550 hydrochloride, AZ7550, AZ7550-d5, IGF-1R inhibitor-2, Picropodophyllotoxin-d6, AZ12253801, and PB-020.

In some embodiments, the pharmaceutical composition applicable for treating or alleviating gliomas in a subject further includes a pharmaceutically acceptable carrier.

In some embodiments, the neutralization antibody, such as Figitumumab (CP-751871), Ganitumab (AMG 479), Dalotuzumab (MK-0646), Teprotumumab, Robatumumab (Sch 717454) Xentuzumab, Lonigutamab (hz208F2-4) and Istiratumab (M-6495), neutralize IGF-1, IGF-1R or downstream proteins.

In summary, by using the method and pharmaceutical compositions provided by the present application, a gliomas can be effectively treated or at least alleviated.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
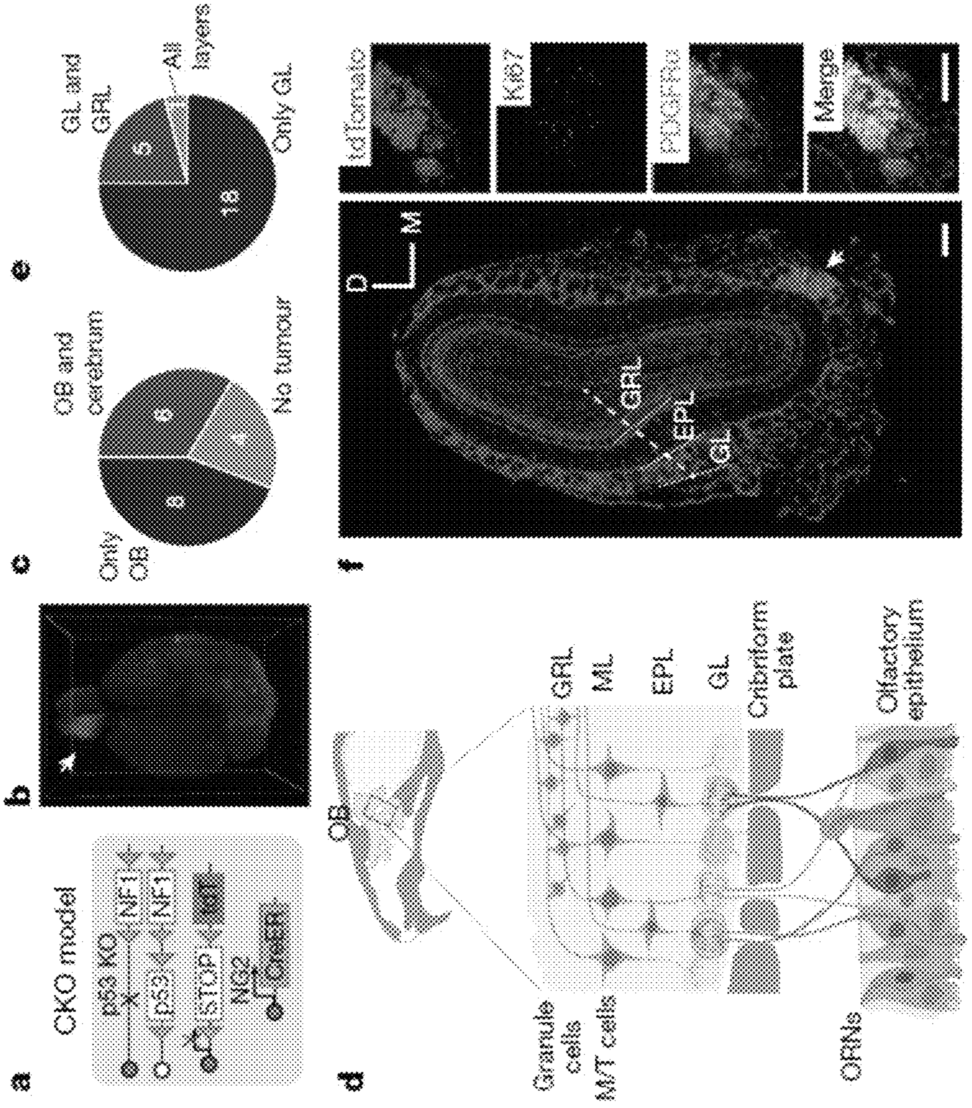
FIG. 1 shows the olfactory bulb as a hot spot of an OPC-derived genetic glioma mouse model: (a) Genotype of the CKO model. Blue triangle: flox site; (b) The representative whole brain of the CKO model cleared by polyethylene glycol (PEG)-associated solvent system (PEGASOS)[40]. The arrow indicates the tumor mass in the OB; (c) Quantification of tumor incidence in the CKO model at postnatal day (P)210. N=18 mice; (d) Schematic diagram of the mouse olfactory system. Olfactory receptor neurons lining the olfactory epithelium extend their axons to the glomerular layer in the OB. Mitral/Tufted cells receive the signal and transmit sensory information to the higher olfactory cortices; (e) Quantification of tumor positions in the OB substructures of the CKO model at P210. N=24 OBs with tumors. Same mouse group as shown in (c); (f) Representative image of a small tumor detected in the GL layer of the CKO model from (e). PDGFRa is used as a cellular marker for tumor OPCs. The arrow indicates a small tumor in the GL. D, dorsal orientation; M, medial orientation. GL, glomerular layer; EPL, external plexiform layer; ML, mitral cell layer; GRL, granule cell layer. Scale bars: (f), 200 µm.

The following description discloses the present application, so that those skilled in the art can realize the present application. The preferred embodiments described below are only examples. It is easy for those skilled in the art to make other obvious transformations. The basic principle of the present application defined in the following description can be applied to other implementation solutions, transformation solutions, improved solutions, equivalent solutions and other technical solutions without deviating from the spirit and scope of the present application.

In the description of the present application, the reference terms "an embodiment", "some embodiments", "example", "specific example" or "some examples" mean that the specific feature, structure, material or characteristic illustrated in this embodiment or example is included in at least one embodiments or examples of the present application. In the specification of the present application, the exemplary expression of the above terms does not have to refer to the same embodiment or example. In addition, the specific features, structures, materials or characteristics can be combined in a suitable manner in any one or more embodiments or examples. Without contradiction, those skilled in the art can combine different embodiments or examples described in this specification with the features in different embodiments or examples.

Animals receive various sensory stimuli, such as odors, sounds, light, and touch, from the surrounding environment on a daily basis. These sensory inputs not only are essential to search for food and avoid predators but also affect their physiological status; and may cause diseases such as cancer. As the most lethal brain tumor, malignant gliomas are known to intimately communicate with neurons at the cellular level. However, it remains unclear whether external sensory stimuli can directly affect the development of malignant gliomas in normal living conditions.

By intensive studies, the present inventor found that, olfaction can directly regulate gliomagenesis. In an autochthonous mouse genetic model recapitulating OPC-originated adult gliomagenesis, gliomas preferentially emerge in the olfactory bulb (OB), the first relay of brain olfactory circuitry. Manipulating the activity of olfactory receptor neurons (ORNs) affects glioma development. Mechanistically, olfaction excites Mitral/Tufted (M/T) cells, which receive sensory information from ORNs and release insulin-like growth factor-1 (IGF-1) in an activity-dependent manner. Specific knockout of Igf1 in M/T cells suppresses gliomagenesis. In addition, blocking the influx of IGF-1 signaling by knocking out the IGF-1 receptor in pre-cancerous mutant OPCs fully diminishes ORN activity-dependent mitogenic effects. A unique link between the sensory experience and gliomagenesis through their corresponding sensory neuronal circuit is established. The present application is made based on the above findings.

The OB is a glioma hot spot

Figure 3:
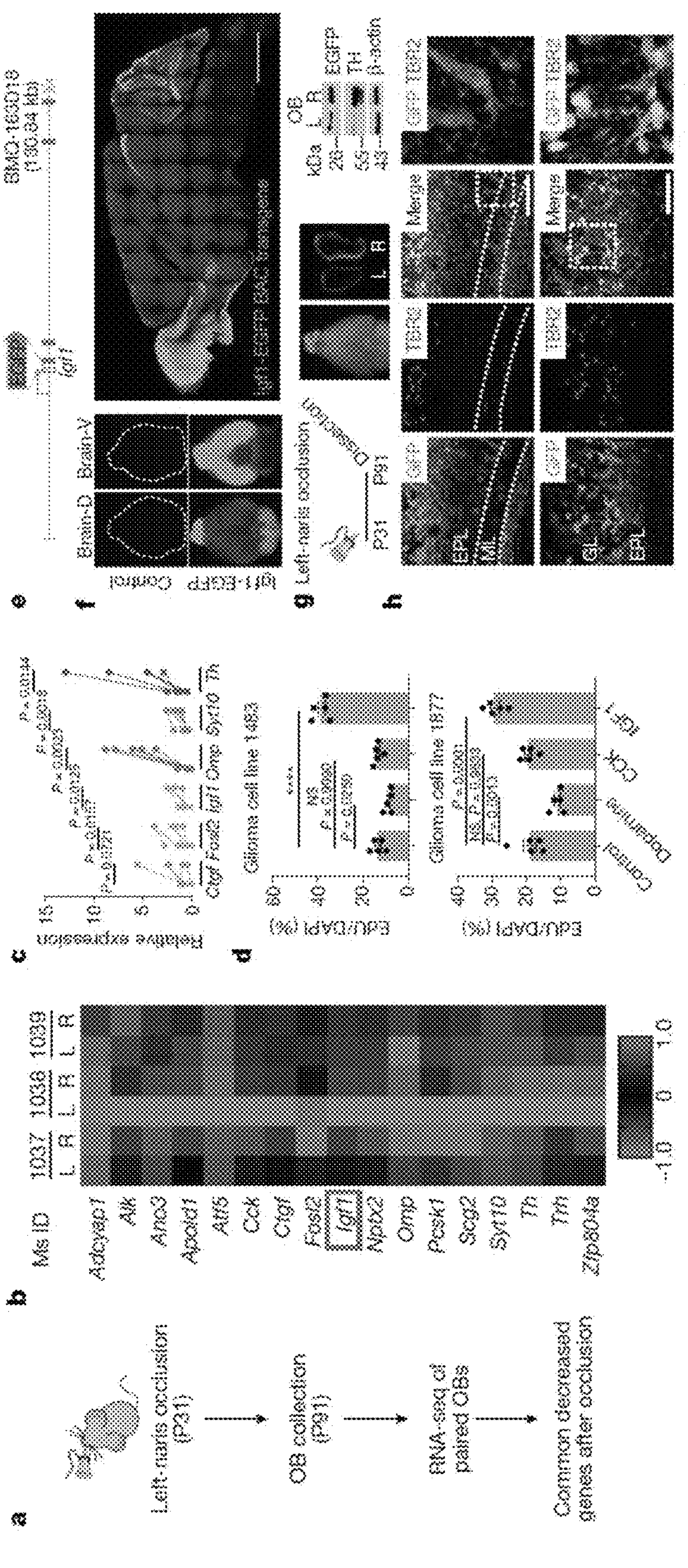
FIG. 3 shows IGF-1 expressed in the mouse olfactory system: (a) Working scheme to screen naris-occlusion gene expression controlled in the OB; (b) Heatmap of the RNA-sequencing results from the 17 genes that exhibited consistent down regulation in the left OB upon left-naris occlusion compared to paired non-occluded right OB. N=3 mice; (c) RT-qPCR validation of the expression of genes from (b) as indicated. N=5 pair of OBs. P values: 0.0721, 0.0157, 0.0134, 0.0125, 0.0023, 0.0018 and 0.0144 respectively. For primers, see Supplementary Table 1; (d) Proliferation rates of two independent CKO model-derived glioma cell lines treated with 100 µM dopamine, 1 nM CCK or 20 ng/mL IGF-1. N=5 biological independent wells for each group. P=0.0250, 0.9990 and <0.0001 respectively for glioma cell line 1483. P=0.0013, 0.9833 and 0.0001 respectively for glioma cell line 1877; (e) Configuration of the Igf1-EGFP BAC transgene; (f) Whole mount and sagittally-sectioned brain tissue of the Igf1-EGFP BAC transgene. N=3 mice are examined; (g) Experimental scheme, immunofluorescence staining, and Western blots of Igf1-EGFP mice with left naris occlusion. For gel source data, see Supplementary FIG. 1; (h) $GFP^+$ cells colocalized with TBR2 in the GL and ML of the Igf1-EGFP BAC transgene. ML is demarcated by dashed lines. GL, glomerular layer; EPL, external plexiform layer; ML, mitral cell layer. Scale bars: (f), 2000 µm; (g), 100 µm. One-sided paired t-test in (c). One-way ANOVA with Dunnett's multiple comparison post-hoc test in (d). ns, no significant, *p<0.05, p<0.01, *p<0.001, ****p<0.0001. Data are presented as mean±SEM.
Figure 5:
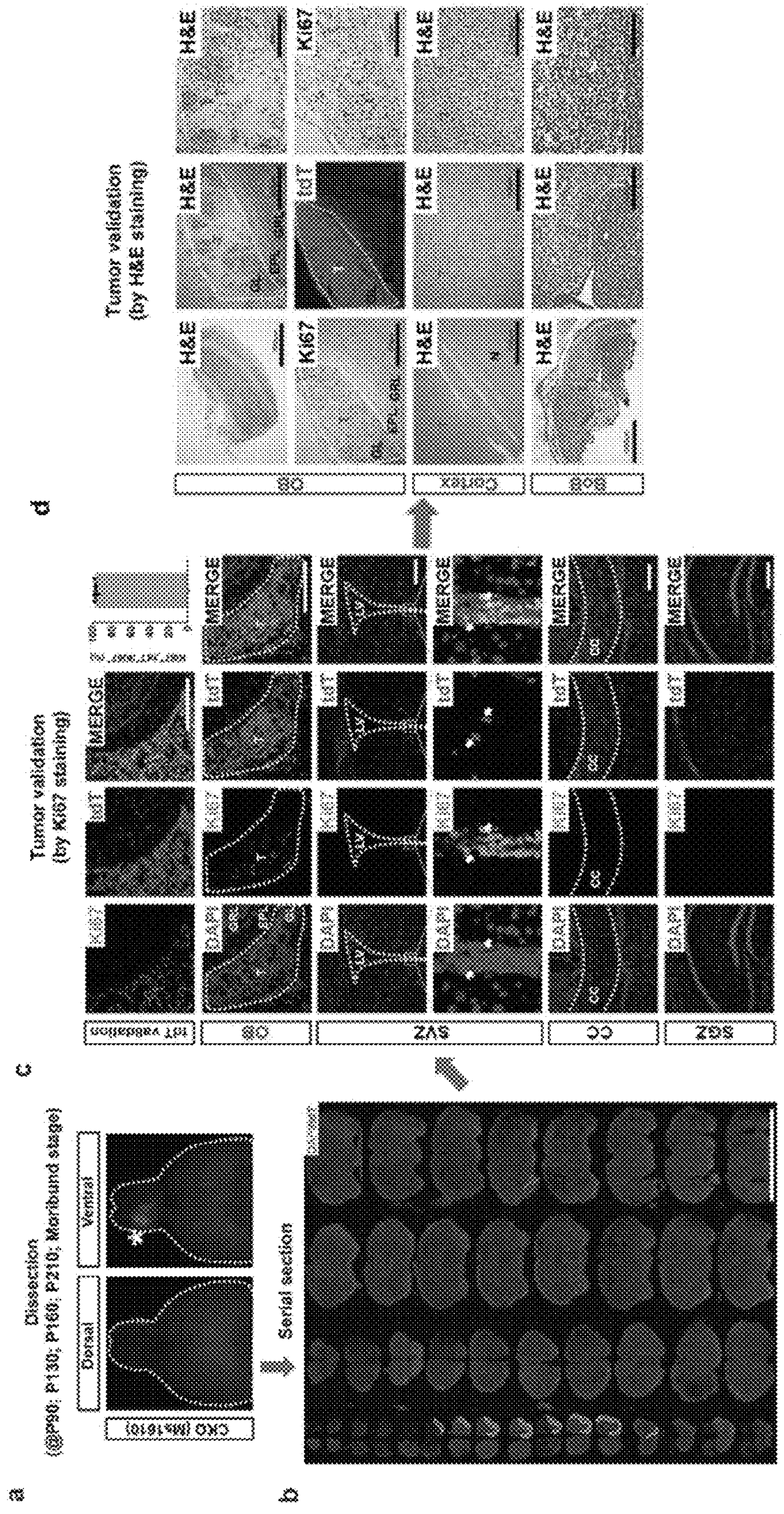
FIG. 5 shows the methodology of tumor mapping: (a) Mice are dissected at specific timepoint to analyze tumor position and tumor volume. Representative images of whole brain after dissection are shown. The brain boundary is demarcated by the dashed line. The asterisk indicates the tumor region in the OB; (b) Each brain is serially sectioned. For tumor position analyzation, every 14 slices are analyzed. For OB tumor volume quantification in FIG. 2, 4, every 4 slices are analyzed. Tumor area is demarcated by the dashed line; (c) Tumors are confirmed by co-localization of tdT and Ki67 staining. tdT-labeling efficiency of tumor cells is confirmed by quantification of $tdT^+$ cell percentage in $Ki67^+$ cells. Representative images show the co-localization of tdT and Ki67 staining in the OB rather than other regions such as the subventricular zone (SVZ), the corpus callosum (CC) and the subgranular zone (SGZ) in the hippocampus; (d) Representative hematoxylin-eosin staining (H&E) images of tumors in the OB, cortex and the bottom of the brain (BoB) at different magnifications. Adjacent slices of OB tumors are used for H&E staining, Ki67 and tdT staining to confirm the feasibility of using tdTomato as the surrogate marker to define tumor mass. T, tumor; N, normal; GL, glomerular layer; EPL, external plexiform layer; ML, mitral cell layer; GRL, granule cell layer; LV, lateral ventricle. Scale bars: (b), 10 mm; (c), 300 μm. Data are presented as mean±SEM.

A genetic mouse model to mimic spontaneous gliomagenesis in adults with OPCs as the cell-of-origin was established. In this model (termed CKO hereafter), tumor suppressor genes Trp53 and NF1 were conditionally knocked out in adult OPCs using the tamoxifen-inducible NG2-$Cre^{ERT}$ transgene. Tumor-lineage cells were visualized by Cre recombinase-dependent lineage-tracing reporter $Rosa26^{LSL\text{-}tdTomato}$ (FIG. 1*a*), which was confirmed as a reliable marker to define tumor mass (FIG. 5). By systematically analyzing tumor locations in a cohort of CKO mice at the tumor stage using multiple approaches, including consecutive whole brain sectioning with 3D reconstruction and whole brain clearing (FIG. 1*b*, FIG. 5-3, Supplementary Videos 1-8), it was founded that the olfactory bulb (OB), the first relay of olfactory information, appears as the location where tumors are frequently detected. Outside the OB, while less prominent, tumors (usually at more advanced stages) could also be found in the anterior olfactory nucleus (AON), olfactory tubercle (OT), piriform cortex, amygdala, entorhinal cortex (FIG. 6), etc. Many of these anatomical structures are involved in processing olfactory information (FIG. 6*a*).

Figure 6:
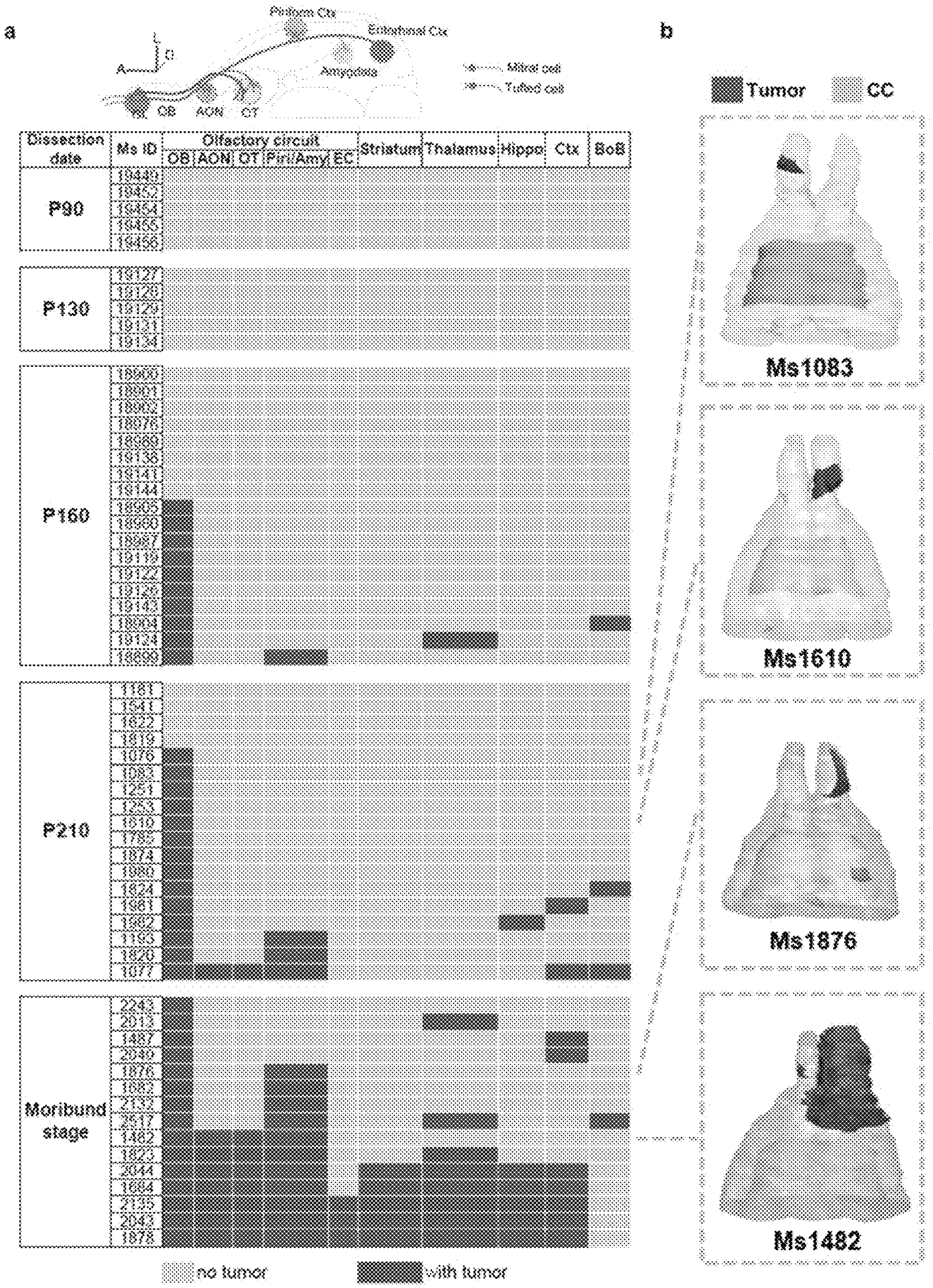
FIG. 6 shows characterization of tumor location in the CKO model by histology: (a) Tumor positions of a cohort of the CKO model at P90 (N=5), P130 (N=5), P160 (N=18), P210 (N=18) and moribund stage (N=15). Each row represents one mouse brain. Red blocks indicate the existence of detectable tumor mass in the corresponding brain region. OB, olfactory bulb; AON, anterior olfactory nucleus; OT, olfactory tubercle; Piri/Amy, piriform and amygdala; EC, entorhinal cortex; Hippo, hippocampus; Ctx, cortex; BoB, bottom of the brain; (b) Representative 3D reconstruction images of the CKO model with tumor. Videos are provided in Supplementary Videos 1-4. Red, tumor area; Cyan, corpus callosum (CC); Grey, brain boundary.

To localize the brain structure(s) where tumors initially developed, a cohort of CKO mice was dissected at defined time points as shown in FIG. 6*a*. It was found that the tumor began to appear around P160 (115 dpi); and further developed to small or medium size in the majority of mice at P210 (165 dpi). Therefore, P210 appears a suitable time point for the early detection of many tumors. Among the mice with detectable tumors, all tumors were associated with the OB (FIG. 1*c*). Furthermore, a single case where the tumor was solely in brain regions outside of the OB (FIG. 1*c*, FIG. 6, 3 and Supplementary Videos 1-8) was not found. No tumors were found around the subventricular zone (SVZ) from the lateral ventricle or the sub-granular zone (SGZ) from the hippocampus of the CKO brain with tumors in the OB (FIG. 6, 3 and Supplementary Videos 1-8), excluding the possibility that the tumors found in the OB initially developed in the SVZ or the SGZ. It was presumed that whole exome sequencing (WES) of multiple tumor sectors from the same brain, where phylogenetic trees suggest that different tumor sectors in the same brain evolved from the same "seed" progenitors, as they shared common clonal mutations (FIG. 7*b*).

Figure 7:
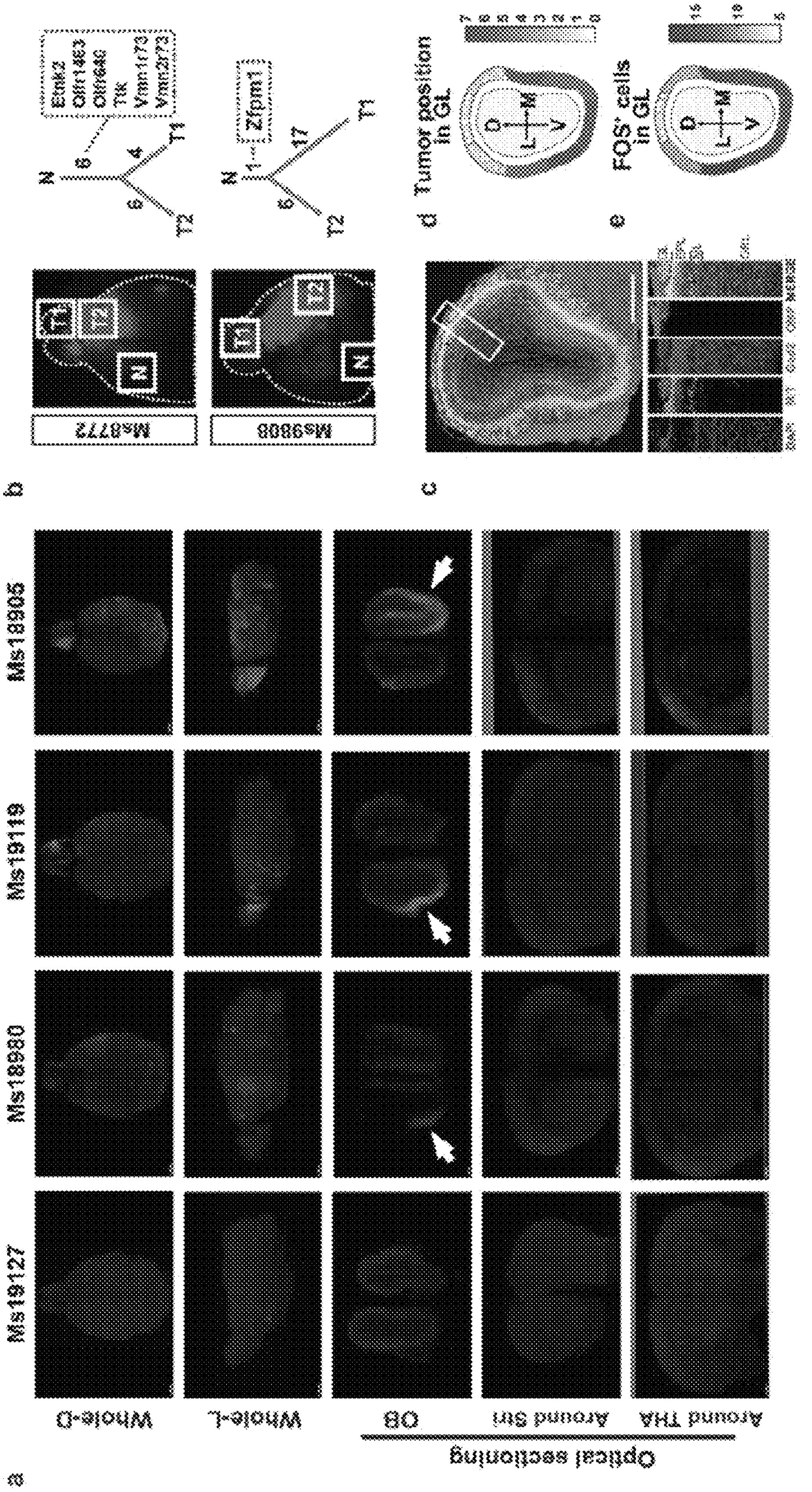
FIG. 7 shows further characterization of tumor distributions by tissue clearing method and whole exome sequencing, as well as the correlation between active olfactory inputs and glioma hot spots in the OB: (a) Cleared brain of the CKO model at different tumor stage. Ms19127 contained no detectable tumor; Ms18980 carried a small tumor in the GL of the OB; Ms19119 harbored obvious tumor in the GL; and Ms18905 carried obvious tumor in the both GL and GRL of the OB. Stri, striatum. THA, thalamus; (b) Whole exome sequencing (WES) and tumor phylogenies for CKO mice at the moribund stage. Three specimens are analyzed in each mouse brain as indicated: N (normal brain tissue), T1 (tumor tissue in the OB) and T2 (tumor tissue in the cerebrum away from the OB). The phylogenic trees illustrate the evolutionary relationship among the three specimens in each brain. For each branch, the number and the gene names of non-synonymous SNVs that are attributed to the branch are shown. Red signal indicates tdT; (c) Representative image of the coronal section from one mouse OB. Different layers within the OB are visualized with corresponding markers as indicated. Of note, M/T cells are labeled by the Igf1-EGFP transgene (see also FIG. 3), the GAD2 expression is visualized by using Gad2-Cre crossing with the reporter line $Rosa26^{LSL\text{-}tdTomato}$ (Ai9). Therefore, the final genotype of this mouse is $Igf1\text{-}EGFP^{+/-}$; $Gad2\text{-}Cre^{+/-}$; $Rosa26^{CAG\text{-}LSL\text{-}TdTomato+/-}$; (d) Quantification of tumor incidence of the CKO model within the GL layer; (e) Normalized density of $cFos^+$ cells in the GL layer. N=3 mice. Scale bar: (c), 500 μm.

The sub-structures in the OB was well characterized in mice, as illustrated in FIG. 1*d*, FIG. 7*c*). Nearly all tumors spanned the glomerular layer (GL), and most tumors were localized only in the GL (FIG. 1*e, f*), suggesting that glomeruli in the OB represent one of the earliest tumorigenic niches in this model. It was found that early tumors appeared more frequently in the ventral compartment of the GL in the OB (FIG. 1*f*, FIG. 7*d*). Intriguingly, in OBs of the mice housed in standard ventilated cages the distribution of c-Fos expression, which generally reflects the active inputs of odors[19], largely overlapped with tumor hot spots (FIG. 7*e*). It was presumed that regional gliomagenesis in the OB might be associated with daily olfactory experiences.

Manipulating ORN activity affects glioma

Figure 8A:
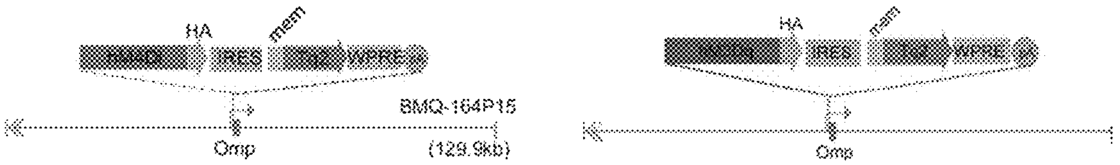
FIG. 8(*a*)-8(*m*) shows characterization of the DREADD transgenes used for chemogenetically manipulating olfaction during gliomagenesis: (a) Configurations of the Omp-hM4Di and the Omp-hM3Dq BAC transgene. "mem", membrane-tagged; (b) Whole sagittal brain sections and high magnification images from the wild type, Omp-hM4Di and Omp-hM3Dq mouse, respectively. N=3 mice for each group are examined; (c-d) Schematic diagram of the buried food test (c) and the time for wild type, Omp-hM4Di and Omp-hM3Dq mice to find the buried food (d). To test the olfaction performance, food is buried at random corner and the time that mice spent to find the food is recorded. The time for mice without clozapine injection to find buried food is recorded on day 3. On day 5, test 2 is performed to record the time for mice with clozapine injection to find the buried food. N=13 mice for WT mice, N=12 mice for the Omp-hM4Di transgene, N=19 mice for the Omp-hM3Dq transgene; (e) Schematic diagram to evaluate odorant-stimulated neuronal activity of Omp-hM4Di and Omp-hM3Dq transgene with clozapine administration. Mice are tested in the cage supplied with fresh air and water underneath to maximally remove baseline odorants from the environment; (f and g) Quantification of $cFos^+$ cell density in the GL (f) and ML (g) from Omp-hM4Di and wild type mice. N=6 mice for the WT, WT clozapine and Omp-hM4Di clozapine group, N=5 mice for the Omp-hM4Di group. P value: 0.2405, <0.0001, <0.0001, 0.2356, 0.0250 and 0.0217 respectively; (h and i) Quantification of $cFos^+$ cell density in the GL (h) and ML (i) from Omp-hM3Dq and wild type mice. N=6 mice for the WT and WT clozapine group, N=5 mice for the Omp-hM3Dq group, N=4 mice for the Omp-hM3Dq clozapine group. P value: 0.3632, 0.0075, 0.0176, 0.4768, 0.0358 and 0.0211 respectively; (j) Treatment scheme of the CKO_Omp-hM4Di model analyzed at the pre-transforming stage; (k) Proliferation rate of mutant OPCs in the OB of CKO and CKO_Omp-hM4Di mice as treated in (j). Relative proliferation rate is calculated by the proliferation rate of mice received clozapine normalized to the average proliferation rate of mice received vehicle. N=8 OBs for CKO with vehicle, N=14 OBs for CKO with clozapine, N=6 OBs for CKO_Omp-hM4Di with vehicle, N=12 OBs for CKO_Omp-hM4Di with clozapine. P=0.0332 and 0.0404 in the left panel and p<0.0001 in the right panel; (1) Treatment schedule of the CKO_Omp-hM3Dq model analyzed at the pre-transforming stage; and (m) Proliferation rate of mutant OPCs in the OB of CKO and CKO_Omp-hM3Dq mice as treated in (1). Relative proliferation rate is calculated by the proliferation rate of mice received clozapine normalized to the average proliferation rate of mice received vehicle. N=6 OBs for CKO with vehicle, N=10 OBs for CKO with clozapine, N=6 OBs for CKO_Omp-hM3Dq with vehicle, N=8 OBs for CKO_Omp-hM3Dq with clozapine. Of note, the same dataset of CKO and the CKO_Omp-hM3Dq model in (m) are also presented in FIG. 4*k* as the control for the CKO_Omp-hM3Dq_IGF1R model. P=0.2820 and 0.0042 in the left panel and p=0.0003 in the right panel; Scale bars: (b), 2 mm, 200 μm. One-sided t-test in (d), (f), (g), (h), (i), (k) and (m). ns, no significance, *p<0.05, p<0.01, *p<0.001, ****p<0.0001. Data are presented as mean±SEM.
Figure 8B:
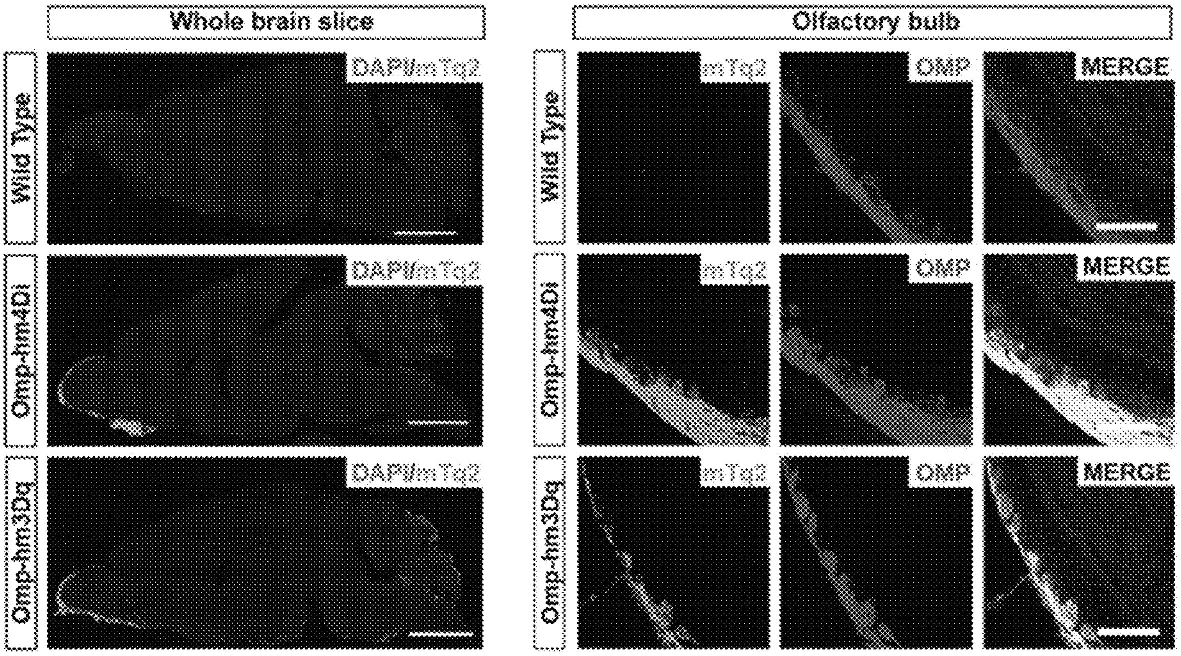
Figure 8C:
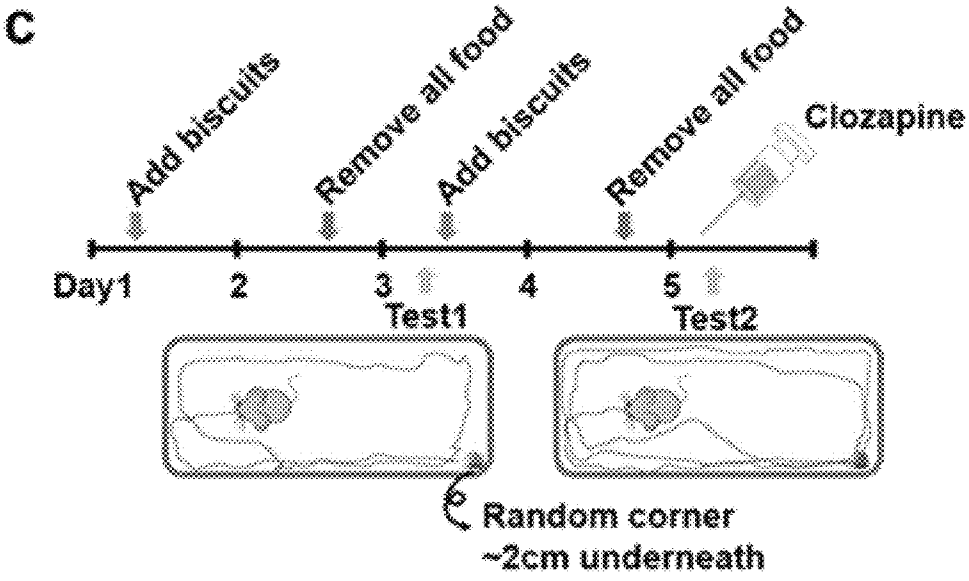
Figure 8D:
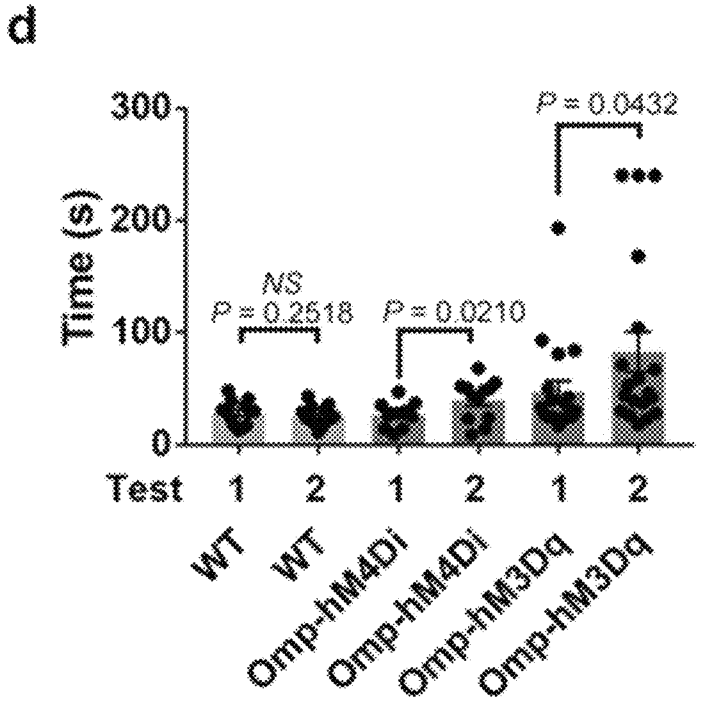
Figure 8E:
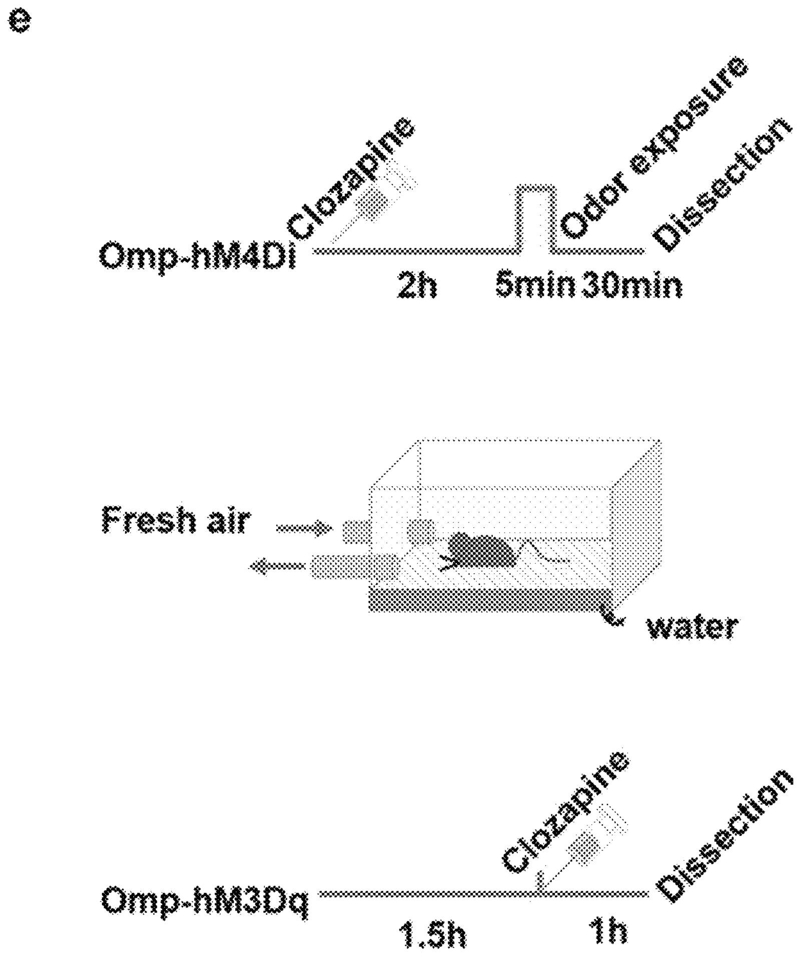
Figure 8F:
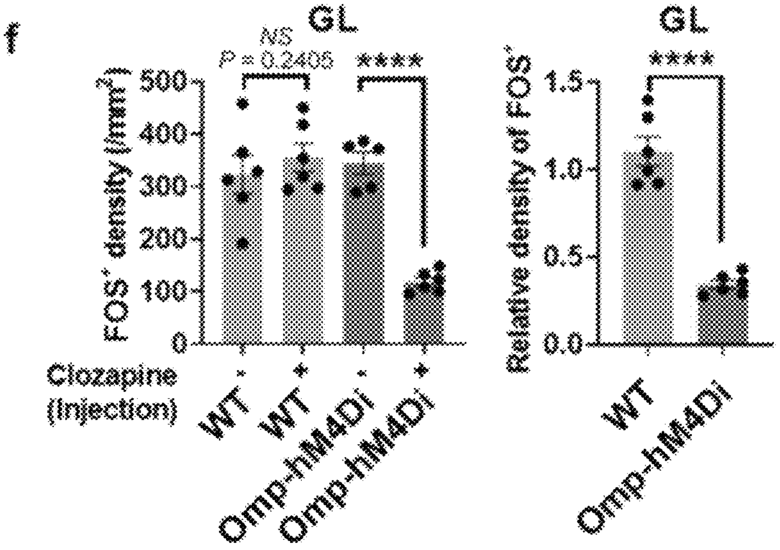
Figure 8G:
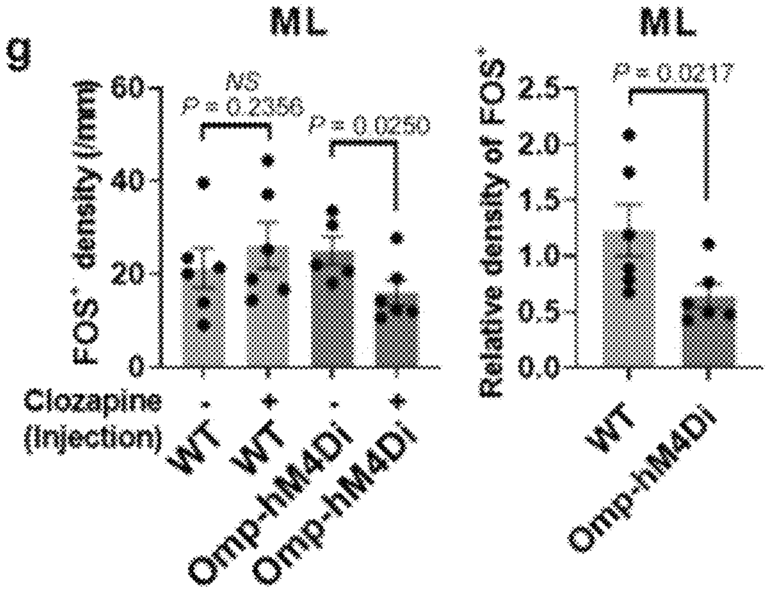
Figure 8H:
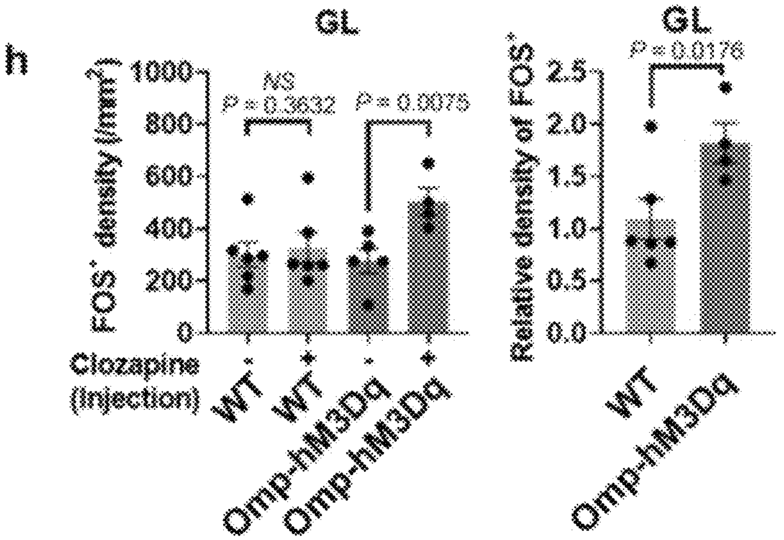
Figure 8I:
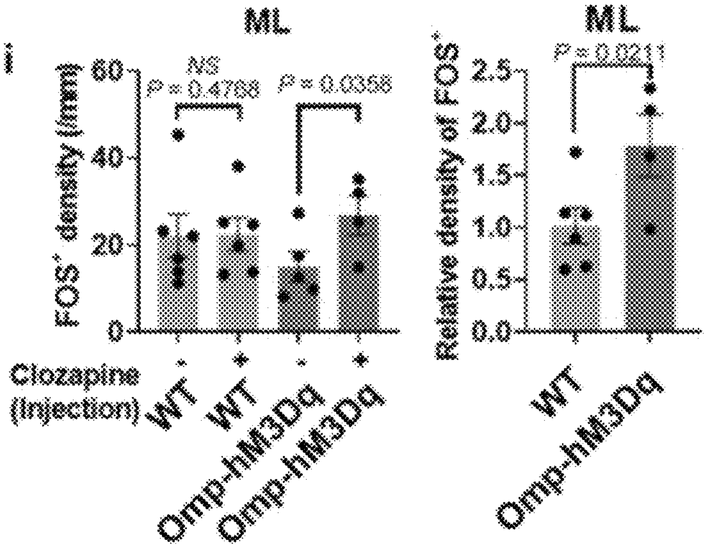

To investigate the causal relationship between olfactory experience and glioma formation, the chemogenetic technology designer receptors exclusively activated by designer drugs (DREADD)[20] was leveraged to specifically and neuronal excitability of ORNs was remotely manipulated. Two bacterial artificial chromosome (BAC) transgenic mouse lines (FIG. 2*a*, FIG. 8*a*) were constructed to express hM4Di or hM3Dq under the promoter of the ORN-specific marker gene Omp[21]. The membrane-tagged cyan fluorescent protein Turquois2 (mTq2) was designed to co-transcribe hM4Di/ hM3Dq to facilitate visualization of hM4Di/hM3Dq expression in the brain. CNO with clozapine was replaced to manipulate DREADDs. The usefulness of these transgenes in reversibly manipulating olfactory inputs in adult mice was proven by the proper expression patterns of the transgene, clozapine-dependent alterations of olfactory behaviors and c-Fos expression levels (FIG. 8b-i).

Figure 2:
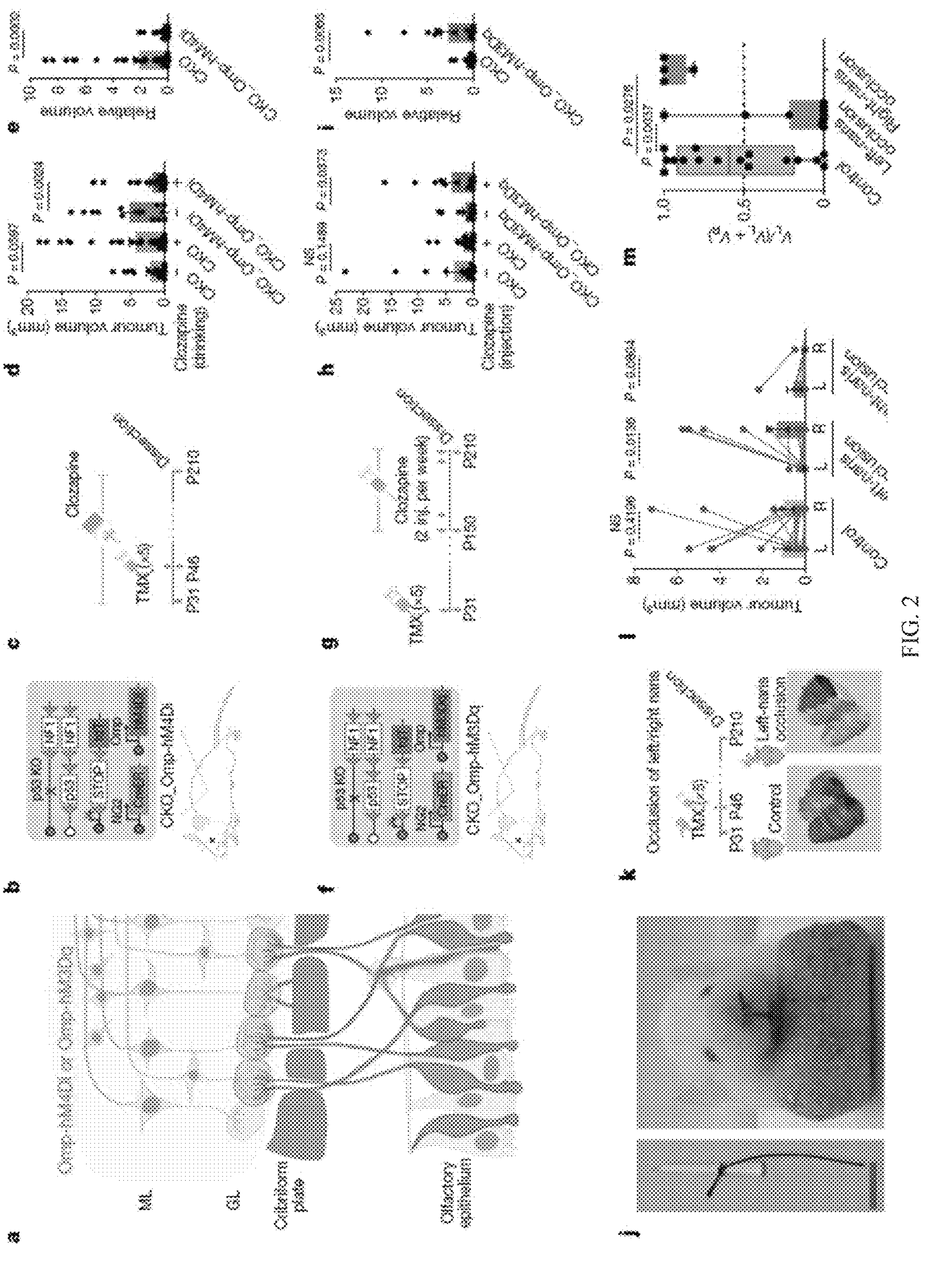
FIG. 2 shows affects of chemogenetic or physical perturbation of the ORN activity on glioma: (a) Schematic diagram of the expression of the Omp-hM4Di/Omp-hM3Dq transgene (marked in green) in the mouse olfactory system; (b-c) The genotype (b) and treatment schedule (c) of the CKO_Omp-hM4Di model; (d-e) Tumor volume (d) and relative volume (e) in the OB of CKO and CKO_Omp-hM4Di mice as treated in (c). Relative volume is calculated by normalizing the tumor volumes of mice which received clozapine to the average tumor volume of mice which received vehicle. N=18, 34, 14 and 36 mice respectively. P=0.0276 and 0.0148 in (d) and p=0.0005 in (e); (f-g) The genotype (f) and treatment schedule (g) of the CKO_Omp-hM3Dq model; (h-i) Tumor volume (h) and relative volume (i) in the OB of CKO and CKO_Omp-hM3Dq mice. Relative volumes are calculated by normalizing the tumor volumes of mice which received clozapine to the average tumor volume of mice which received vehicle. N=18, 18, 18 and 15 mice respectively. P=0.1511 and 0.0492 in (h) and p=0.0145 in (i); (j) Representative images of the silica gel plug tied with a black surgical suture to indicate the presence of the plug during the experiment and a mouse with L-naris occlusion; (k) Scheme of the naris occlusion experiment for analysis at the tumor stage and 3D reconstruction of the entire OB from representative control and L-naris occluded CKO mice analyzed at P210. The contour of the OB is marked in light gray, while the tumor masses are marked in red; (1 and m) Quantification of tumor volume (1) and symmetry of tumors between paired OBs (m) in CKO mice without naris occlusion (controls) and those with the left or right naris occluded. The OB tissue is consecutively sectioned and analyzed as described in FIG. 5. VL, tumor volume in left OB; VR, tumor volume in right OB. N=18, 17 and 6 mice relatively in (1). Data in (1) and (m) are from the same dataset. Of note, 2 mice in the control group, 6 mice in the L-naris occlusion group and 2 mice in the R-naris occlusion group without detectable tumors are not eligible for calculation of the value of tumor symmetry, and are therefore not included in (m). P value in (1): control, 0.4196; L-naris occlusion, 0.0136; R-naris occlusion, 0.0804. P value in (m): control vs L-naris occlusion, 0.0037; control vs R-naris occlusion, 0.0007. L, left; R, right. One-sided t-test in (d), (e), (h), (i) and (m). One-sided paired t-test in (1). ns, no significant, *p<0.05, p<0.01, *p<0.001. Data are presented as mean±SEM. The box plot marks the median, upper and lower quartiles and whiskers are presented min to max in (m).
Figure 8J:
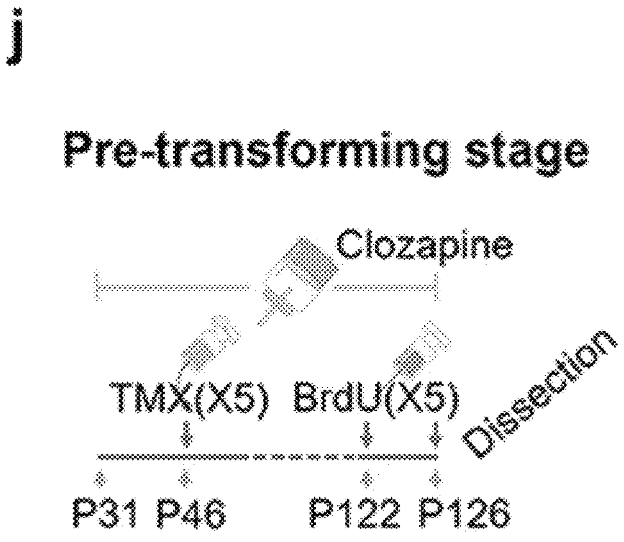
Figure 8K:
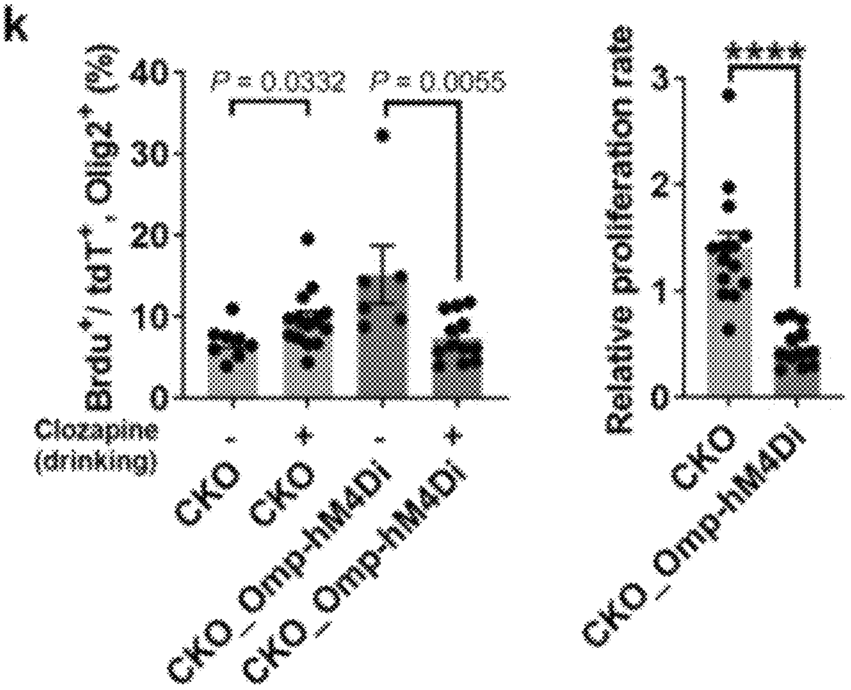

Next, the Omp-hM4Di transgene was bred into the CKO model (FIG. 2b) to remotely suppress olfactory inputs throughout gliomagenesis by systemic administration of clozapine via drinking water (FIG. 2c). It was found that long-term administration of clozapine significantly decreased the tumor volume in CKO_Omp-hM4Di mice (column 4 vs. column 3 in FIG. 2d). Also, the tumor volumes in the CKO littermates with/without clozapine administration were quantified. Notably, when compared to the CKO group without clozapine treatment, treatment with clozapine alone promoted tumor growth (compare column 2 with column 1 in FIG. 2d). However, after adjusting for their own non-clozapine controls, a more striking reduction in tumor volume was observed in the CKO_Omp-hM4Di model (FIG. 2e). Consistent with the results at the tumor stage, it was found that the proliferation rate of pre-transforming mutant OPCs in the GL also decreased in the clozapine-treated CKO_Omp-hM4Di model (FIG. 8j, k). These multiple lines of evidence suggest that suppression of olfactory inputs impairs the initiation and/or early progression of gliomas in the OB, likely by inhibiting the proliferation of pre-transforming and/or transformed OPCs.

Figure 8L:
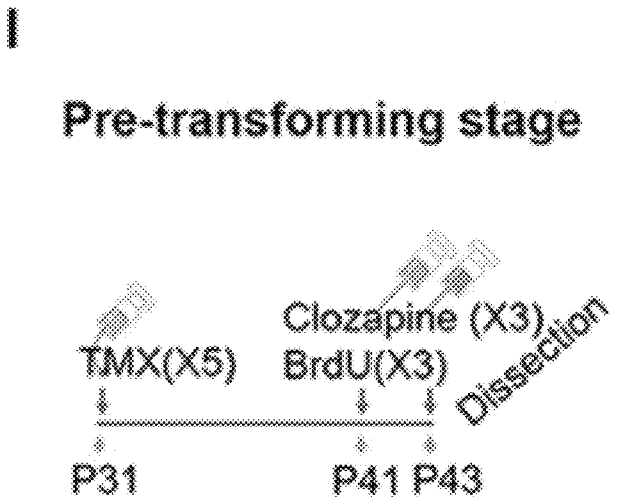
Figure 8M:
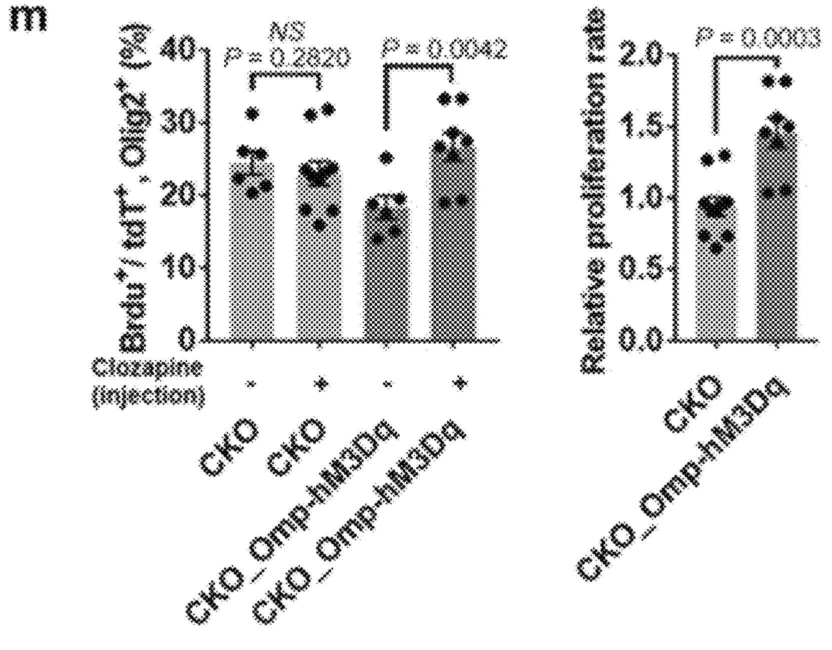

Similar to Omp-hM4Di, the Omp-hM3Dq transgene was bred into the CKO model (FIG. 2f), and it was found that the proliferation rate of mutant OPCs in the GL of the CKO_Omp-hM3Dq model at the pre-transforming stage exhibited a clozapine-dependent increase after normalization to the non-clozapine control (FIG. 8l, m). This observation suggests that acutely enhancing ORN activity can stimulate cell division of pre-transforming mutant OPCs. Further, to activate ORNs long-term for the study of tumorigenesis, clozapine was administered by periodic intraperitoneal injection (two injections/week, as shown in FIG. 2g). It was found that clozapine treatment increased the tumor volume of CKO_Omp-hM3Dq mice compared to CKO mice (FIG. 2h, i).

Figure 9A:
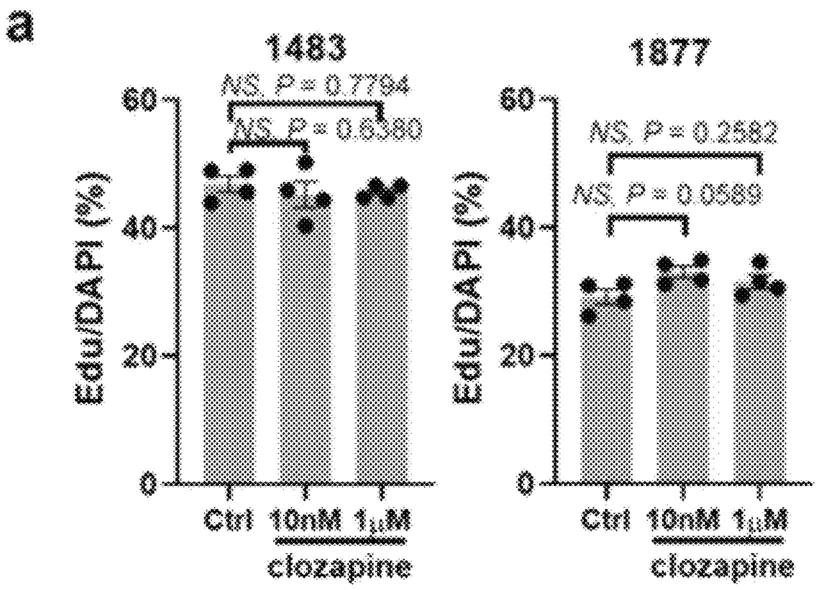
FIG. 9(*a*)-9(*z*) shows the tumor immune microenvironment not affected by clozapine and physical manipulation of ORN activity affects glioma: (a) Proliferation rates of two CKO model-derived glioma cell lines treated with clozapine as indicated. The cells are maintained in complete medium. The proliferation rates of culture cells are measured by EdU incorporation assay. N=4 biologically independent wells for each group. P=0.6380, 0.7794, 0.0589 and 0.2582 respectively; (b-d) Quantification of tumor invasiveness (c) and tumor proliferation (d) in the CKO model under clozapine treatment at the tumor stage. Tumor invasiveness is defined as the distance from the core tumor area (with the highest density in the tumor) to the normal area (where the density of tumor cells declined to the same as that in the region away from the tumor), as the length of white rectangular (b). Five random areas are calculated for each mouse. Tumor proliferation rate is defined as the percentage of $Ki67^+$, $tdT^+$ cells in $tdT^+$ cells. N=5 mice for each group. The tumor mice are from the same group of mice used in the first two columns of FIG. 2*d*. P=0.3764 in (c) and p=0.4086 in (d); (e) Percentage of granulocytes, macrophage, dendritic cells, B lymphocytes and T lymphocytes in the peripheral blood of the WT mice (at the age of 8 weeks) under clozapine treatment. Clozapine injection, clozapine is administrated by i.p. (two injections per week for three weeks). Clozapine drinking, mice are access to clozapine containing water for three weeks. N=4 mice for each group. P=0.0064, 0.0254, 0.0004, 0.0017, 0.5331, 0.8202, 0.7780, 0.9334, 0.5786 and 0.8282 respectively. For FACS gating strategy, see Supplementary FIG. 2; (f) Percentage of granulocytes, macrophage, dendritic cells, B lymphocytes and T lymphocytes in the peripheral blood of the WT, Omp-hM3Dq and Omp-hM4Di transgenic mice (at the age of 8 weeks) under clozapine treatment. The clozapine treatment is the same as that of injection paradigm in (e). Clozapine is administrated by i.p. (two injections per week for three weeks). w/ clozapine, with clozapine. The values are presented as the ratio to the WT mice. N=4 mice for each group. P=0.1461, 0.3505, 0.1350, 0.2264, 0.4287, 0.4795, 0.1852, 0.8691, 0.1351 and 0.4214 respectively; (g) The blood-brain barrier integrity is evaluated by Evans Blue dye. w/o Evans Blue, without Evans Blue treatment. w/ Evans Blue, with Evans Blue treatment. WT mice at the age of 8 weeks are used in this assay. The schemes of clozapine treatment by drinking water or i.p. injection are the same as that in (e). See Methods section for the details. N=4 mice for each group. P=0.8040, 0.3180, 0.8917, 0.0019, 0.5080 0.9998, 0.0024, 0.8397 and 0.8214 respectively; (h) Immunochemistry staining of CD15 in the brain of WT, Omp-hM3Dq, Omp-hM4Di and the CKO tumor mice with clozapine treatment. Spleen is used as the positive control. Red arrows point to $CD15^+$ granulocytes in the spleen. WT mice treated with vehicle is used as negative control. T, tumor area. The brain samples of the WT, Omp-hM3Dq, Omp-hM4Di mice are from the mice analyzed in (f). The brain samples of CKO tumor mice are from the same group of clozapine-treated CKO mice used in FIG. 2*d*; (i) Quantification of $Iba1^+$ cell density in CKO_Omp-hM4Di model at the pre-transforming stage as indicated in FIG. 8*j*. N=6 OBs for CKO, N=6 OBs for CKO with clozapine drinking, N=4 OBs for CKO_Omp-hM4Di, N=6 OBs for CKO_Omp-hM4Di with clozapine drinking. P value: column A vs B, 0.9932; A vs C, 0.3648; A vs D, 0.9984; B vs C, 0.4936; B vs D, 0.9728; C vs D, 0.2964; (j) Quantification of $Iba1^+$ cell density in CKO_Omp-hM3Dq model at the pre-transforming stage as indicated in FIG. 81. N=6 OBs for CKO with vehicle, N=6 OBs for CKO with clozapine, N=4 OBs for CKO_Omp-hM3Dq with vehicle, N=6 OBs for CKO_Omp-hM3Dq with clozapine. P value: column A vs B, 0.7722; A vs C, 0.6589; A vs D, 0.8465; B vs C, 0.2175; B vs D, 0.3158; C vs D, 0.9725; (k and 1) Quantification the density of total macrophage/microglia (marked by $Iba1^+$) (k) and those activated macrophage/microglia ($CD68^+$, $Iba1^+$) (1) in the non-tumor region of the CKO tumor brain. Non-tumor region is defined as the brain region where no obvious tumor lesion is included (usually far away from the tumor core). Clozapine is administrated by drinking water from P30 to P210. Mice are analyzed at P210. N=6 OBs for CKO and N=4 OBs for CKO with clozapine drinking in (k). N=4 OBs for each group in (1). P=0.3000 in (k) and p=0.4869 in (1); (m and n) Quantification the density of $Iba1^+$ macrophage/microglia (m) and $CD68^+$, $Iba1^+$ activated macrophage/microglia (n) in the tumor region of the CKO model. Clozapine is administrated by drinking water from P30 to P210. Mice are analyzed at P210. N=5 tumors for each group in (m). N=4 tumors for each group in (n). P=0.2941 in (m) and p=0.3907 in (n); (o) Representative images of the macrophage/microglia of the CKO model analyzed in (k-n). Low-power and high-power images are both provided. The MERGE channel in low-power images including DAPI, tdT and Iba1 channels. The MERGE channel in high-power images including DAPI, CD68, tdT and Iba1 channels. N, non-tumor region. T, tumor region. Of note, the samples analyzed in (k-o) are from the same group of CKO mice used in FIG. 2*d* (the first two columns); (p) Representative images of mTq2 and tdT expression in glomeruli of CKO_Omp-hM4Di mice administrated with clozapine; (q and r) Quantification of mTq2 (assumed also hM4Di) and tdTomato intensity among glomeruli of CKO_Omp-hM4Di mice with (q) and without (r) clozapine treatment. Each dot represents one glomerulus. Two-sided Pearson correlation coefficients are calculated; (s and t) Immunofluorescence staining (s) and Western blots (t) of tyrosine hydroxylase (TH) in control and left-naris occlusion mice. Mice are plugged at P31 and analyzed after two months. For gel source data, see Supplementary FIG. 1; (u-w) Scheme of the experimental procedure (u) and for single naris occlusion analysis at the pre-transforming stage. Proliferation cell density (v) and proliferation rate of mutant cells (w) are analyzed. N=4 mice for each group. P=0.0198, 0.0835, 0.0401 and 0.0456 respectively; (x-z) Scheme of the experimental procedure (x), representative whole brain images (y) and quantification (z) of L-naris occlusion mice grafted with mouse glioma cell lines. P value: 0.0356. Scale bars: (b), 100 μm; (o), 500 μm and 50 μm; (p), 400 μm; (s), 1000 μm. One-way ANOVA with Dunnett's multiple comparison post-hoc test in (a), (e), (f), (g), (i) and (j). One-sided t-test in (c), (d), (k), (1), (m), (n), (v), (w) and (z). ns, no significant, *p<0.05, p<0.01, *p<0.001, ****p<0.0001. Data are presented as mean±SEM. The box plot marks the median, upper and lower quartiles and whiskers are presented min to max in (v) and (w).
Figure 9B:
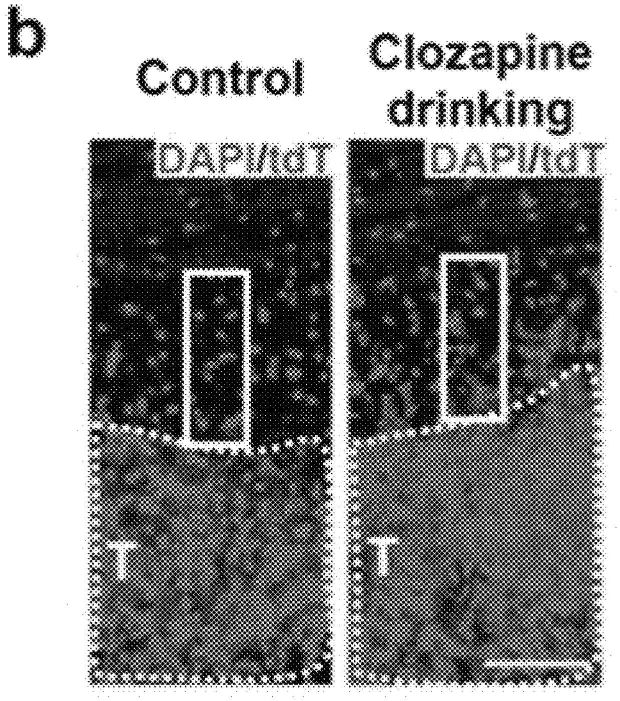
Figure 9C:
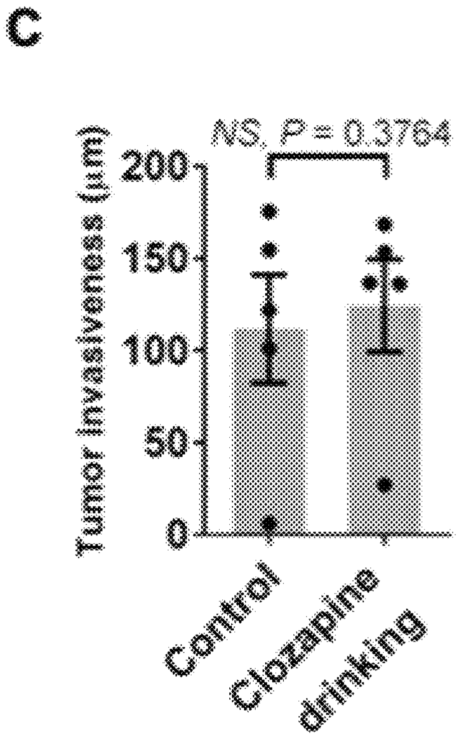
Figure 9D:
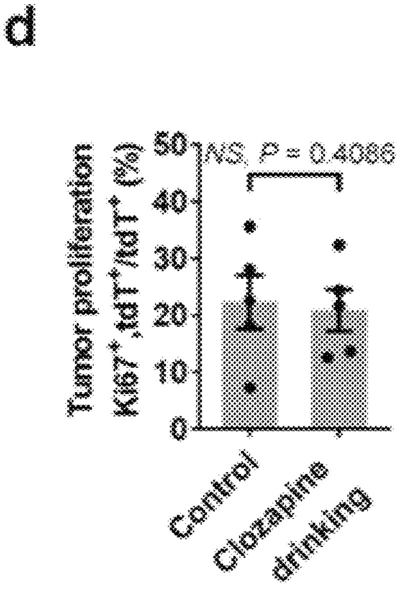
Figure 9E:
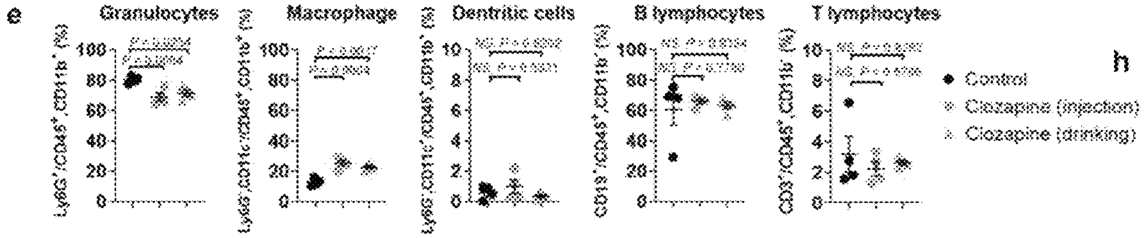
Figure 9F:
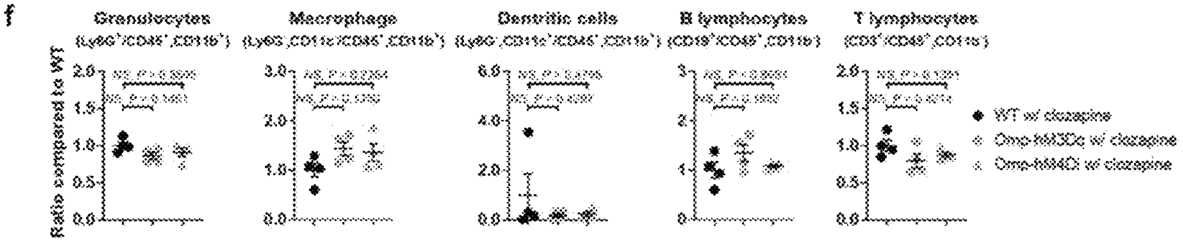
Figure 9G:
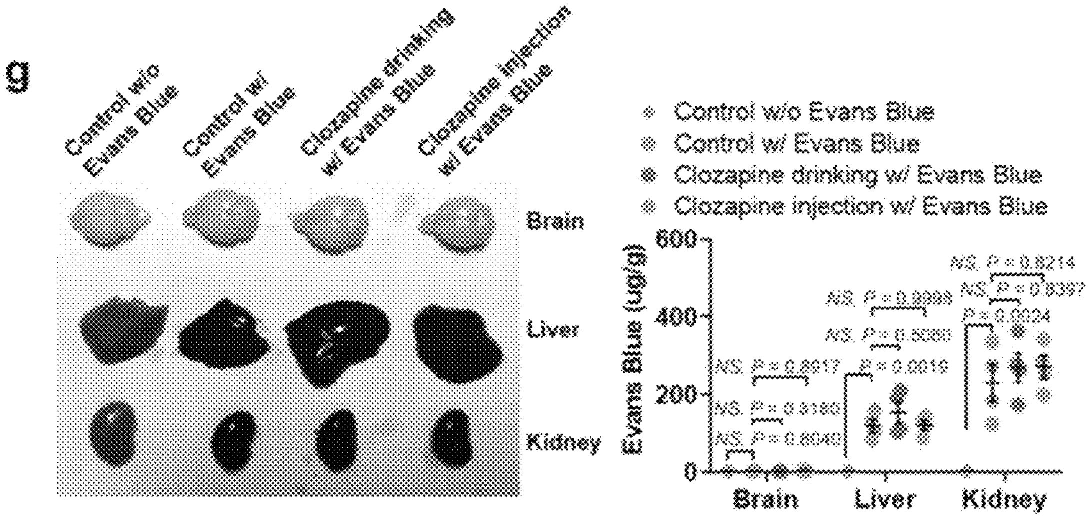
Figure 9H:
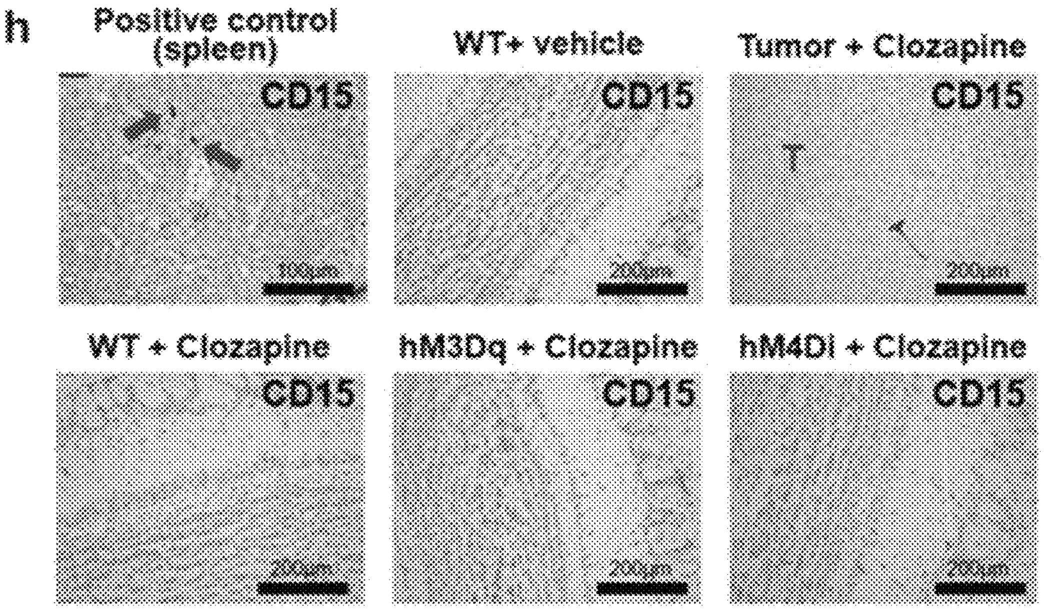
Figure 9I:
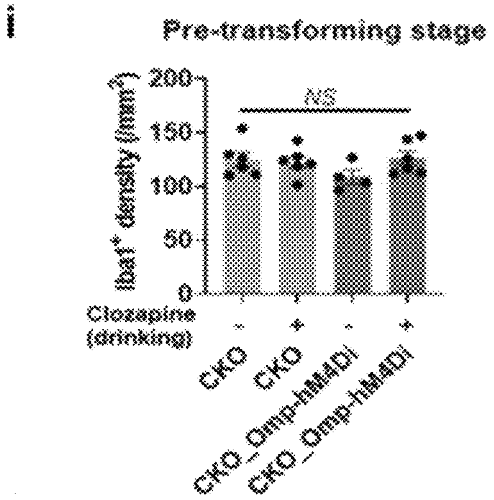
Figure 9J:
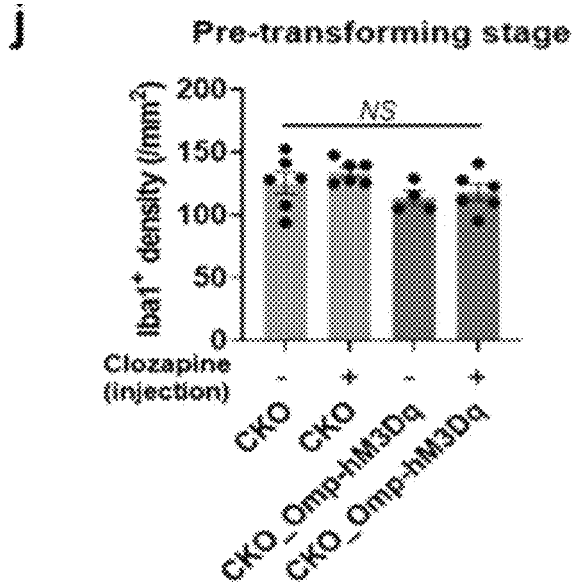
Figure 9K:
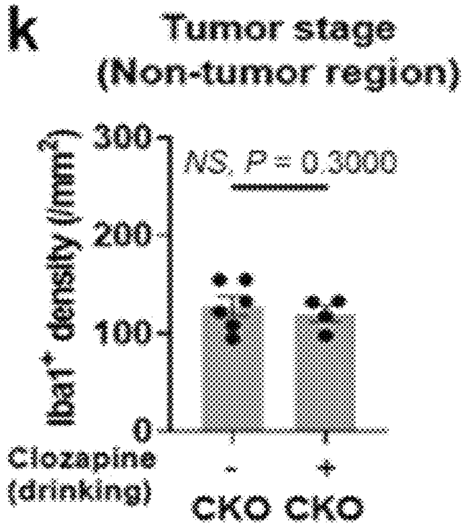
Figure 9L:
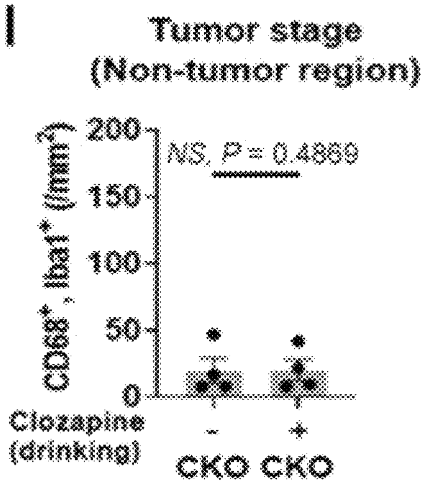
Figure 9M:
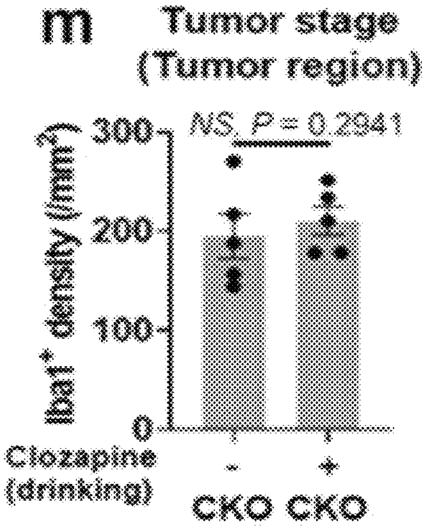
Figure 9N:
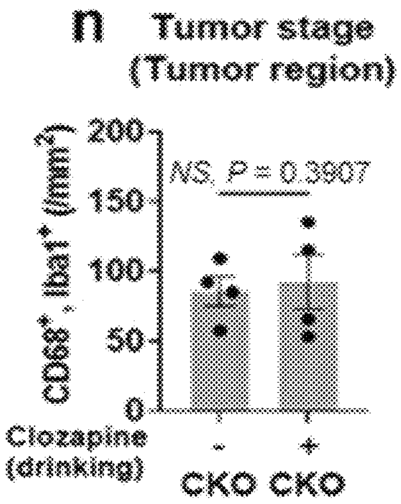
Figure 9O:
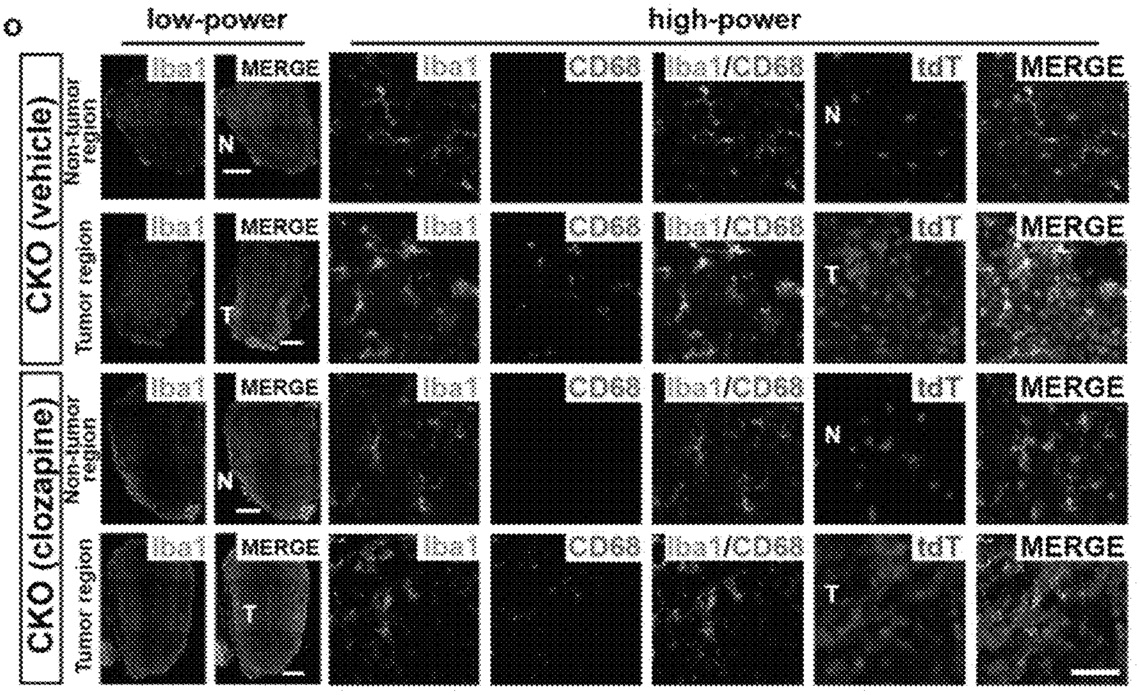

As a result, it was validated that clozapine itself did not affect the proliferation of tumor cells either in vitro or in vivo or their invasion in vivo (FIG. 9a-d). Therefore, the tumor-promoting effect of clozapine observed in the DREDD-CKO model was unlikely due to the direct effect of clozapine on tumor cells. However, it was found that clozapine treatment (either by oral or i.p. administration) slightly but significantly reduced the number of granulocytes and increased the number of macrophages (FIG. 9e, f). Nonetheless, as clozapine did not affect the integrity of the blood-brain-barrier (FIG. 9g), the disturbance of clozapine on the peripheral immune cells unlikely directly affects the brain immune microenvironment. It was further confirmed that barely any granulocytes could be found in the brain parenchyma (FIG. 9h), and that the number or the activation of local resident microglia were not affected by clozapine treatment in the CKO model regardless the tumor stage (FIG. 9i-o). Therefore, clozapine unlikely affects gliomagenesis through immune cells.

Figure 9P:
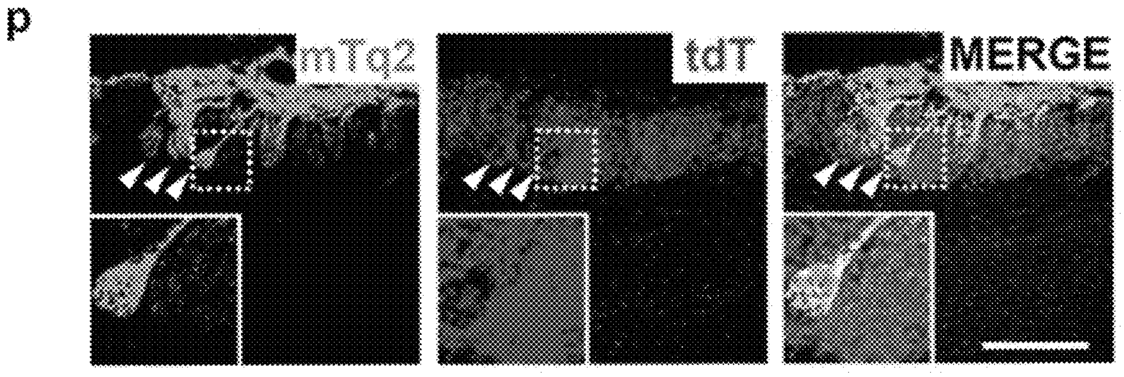
Figure 9Q:
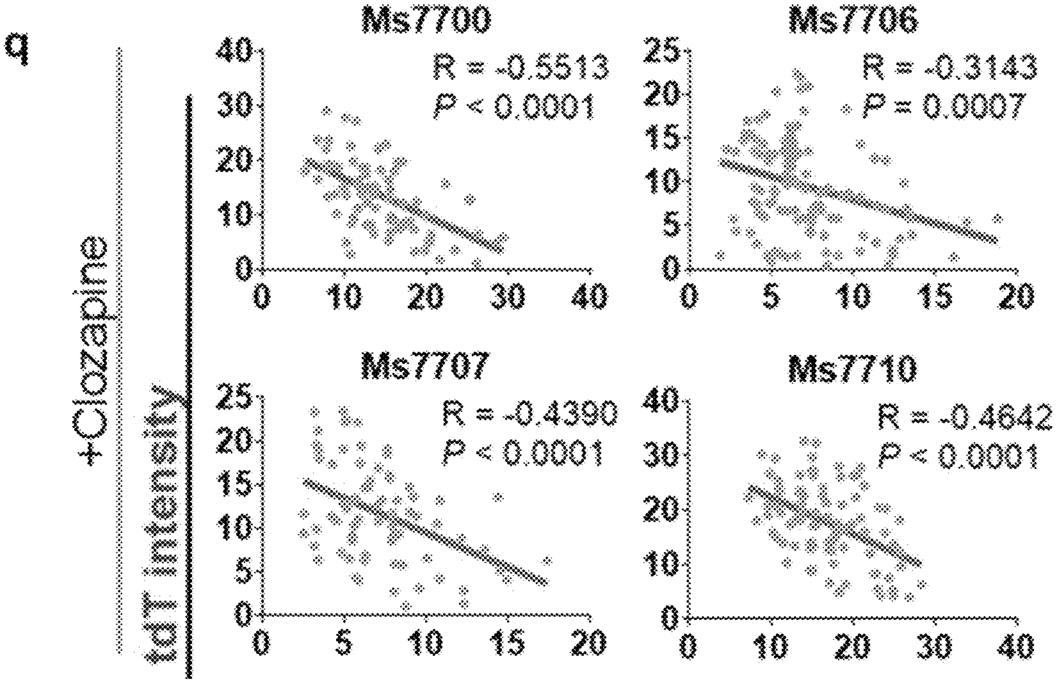
Figure 9R:
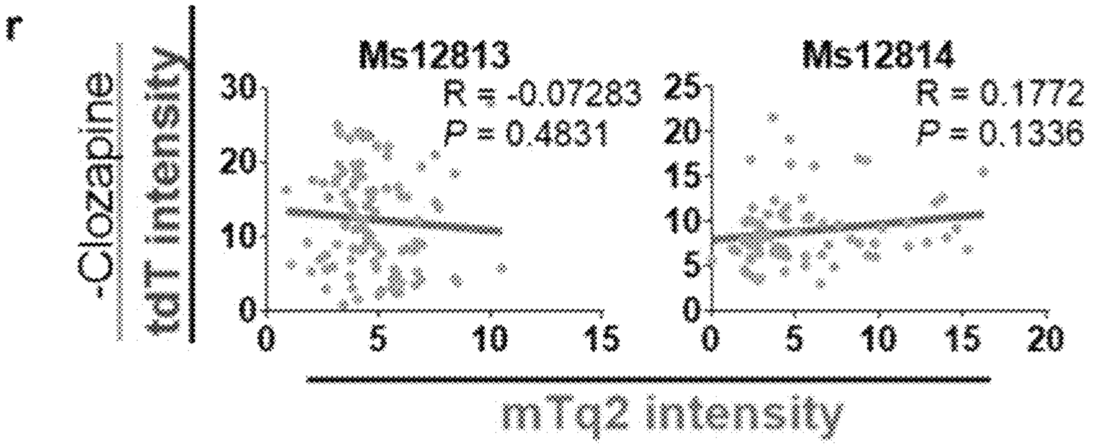

It was further noted that the mTq2 reporter did not express homogenously in all glomeruli within the same OB of the CKO_Omp-hM4Di model (FIG. 9p). Presumably, if hM4Di suppressed tumor cells by silencing ORN activities, the glomeruli with higher mTq2 expression would be a less optimal environment for transformed tumor cells to colonize. Indeed, quantitative analyses revealed a clear inverse correlation of intensities between mTq2 and tdTomato among glomeruli in a clozapine-treated (FIG. 9q), but not in vehicle-treated CKO_Omp-hM4Di model (FIG. 9r).

Naris Occlusion Suppresses Glioma

Figure 9S:
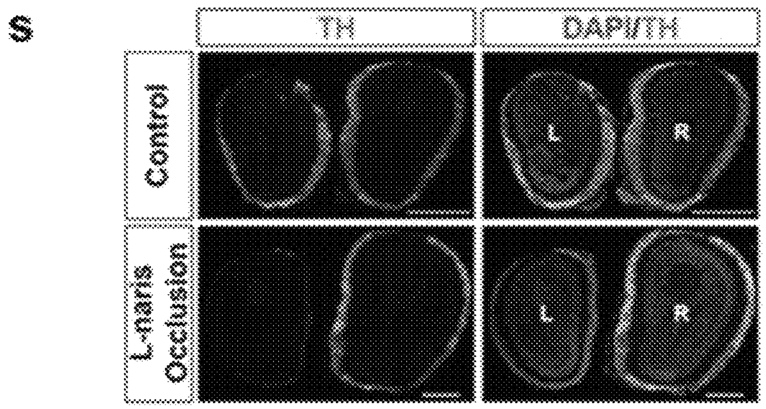
Figure 9T:
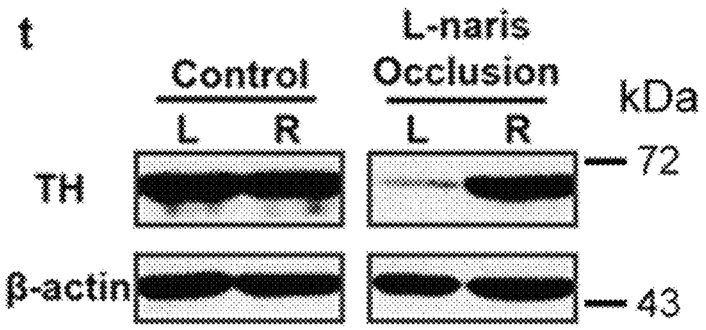

To directly manipulate the function of the olfactory circuit in a more physiologically relevant context, normal olfactory experience was deprived from the CKO model. Olfactory inputs through naris occlusion was suppressed by using small plugs, which was originally developed to study the plasticity of olfactory circuits[19] (FIG. 2j). As rodents solely use their naris for breathing, only one naris was blocked when applicable. The deprivation of olfactory inputs was validated by the decrease of tyrosine hydroxylase (TH) in the GL, whose expression is highly dependent on continuous olfactory inputs[19,24] (FIG. 9s, t).

Figure 9U:
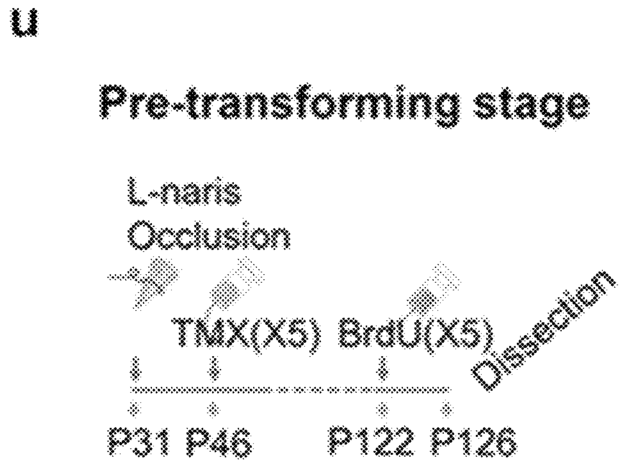
Figure 9V:
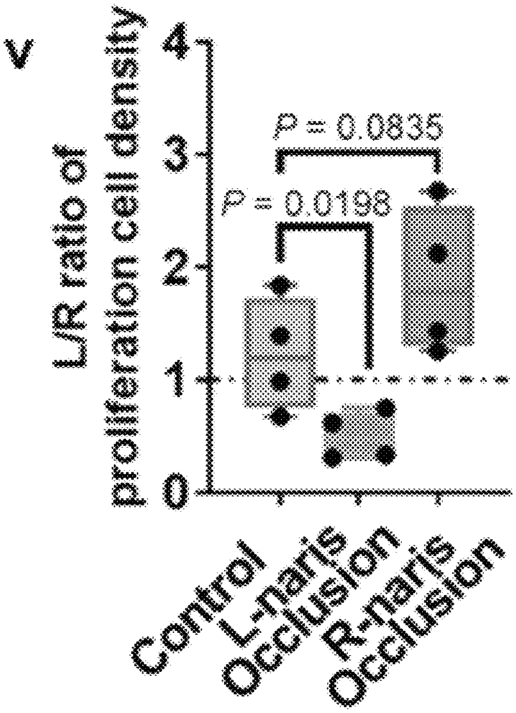
Figure 9W:
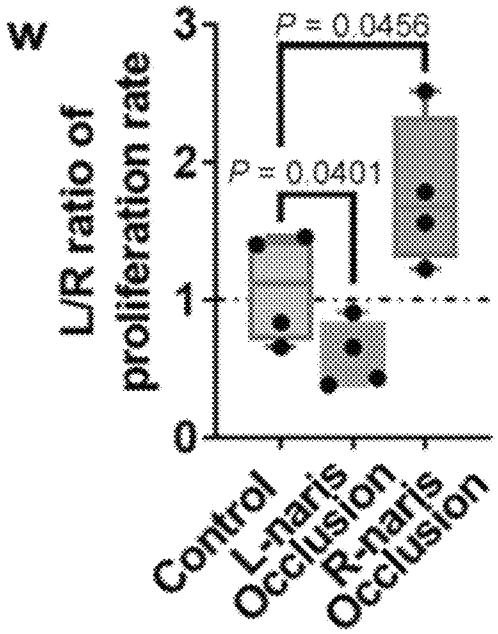
Figure 9X:
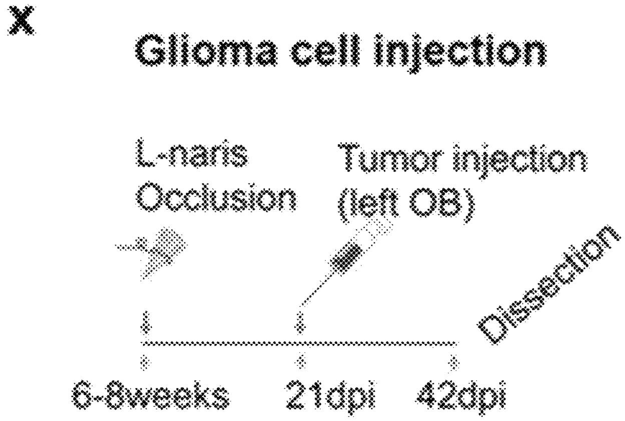
Figure 9Y:
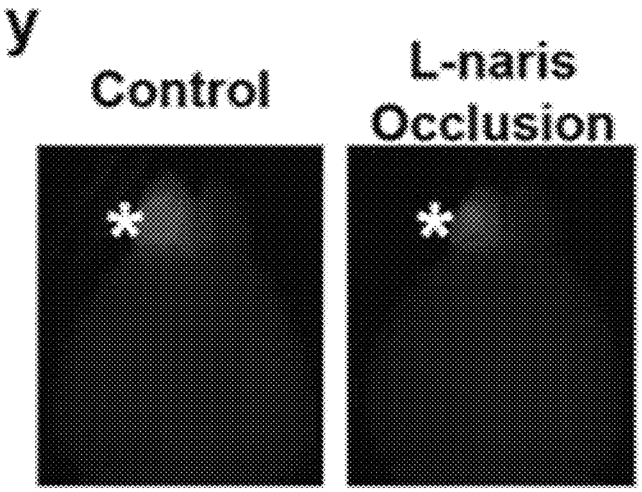
Figure 9Z:
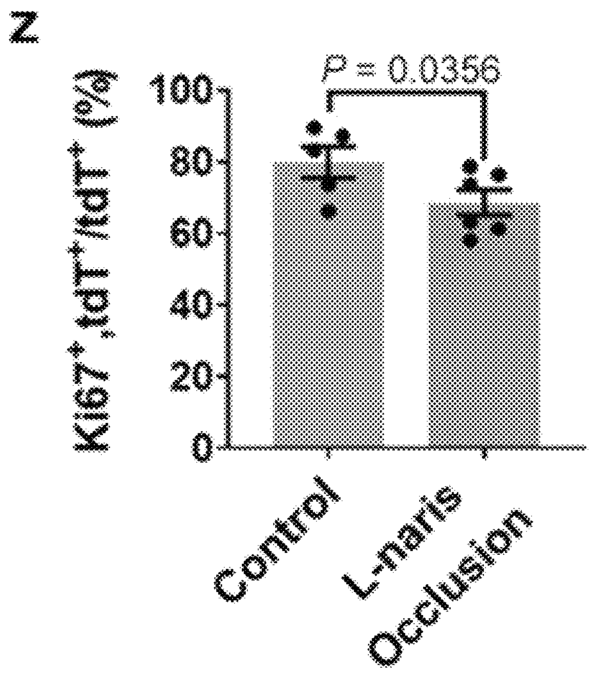

Next, whether olfaction deprivation suppressed gliomagenesis was determined. Quantitative analyses confirmed no difference in the incidence or the average size of tumors between the left and right OBs in control mice, indicating that under normal living conditions, gliomas developed in both bulbs in an unbiased fashion (FIG. 2k-m). In stark contrast, in the experimental group with left naris occlusion, tumors were significantly suppressed in the left (ipsilateral) bulb (FIG. 2k-m). Conversely, when the right nostrils were blocked, the tumors in the right bulbs were correspondingly suppressed (FIG. 2l, m). In concordance with the tumor stage, at the pre-transforming stage in olfaction-deprived mice (FIG. 9u), the density of proliferating mutant OPCs and the percentage of actively proliferating mutant OPCs were markedly reduced in the GL of the ipsilateral bulb when compared to the contralateral side (FIG. 9v, w). It was further confirmed that olfaction inputs also affect the progression of transformed tumor cells by using orthogonal grafting models where mouse glioma cells were implanted into the OBs of mice with or without naris occlusion (FIG. 9x-z). Therefore, all lines of evidence strongly suggest that olfactory experience not only regulates the initiation, but also the progression of gliomas in the present mouse model.

IGF Signaling Involves in Gliomagenesis

To identify the candidate mitogen involved in olfaction-related gliomagenesis, bulk RNA sequencing was performed on the OBs from naris-occlusion models and found that 17 genes were consistently downregulated (FIG. 3a, b). Selected genes were validated by RT-qPCR (FIG. 3c). Pro-tumoral effects of several candidates were tested but only IGF-1 significantly stimulated the proliferation of tumor OPCs in vitro (FIG. 3d). IGF-1 has been suggested to play important roles in normal olfactory behavior in mice, and its expression and/or secretion in neurons has been suggested to be activity-dependent[25,26].

Figure 10A:
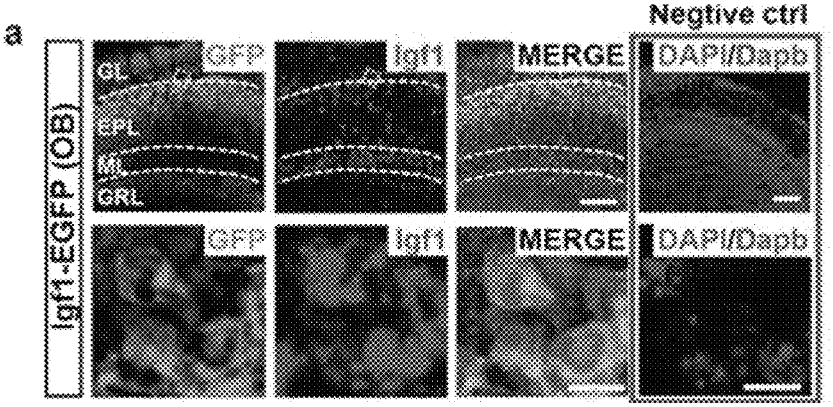
FIG. 10(*a*)-10(*g*) show characterization of EGFP expression in the OB of the Igf1-EGFP transgene: (a and b) Single-molecule FISH coupled with immunofluorescence confirms the co-localization of GFP protein and Igf1 mRNA in cells (M/T cells) from the OB (a) and the cerebellum (presumably Purkinje cells) (b) from the Igf1-EGFP transgene; (c) Representative image of EGFP expression in different layers of the OB from the Igf1-EGFP transgene; (d) The genotype configurations of the CKO_IGF1R model; (e) The proliferation rate of pre-transforming mutant OPCs in the GL, EPL and GRL layer of the CKO model after IGF1R is knocked out. N=6 OBs for the CKO and the CKO_IGF1R model respectively. P value: 0.0003, 0.0052 and 0.0086; (f and g) Quantification (f) and histological analysis (g) of $GFP^+$ cells among all known cell types in the OB of the adult mice (at the age of P30). Markers used to identify distinct cell types are indicated. N=3 mice. Scale bars: (a), 100 μm and 10 μm; (b), 100 μm and 20 μm; (c), 100 μm; (g), 50 μm. One-sided t-test in (e). p<0.01, *p<0.001. Data are presented as mean±SEM.
Figure 10B:
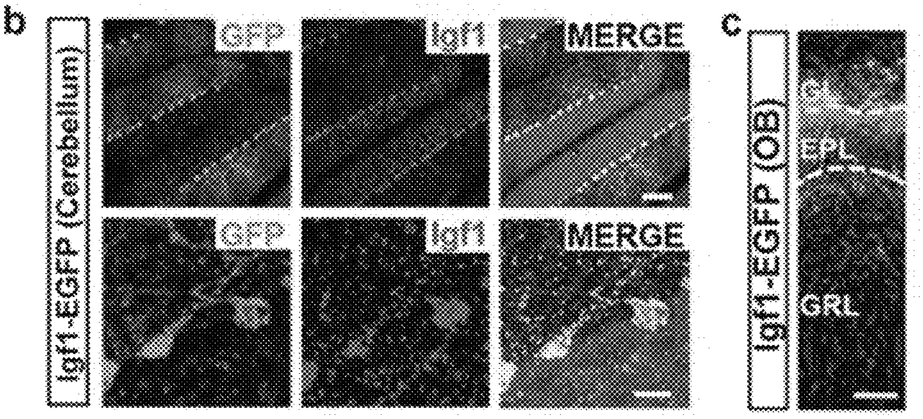

To identify the cellular sources of IGF-1 in the brain, an Igf1-EGFP BAC transgene (FIG. 3e) was constructed. The gross images of Igf1-EGFP mouse brain revealed that IGF-1 was mainly expressed in the OB (FIG. 3f), similar to the pattern reported in GENSAT using a different BAC vector. The faithfulness of the transgene was validated by single-molecule(sm) FISH (FIG. 10a, b). Similar to the Igf1 transcript shown in FIG. 3b, the level of EGFP exhibited a naris-occlusion-dependent decrease (FIG. 3g), further supporting the use of EGFP as a reporter to indicate the temporospatial expression of endogenous IGF-1.

Figure 10C:
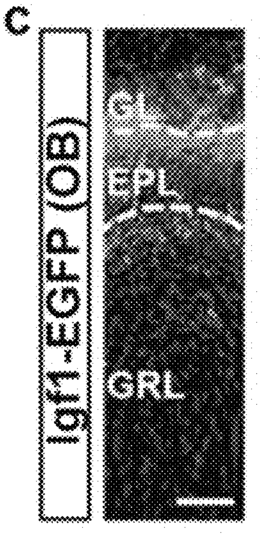
Figure 10D:
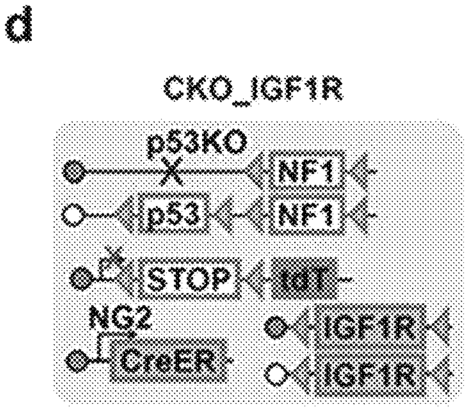
Figure 10E:
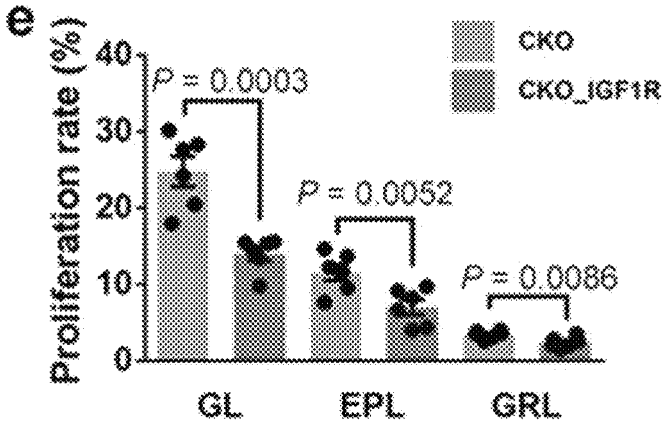

Brain structures with prominent EGFP expression in the reporter line highly overlapped with tumor hot spots (FIG. 6a). Furthermore, the proliferation rate of mutant OPCs at the pre-transforming stage was positively correlated with the expression level of IGF-1 in the corresponding brain region, and that pre-transforming OPCs within the brain regions with higher IGF-1 expression were more sensitive to the disruption of IGF signaling than those with lower IGF-1 expression (FIG. 10*c*-*e*). Therefore, our data suggest that IGF-1 is an important mitogen for olfaction-dependent gliomagenesis in the OB.

M/T Cells as IGF-1 Cellular Source

Figure 10F:
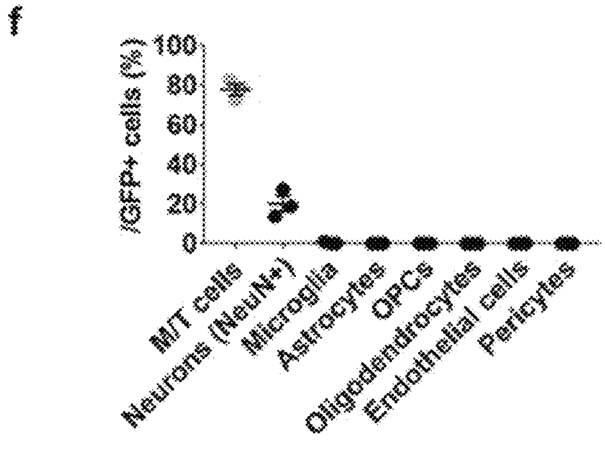
Figure 10G:
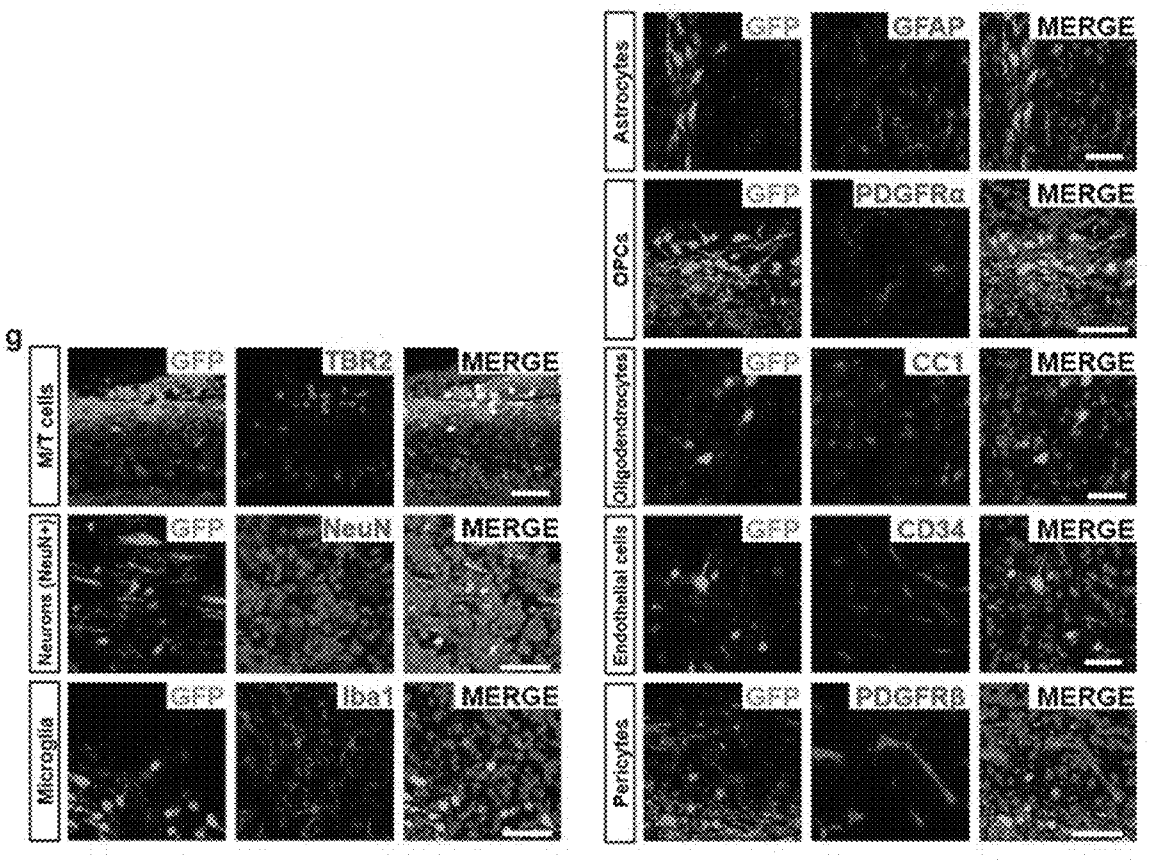

By using multiple cellular markers, it was confirmed that EGFP expression prominently overlapped with the Mitral/Tufted (MIT) cell marker TBR2, but not with those for glial cells, immune cells or other neurons (FIG. 3*h*, FIG. 10*f, g*). Therefore, it is conclude that M/T cells are the major cellular source of IGF-1 in mouse OB.

Figure 11A:
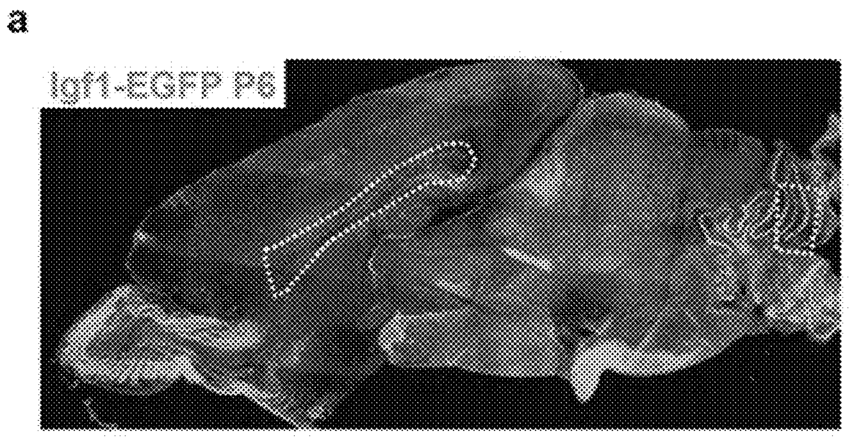
FIG. 11(*a*)-11(*h*) show the expression of IGF-1 in microglia is only minimally induced at the later stage of gliomagenesis: (a and b) Igf1-EGFP BAC transgene reveals the colocalization of GFP (presumably also Igf1) and the microglia marker IbaI in the cortex and the cerebellum at P6. N=2 mice are examined; (c) Genotype configuration of the CKO_Igf1-EGFP model, which is used to examine the cellular source of IGF-1 during gliomagenesis; (d) The colocalization of Igf1-EGFP with the marks of MIT cells and microglia in the OB tumor from the CKO_Igf1-EGFP model. H&E staining is provided to confirm tumor pathology. N=3 mice are examined; (e) Percentage and average intensity of Igf1-expression microglia and tufted cells in the CKO_Igf1-EGFP model grouped by endpoint. N=10 mice. Two-sided Pearson correlation coefficients are calculated; (f and g) Percentage and intensity (f) and representative images (g) of Igf1-expression microglia and M/T cells in the CKO_Igf1-EGFP model from (e) grouped by tumor volume. N=6 mice for small group and N=4 mice for big group. P=0.0443, 0.1171 and 0.1357; (h) The proximal position of the terminals from $GFP^+$ M/T cells with $tdT^+$ glioma cells in the OB of CKO_Igf1-EGFP model. Orthogonal views are provided to further validate the interactions between two types of cells. N=2 tumors are examined. Scale bars: (b), 200 μm, 50 μm and 100 μm; (d), H&E staining, 400 μm, immunofluorescence, 50 μm; (g), 200 μm; (h), 10 μm. One-sided t-test in (f). ns, no significant, *p<0.05. Data are presented as mean±SEM.
Figure 11B:
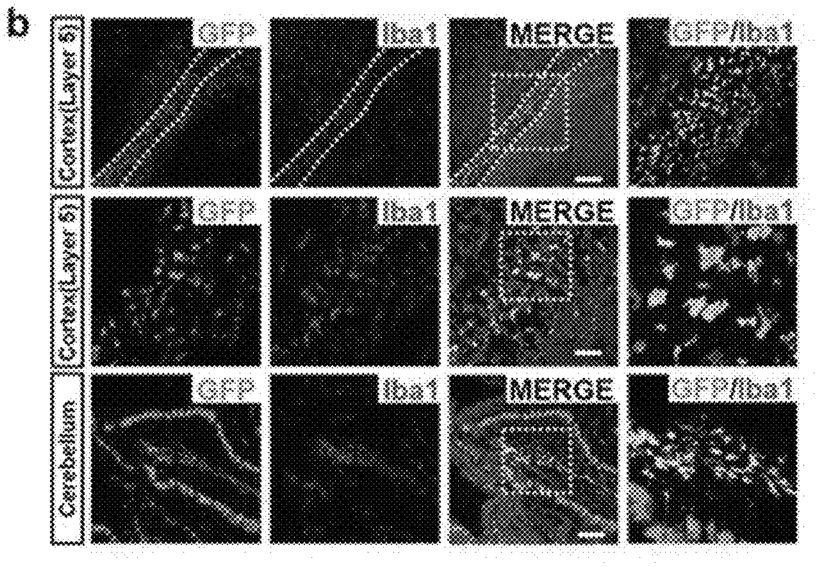
Figure 11C:
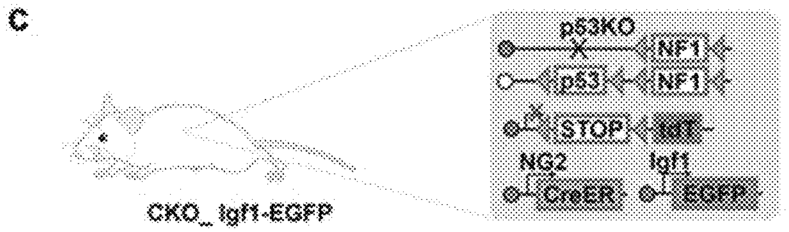
Figure 11D:
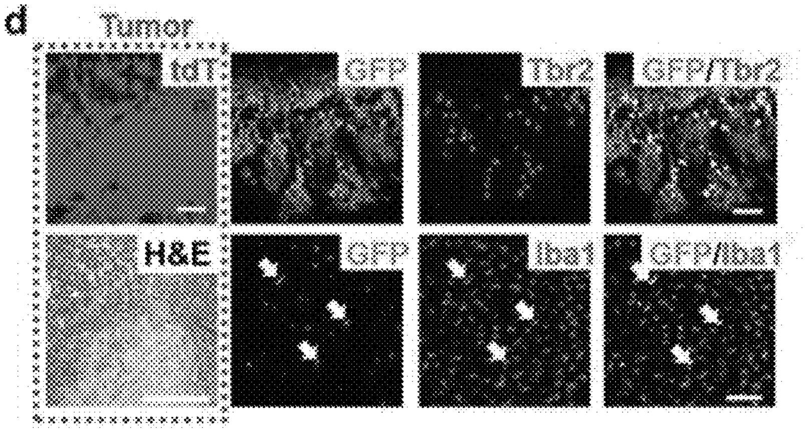
Figure 11E:
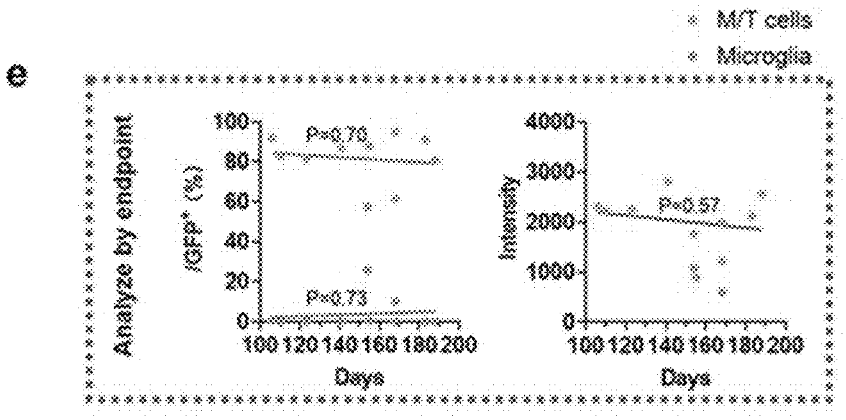
Figure 11F:
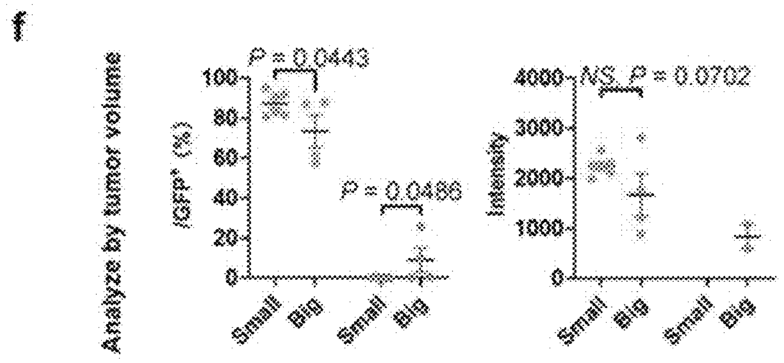
Figure 11G:
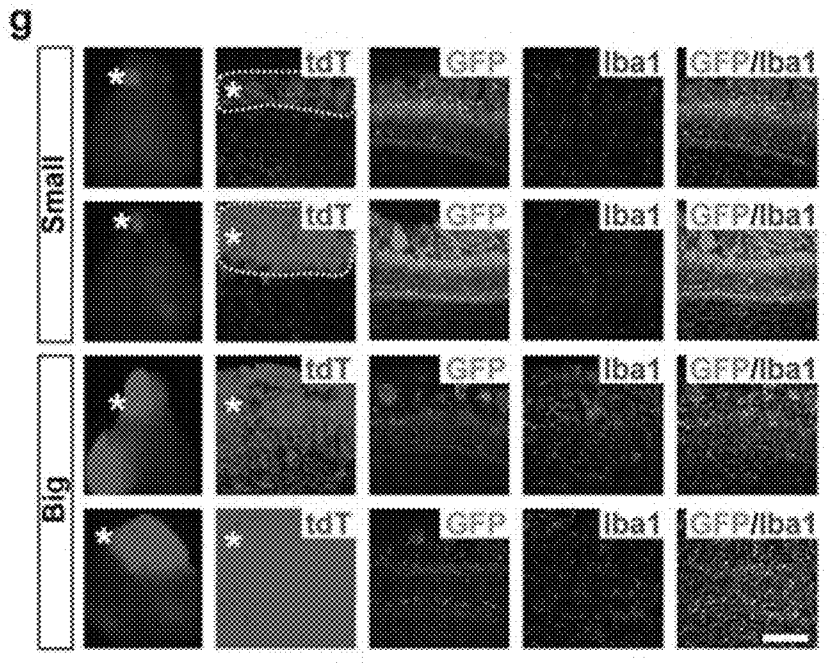
Figure 11H:
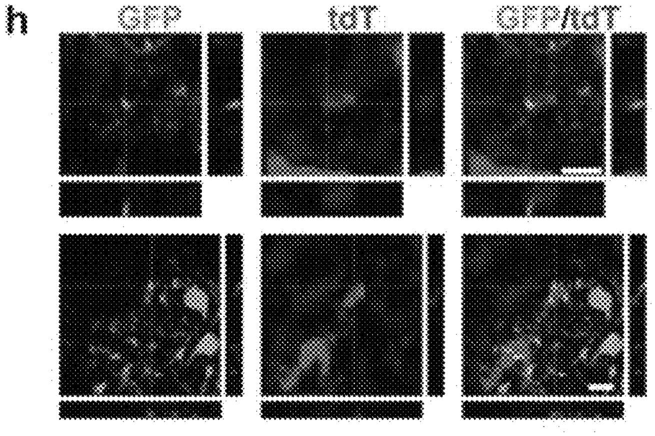

Previous studies have reported that microglia can function as a cellular source of IGF-1 under multiple normal or pathological conditions, including brain tumors. However, in the present application, by using the IGF-1 reporter lines suggest that microglia contribute trivial IGF-1 either in the normal mouse forebrain throughout development (FIG. 11*a, b*) or in the tumor mass throughout tumor development (FIG. 11*c*-*g*). In contrast, M/T cells contributed to the majority of $IGF1^+$ cells in the tumor regardless of tumor age or tumor size. Interestingly, immunofluorescent imaging revealed some direct contact between tumor cells and the process of M/T cells (FIG. 11*h*). These observations, together with the WES results shown in FIG. 7*b* and the whole brain images in FIG. 6, 3, raise an intriguing possibility that (pre-) cancerous OPCs might be able to migrate along the process of M/T cells to deep brain regions during tumor progression.

Igf1 Knockout Suppresses Gliomagenesis

Figure 4:
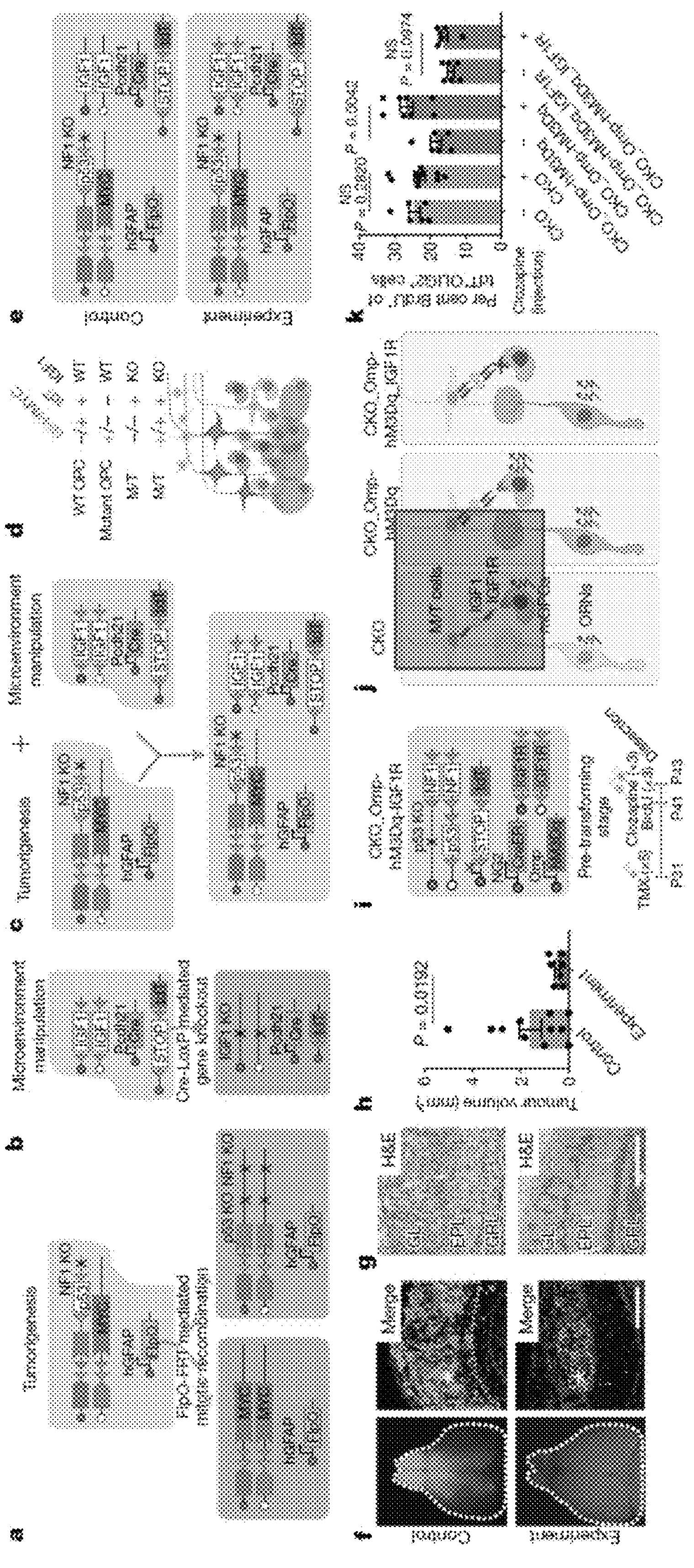
FIG. 4. shows gliomagenesis via IGF-1 from Mitral/Tufted cells promoted by olfaction-influenced neuronal activity: (a-c) Working mechanism of the dual recombinase MADM model. FlpO-FRT mediated mitotic recombination generates tdTomato-labeled WT cells and GFP-labeled mutant cells to mimic sporadic tumorigenesis from embryonic NSCs (a). Cre-LoxP-mediated genetic recombination specifically knocks out of Igf1 from M/T cells (b). The final dual-recombinase MADM model (c) combining (b) and (c) achieves simultaneous recapitulation of tumorigenesis with single-cell resolution and specific knockout of the gene of interest (Igf1 here) in the tumor microenvironment. In the dual recombinase MADM model, the generation of mutant and WT cells in the tumor lineage is induced by the hGFAP-FlpO and IGF-1-null M/T cells by Pcdh21-Cre. Both transgenes are made in this study. Yellow triangle: FRT site; (d) Schematic diagram to distinguish distinct types of cells labeled in the dual recombinase MADM model; (e) Genotype of the dual recombinase MADM (control, normal IGF-1) and MADM_IGF1 (experiment, IGF-1 removed from M/T cells) model; (f-h) Representative immunofluorescence images (f), hematoxylin and eosin (H&E) staining (g) and quantification of tumor volumes in the OB (h) of the control and the experiment model at the tumor stage (P130). Tumor regions are demarcated with dashed lines and marked with asterisks. N=11 mice for the control group, N=7 mice for the experiment group. P value: 0.0192; (i) The genotype configurations of the CKO_Omp-hM3Dq_IGF1R model and scheme of the experimental procedure for (k); (j and k) Schematic of working mechanisms (j) and proliferation rate of mutant OPCs (k) in the CKO, CKO_Omp-hM3Dq and CKO_Omp-hM3Dq_IGF1R model as treated in (i). Of note, the same dataset of CKO and the CKO_Omp-hM3Dq model are also presented in FIG. 8*m*. N=6 OBs for both groups of the CKO_Omp-hM3Dq_IGF1R model. P=0.2820, 0.0042, 0.0974 respectively. Scale bars: (f) and (g): 100 μm. One-sided t-test in (h) and (k). ns, no significant, *p<0.05, **p<0.01. Data are presented as mean±SEM.
Figure 12A:
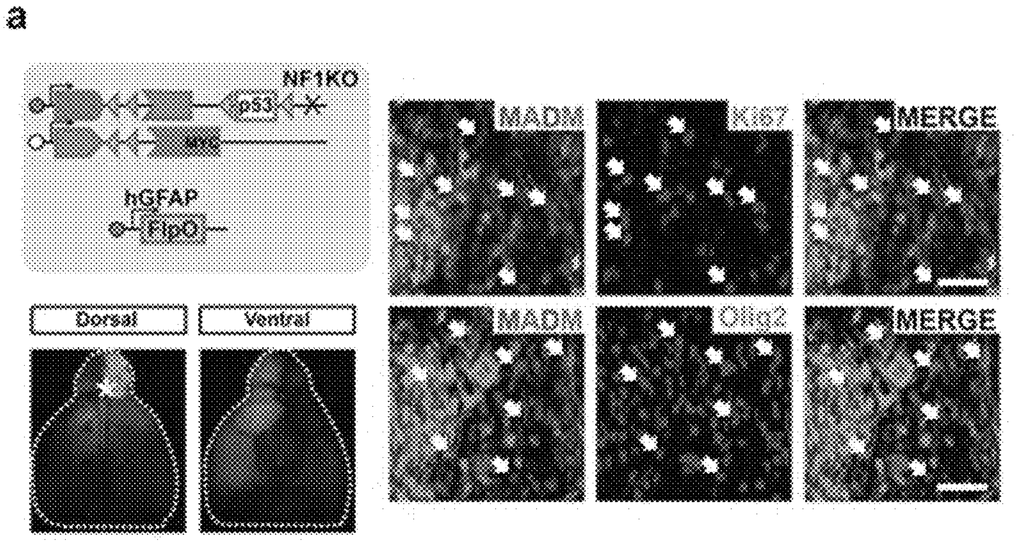
FIG. 12(*a*)-12(*g*) show Establishment and characterization of the dual recombinase MADM model: (a) Genotype and the representative images of the MADM_hGFAP-FlpO tumor model. Brain boundaries are demarcated by dashed lines. The asterisk indicates the tumor region. Of note, tumors preferentially appeared in the olfactory brain structures. N=5 mice are examined; (b) For $Pcdh21^+$ M/T cells, Cre recombinase induces the knockout of Igf1 alleles and simultaneous turns the cells into red. Notably, if the Cre does not induce the inter-chromosomal recombination between the MADM cassettes, $tdT^+$, $GFR^+$, $cMyc^+$ cells will be generate (left branch). If Cre recombinases conduct the inter-chromosomal recombination between the MADM cassettes, $tdT^+$, $GFP^+$, $cMyc^-$ will be generated as shown in right branch and (g). Importantly, Pcdh21-Cre never expressed in OPCs or tumor cells; (c) The breeding scheme to generate the dual recombinase MADM_IGF1 model; (d-g) Orthogonal analysis of the dual recombinase MADM model to validate the independent labeling of the Cre-LoxP and the FlpO-FRT recombination systems in the same mouse. The configuration for each genetic composition is provided on the left. N=2 mice are examined. Scale bars: (a), 40 μm; (d-g), 40 μm.

To unambiguously determine whether M/T cells play critical roles in gliomagenesis by providing IGF-1, it is necessary to specifically knock out Igf1 from M/T cells without disturbing the native microenvironment of tumor initiation and progression. To achieve this goal, a previously established genetic system termed Mosaic Analysis with Double Markers (MADM) was adopted, combining the conventional conditional gene knockout system in the same model (FIG. 4*a*-*d*). Notably, the pre-designed FRT site in the MADM_ML system allows hGFAP-FlpO-dependent inter-chromosomal recombination and subsequent generation of gliomas in this model (FIG. 4*a*, FIG. 12*a*). Therefore, simultaneous application of two orthogonal DNA recombinases (Cre and FlpO) enabled independent manipulation of tumor cells and their microenvironment in a highly precise manner (as shown in FIG. 4*a*-*d*).

Figure 12B:
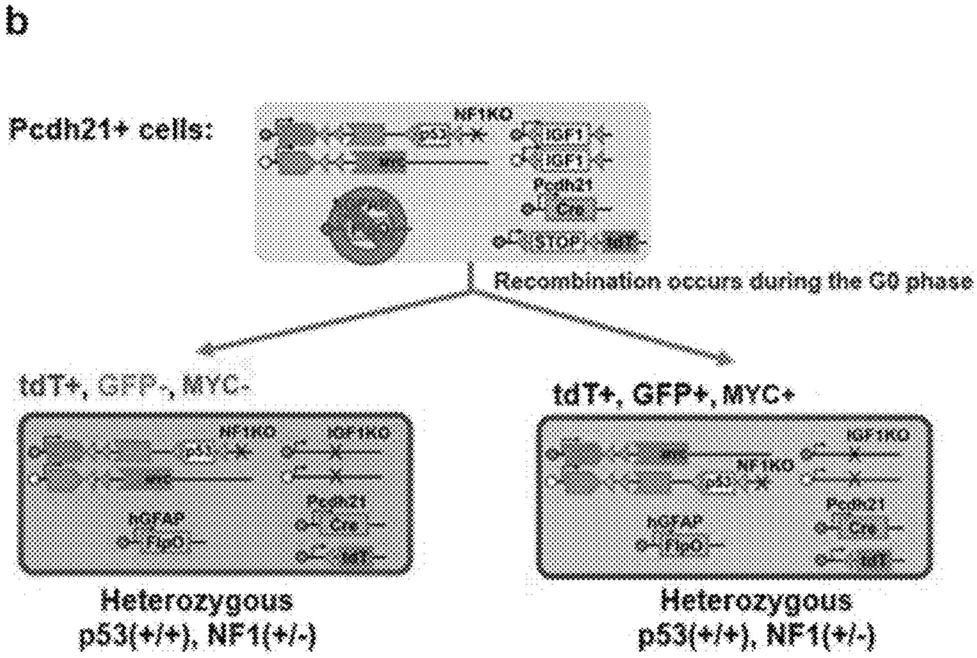
Figure 12C:
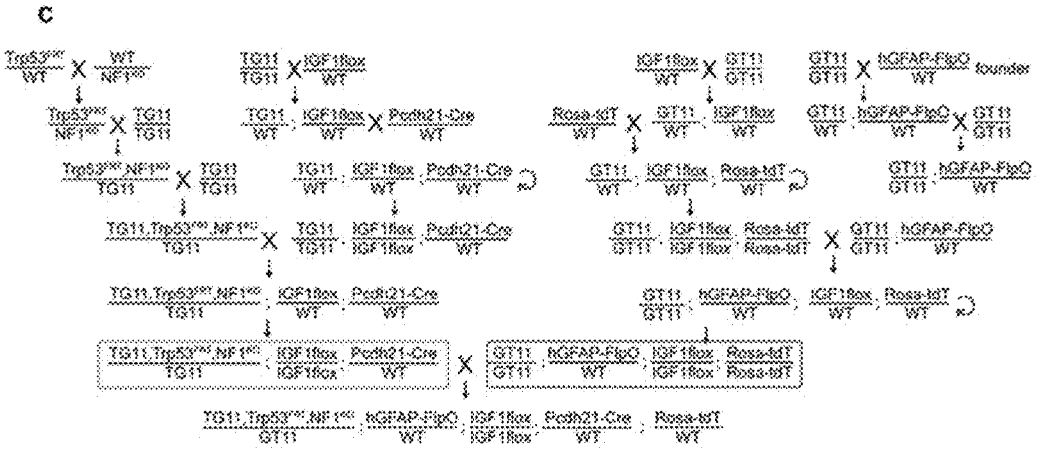

To specifically remove Igf1 in M/T cells, a BAC transgene was created to express Cre recombinase under the control of the M/T cell-specific Pcdh21 promoter, and this transgene together with the homozygous $IGF1^{flox/flox}$ alleles was incorporated into the final model (FIG. 4*e*). To visualize the specificity of Igf1 knockout cells, the Cre-dependent reporter $Rosa26^{LSL\text{-}tdTomato}$ was also included (FIG. 4*e*). Notably, MADM-derived $tdTomato^+$ cells can be easily distinguished from those labeled by Pcdh21-Cre based on their unique expression of the Myc tag (as illustrated in FIG. 4*d* and FIG. 12*b*). The breeding scheme to build up the final dual recombinase MADM glioma model is presented in FIG. 12*c*.

Figure 12D:
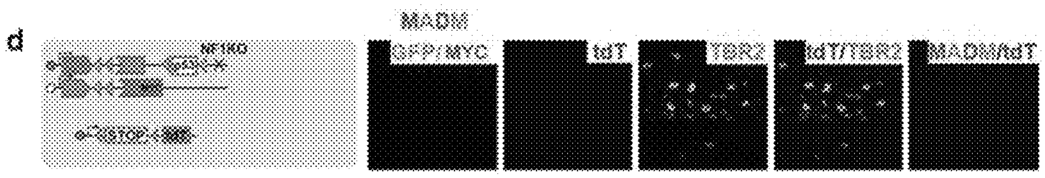
Figure 12E:
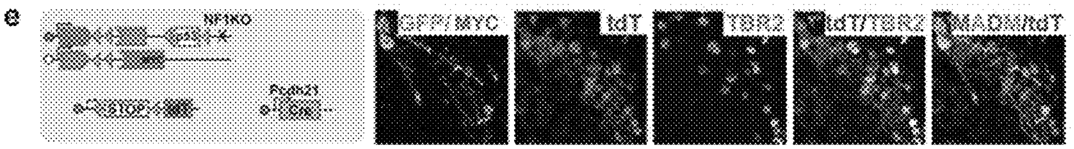
Figure 12F:
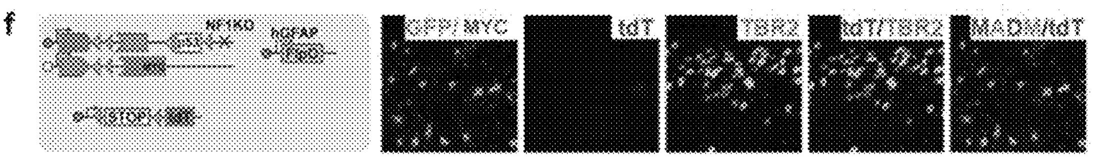
Figure 12G:
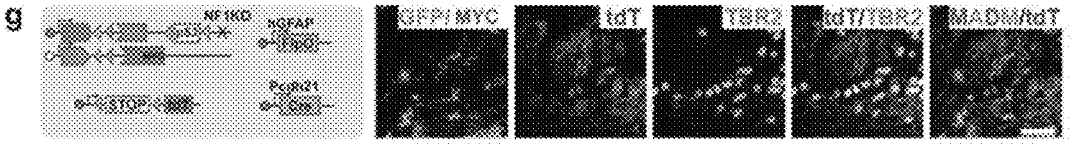
Figure 13A:
FIG. 13(*a*)-13(*k*) show that M/T-specific rather than microglia-specific Igf1 knockout affects gliomagenesis; and igf1 depletion did not disturb the overall Igf1 expression pattern: (a-c) The analysis scheme (a), representative images (b) and the proliferation rate of mutant cells (c) in the OB of the control and the experiment group at the pre-transforming stage (P60). Arrows point to the proliferating mutant cells. N=6 OBs for the Control group and N=8 OBs for the Experiment group. P value in (c): 0.0066; (d) Single-molecule FISH coupled with immunofluorescence confirms no other cell types such as microglia regained the abnormal expression of IGF1 to paly redundant function as the cellular resource for tumor OPCs. N=988 $Iba1^+$ cells for WT group, N=1207 $Iba1^+$ cells for IGF1flox; Pcdh21-Cre-P40 group, N=1167 $Iba1^+$ cells for IGF1flox; Pcdh21-Cre-P100 group, N=2 mice for each group; (e) Igf1 transcript from OBs of the IGF1flox and IGF1flox; Pcdh21-Cre mice. IGF1flox; Pcdh21-Cre mice show prominent Igf1 KO bands. P-F, primer Igf1-Full-Forward; P-R, primer Igf1-Full-Reversed. For primers, see Supplementary Table 1. N=2 mice for each group; (f and g) Validation of the intersectional genetic manipulation of tumor cells and microglia in the dual-recombinase genetic system. Genotype (f) and characterization (g) of MADM_Cx3cr1 model. In MADM model, $tdT^+$ cells are all $cMyc^+$, which are generated by FlpO-dependent inter-chromosomal recombination. In MADM_Cx3cr1 model, $cMyc^+$, $tdT^+$ cells can be easily found and all of them are $Iba1^+$ microglia generated by Cre-dependent recombination; (h-k) Genotype (h), representative images (i), treatment scheme j) and tumor volume quantification (k) of MADM_Cx3cr1 and MADM_Cx3cr1_IGFT model. N=5 mice for MADM_Cx3cr1 model and N=6 mice for MADM_Cx3cr1_IGFT model. P value: 0.3707. Scale bars: (b), 40 μm; (d), 100 μm; (g), 50 μm; (i), 50 μm. One-sided t-test in (c) and (k). ns, no significant, **p<0.01. Data are presented as mean±SEM.
Figure 13B:
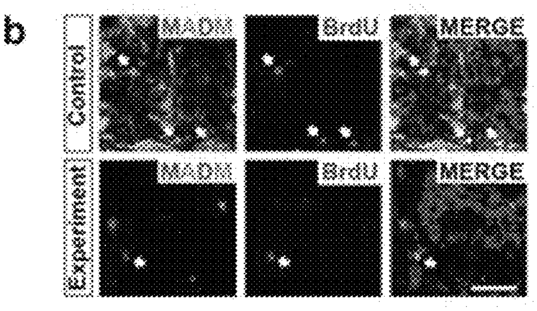
Figure 13C:
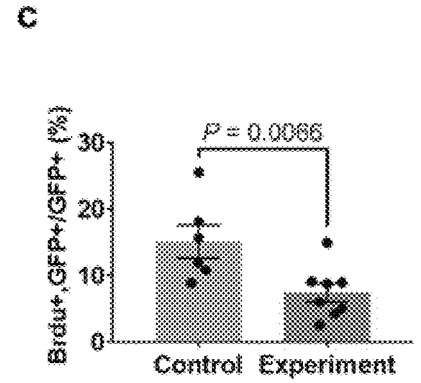
Figure 13D:
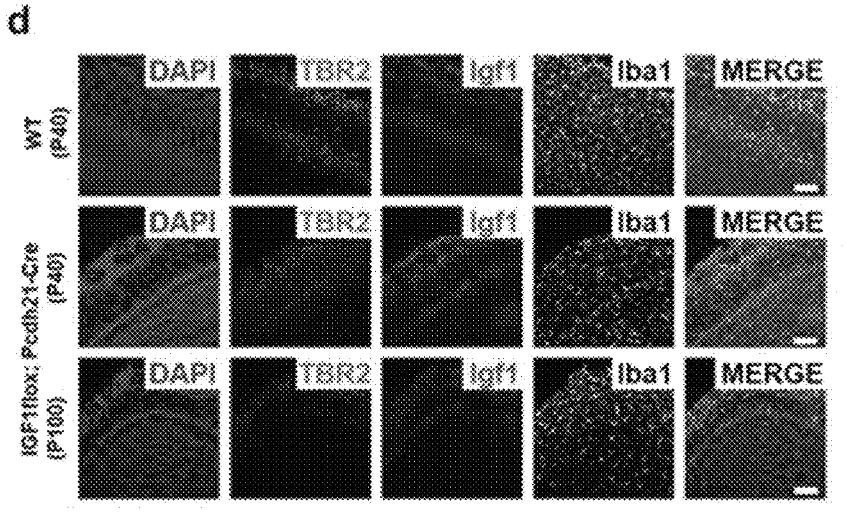
Figure 13E:
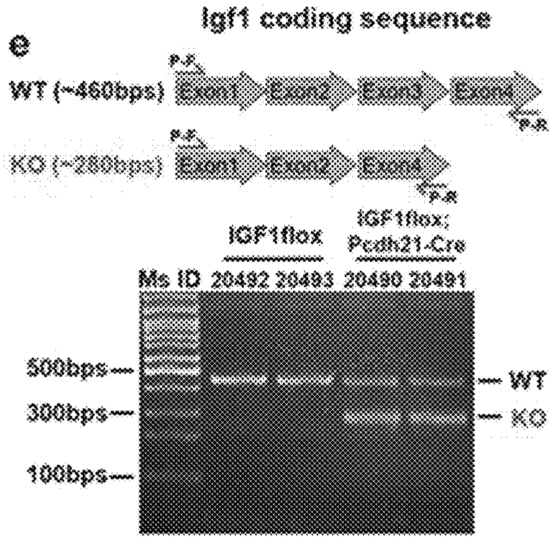
Figure 13F:
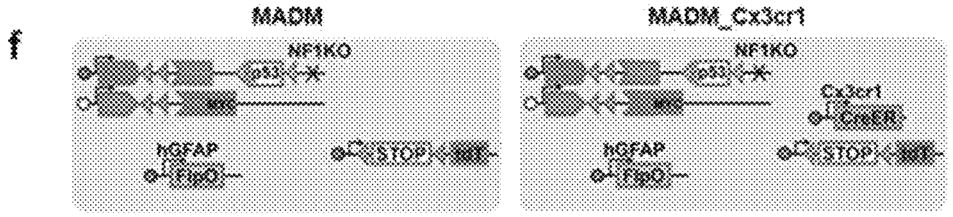
Figure 13G:
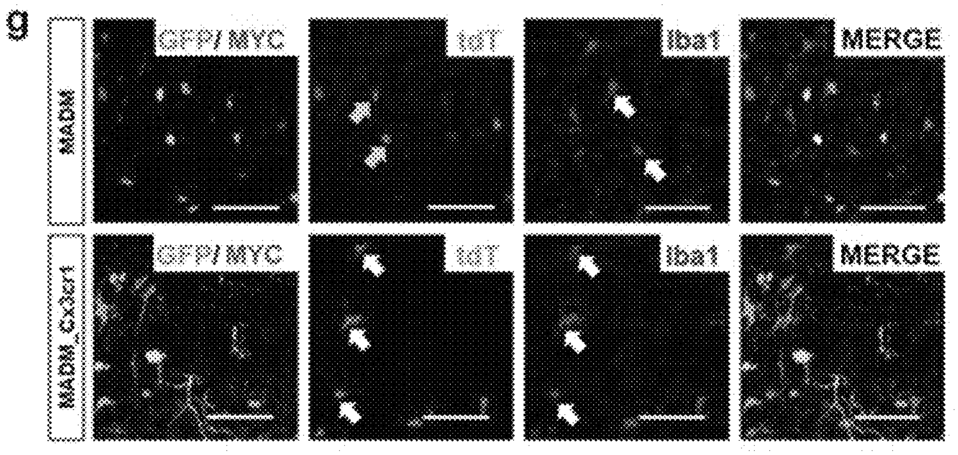
Figure 13H:
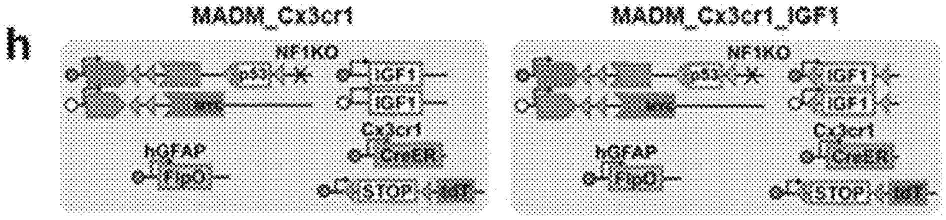
Figure 13I:
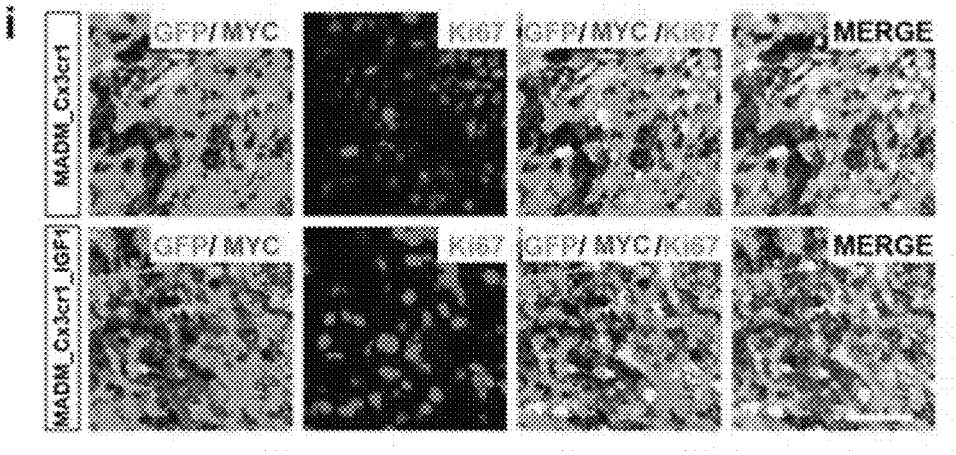
Figure 13J:
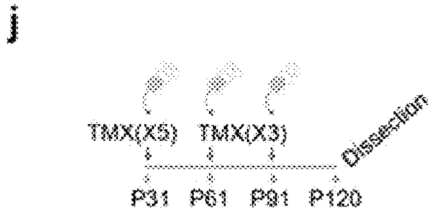
Figure 13K:
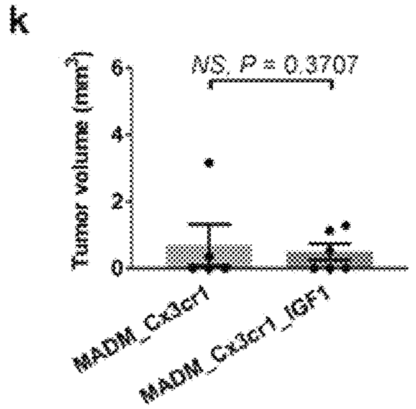

It twas validated that the hGFAP-FlpO and Pcdh21-Cre transgenes in this dual-recombinase model worked independently with each other (FIG. 12*d*-*g*). In the absence of both recombinases, no labeled cells were detected in the brain (FIG. 12*d*). When Pcdh21-Cre was introduced, tdTomato M/T cells were generated (FIG. 12*e*). Of note, due to the direct GO-interchromosomal recombination in M/T cells, some MADM-labeled yellow M/T cells could also be seen (as explained in FIG. 12*b*). In contrast, when hGFAP-FlpO was incorporated, $GFP^+$ mutant OPCs along with other NSC-derived WT/mutant cells were found (FIG. 12*f*). When hGFAP-FlpO and Pcdh21-Cre were present simultaneously, both $GFP^+$ tumor-lineage cells and $tdTomato^+$ M/T cells were observed (FIG. 12*g*). With the availability of this novel model system, we demonstrated that knockout of Igf1 specifically in M/T cells significantly suppressed the transformation of mutant OPCs in the OB at the tumor stage (FIG. 4*f*-*h*). Knockout of Igf1 also decreased proliferation rate of mutant OPCs at the pre-transforming stage (FIG. 13*a*-*c*). Importantly, knockout of Igf1 in M/T cells did not affect the overall expression pattern of Igf1 in the OB at different developmental time points (FIG. 13*d, e*). Following the similar strategy, the microglia specific-Igf1 knockout dual-recombinase glioma model was established. However, knockout of microglia-derived IGF-1 did not affect the tumor progression (FIG. 13*f*-*k*).

Olfaction Affects Glioma by IGF Pathway

To validate whether olfaction-regulated gliomagenesis mainly depend on IGF signaling, given that many other neuronal growth factors may also be released upon olfaction stimulation, in an in vivo context, the $IGF1R^{flox/flox}$ homozygous alleles was brad into the CKO_Omp-hM3Dq model to simultaneously activate ORNs and block IGF-1-dependent activation of IGF1R signaling in tumor OPCs (FIG. 4*i, j*). The results clearly show that IGF1R knockout fully abolished the increase in proliferation of mutant OPCs in the CKO_Omp-hM3Dq model upon clozapine administration (FIG. 4*k*). It was concluded that olfactory experience regulates gliomagenesis mainly through activity-dependent IGF-1 in M/T cells.

The IGF-1 Function is not by Synapses

Figure 14A:
FIG. 14(*a*)-(*g*) shows the mitogenic effect of IGF-1 independent from the neurotransmitter receptor mediated signals: (a) The t-SNE map of single cell sequencing data of CKO tumor from previous published work[16]; (b) Expression pattern of neurotransmitter receptor genes in the all clusters defined above. Tumor cell clusters including astrocytes-like tumor cells and OPC-like tumor cells. Same color code is used in (a) and (b); (c) Glioma cells from the CKO model co-cultured with primary OB neurons are collected following the flow chart; (e) Representative up-regulated genes and neurotransmitter receptor genes of glioma cells which are co-cultured with OB neurons and stimulated by IGF-1 compared to co-cultured glioma cells without IGF-1 stimulation. Full list of gene expression level can be found in Supplementary Table 2. N=2 biologically independent wells without stimulation and N=3 biologically independent wells with stimulation; (f) Proliferation rate of two independent CKO model derived glioma cell lines treated with 20 ng/mL IGF-1, 20 ng/mL IGF-1 and 10 μM AMPA-receptor antagonist DNQX, 10 μM DNQX, 200 μM glutmate, 200 μM GABA and 15 mM KCl. N=4 biologically independent wells for each group. P value for 1483; Ctrl vs IGF-1, <0.0001; IGF-1 vs $IGF\text{-}1^+$ DQNX, 0.9988; Ctrl vs DQNX, 0.5924; Ctrl vs GLU, >0.9999; Ctrl vs GABA, 0.9991; Ctrl vs KCl, 0.9988. P value for 1877; Ctrl vs IGF-1, <0.0001; IGF-1 vs IGF-1+DQNX, 0.7940; Ctrl vs DQNX, 0.9069; Ctrl vs GLU, 0.4102; Ctrl vs GABA, 0.9589; Ctrl vs KCl, 0.1199; and (g) Working model of olfaction affecting gliomagenesis through neuronal activity dependent IGF-1. One-way ANOVA with Dunnett's multiple comparison post-hoc test in (f). ns, no significant, ****p<0.0001. Data are presented as mean in (e) and mean±SEM in (f).
Figure 14B:
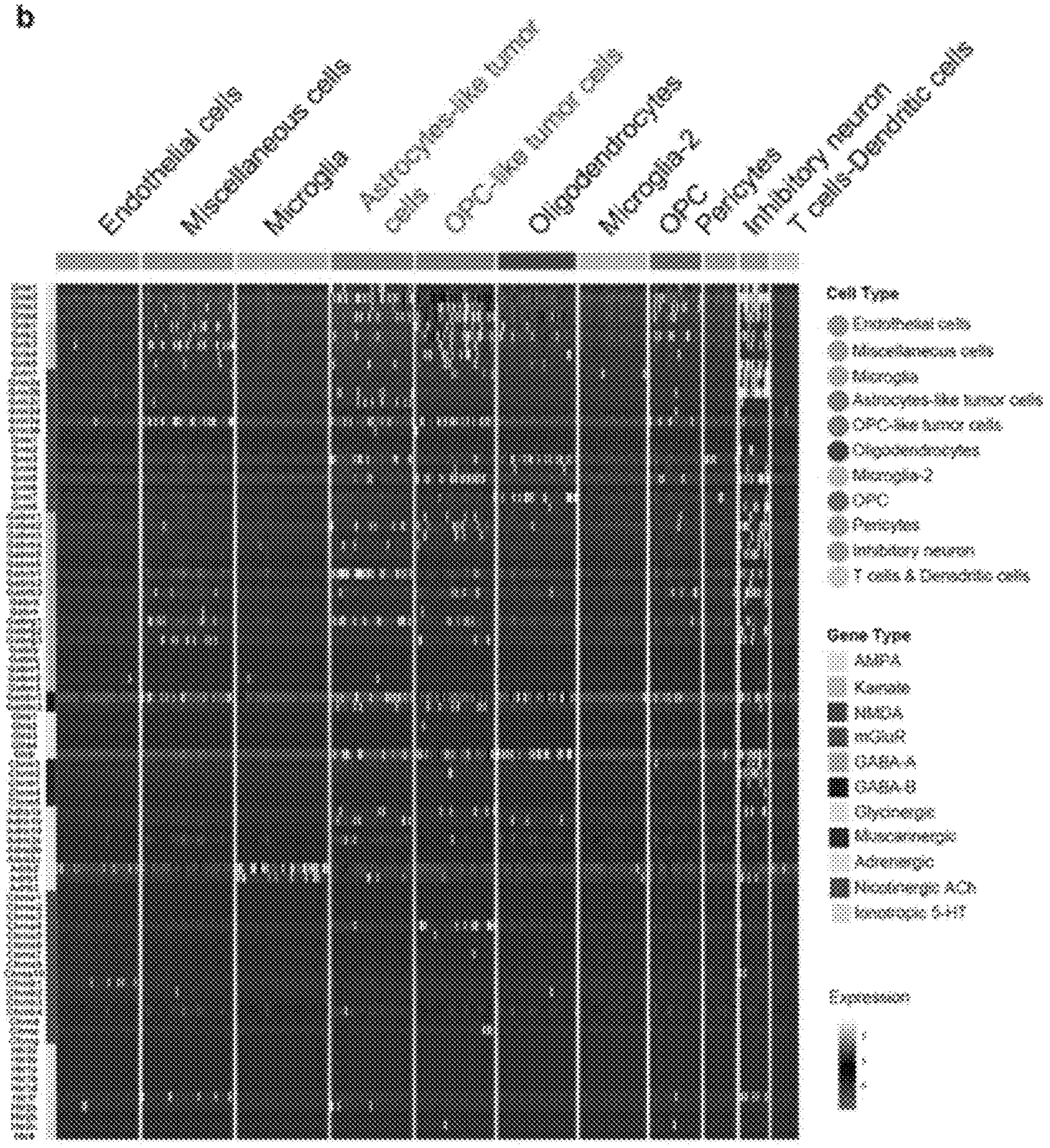
Figure 14C:
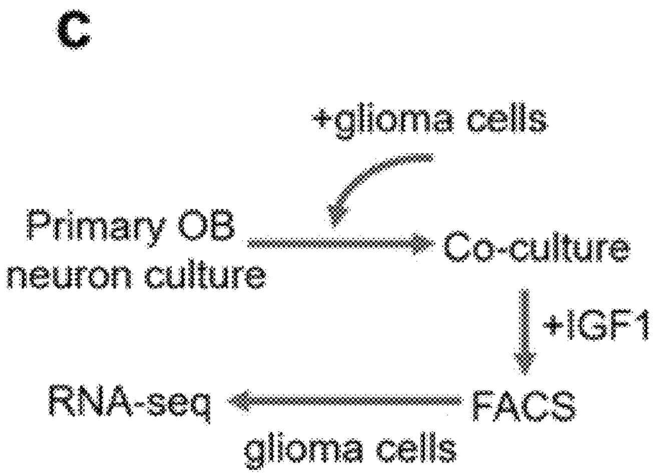
Figure 14D:
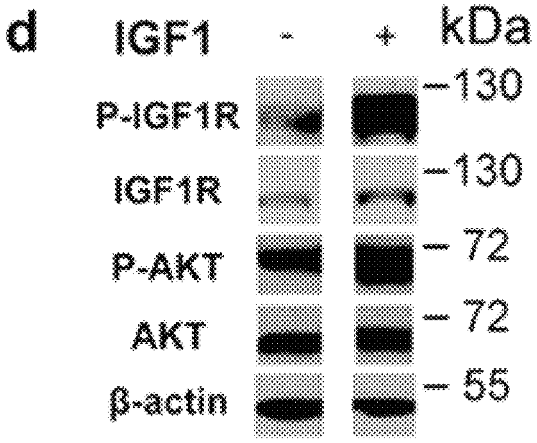
Figure 14E:
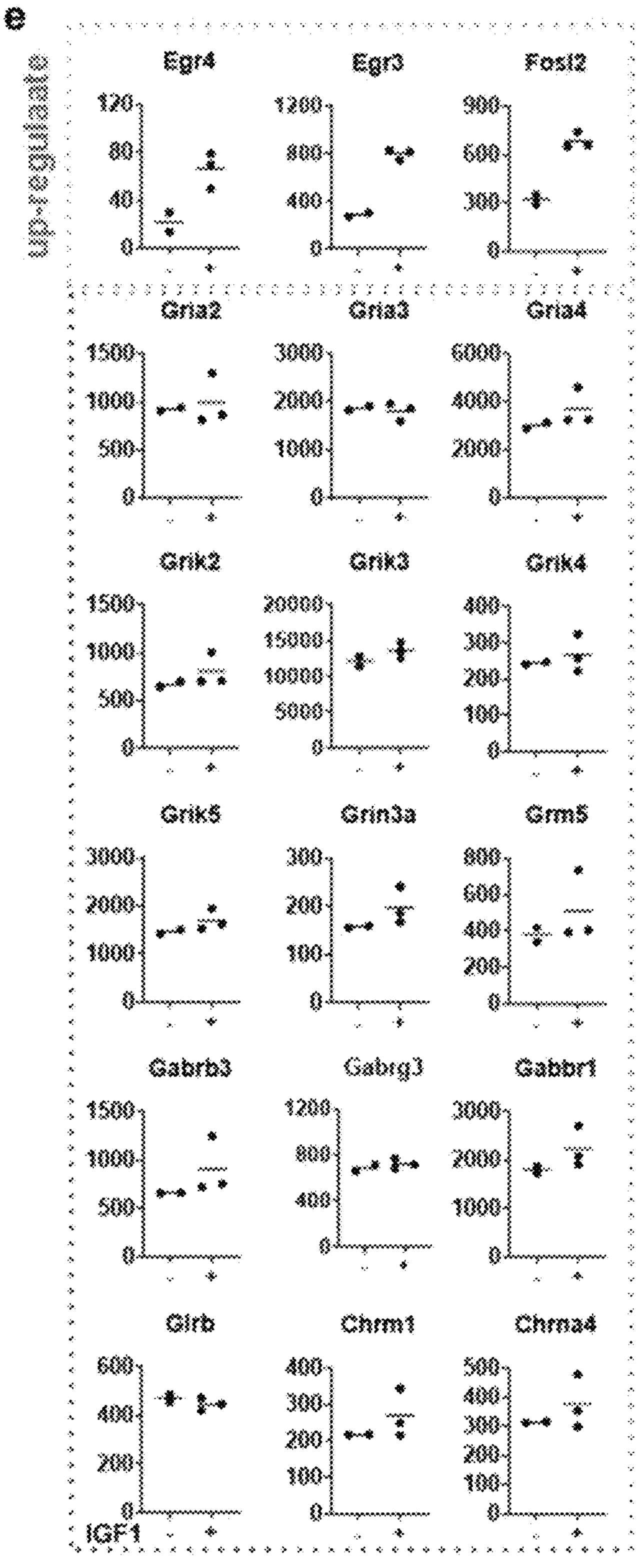
Figure 14F:
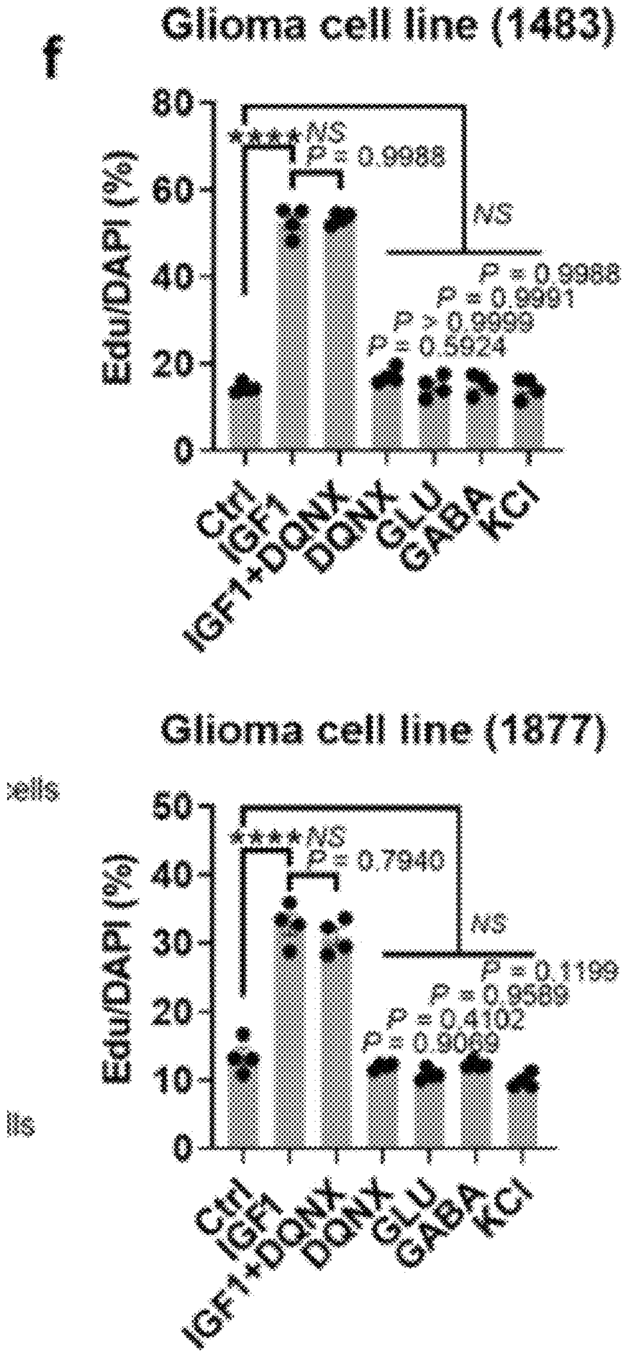
Figure 14G:
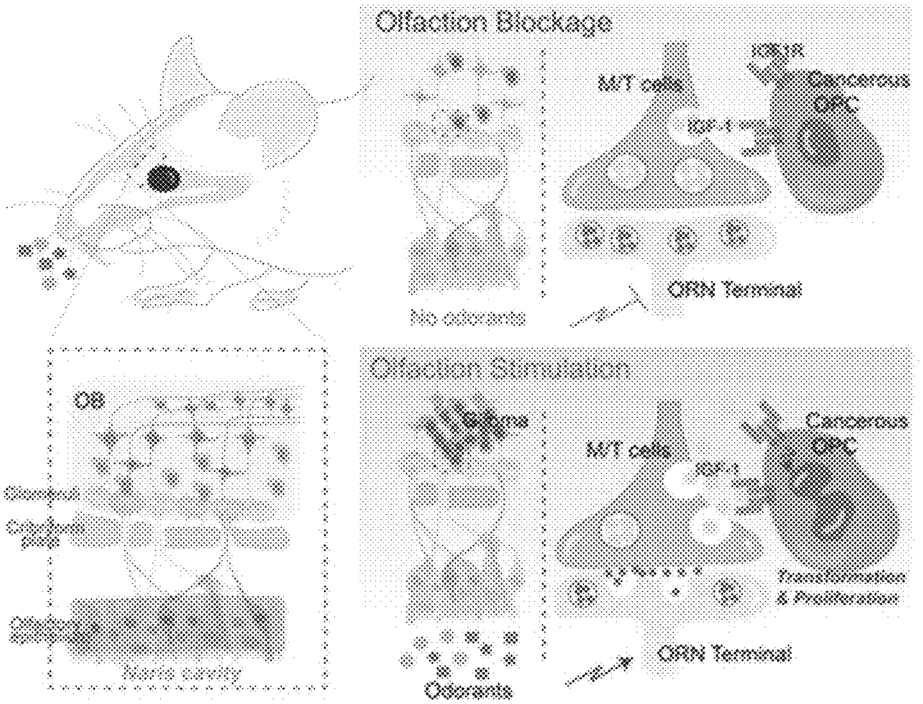

Despite single cell profiles of the CKO tumor clearly show that tumor OPCs expressed a panel of neurotransmitter receptor genes including AMPARs (FIG. 14*a, b*), IGF-1 did not affect the expression of these genes in tumor OPCs from the tumor cell M/T co-cultures. In contrast, significant upregulation of some receptor tyrosine kinase (RTK) downstream genes such as Egr3/4 and Fos12 were detected (FIG. 14*c*-*e* and Supplementary Table 2). Glutamate, GABA, or potassium chloride did not affect the proliferation of tumor OPCs. In addition, DQNX, an AMPAR antagonist, did not affect the IGF1-promoted proliferation of tumor OPCs (FIG. 14*f*). Therefore, it can be concluded that IGF-1 regulates gliomagenesis independent of neurotransmitter-receptor signals, but is more likely to do so through classic RTK pathways.

Interneuron are another important type of neurons in the cerebral cortex besides excitatory neurons. They regulate neuronal activity by releasing inhibitory neurotransmitter GABA. Whereas IGF-1 in the normal adult brain is mainly synthesized by interneurons, the Gad2-Cre mouse strain can express Cre specifically in interneurons and thus via Gad2-Cre; IGF-1 flox, knockout of IGF-1 in interneurons can be achieved. Combined with the MADM genetic model of glioma based on the FLP-FRT recombinase system in the present application, the tissue-specific Cre (ER)—loxP conditional knockout system enables mutually independent genetic manipulation of tumour generation.

Figure 15:
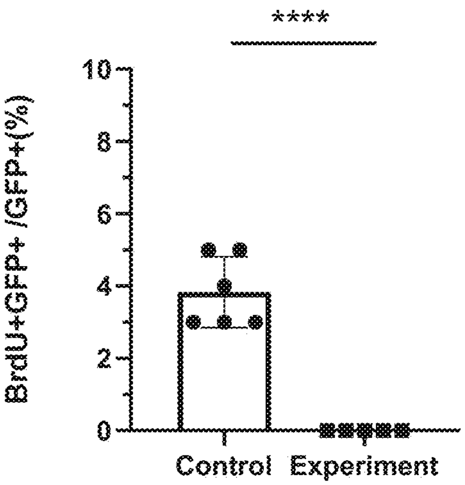
FIG. 15 shows a proliferation rate of mutant OPCS during the prophase of transformation after knocking down the interneuron-derived IGF-1 vs. that in a control group.
Figure 16:
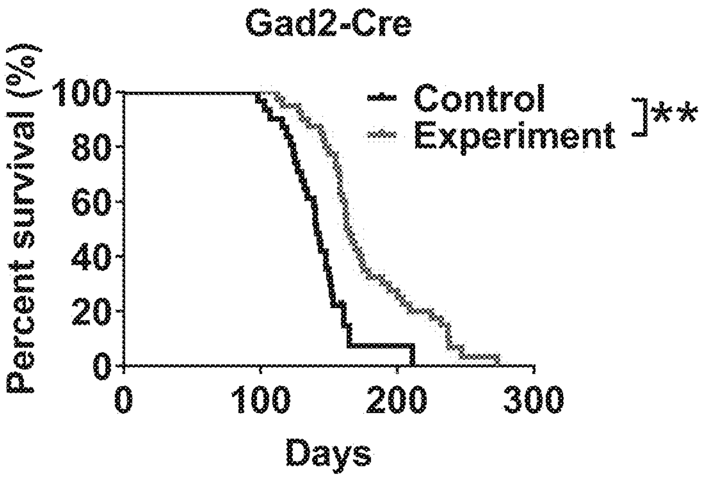
FIG. 16 shows the survival time of a MADM glioma mouse model with specific knockout of IGF-1 derived from Gad2 positive cells (intermediate neurons).

In particular, a transgenic mouse line IGF1flox (B6.129 (FVB)-Igf1tm1Dlr/J, JAX:016831) was generated, in which IGF1 was knocked out by Cre mediated recombination, combined with different cell specific Cre lines to achieve knockout of IGF1 in specific cell sources. Correspondingly, specific knockout of IGF1 in interneuron was performed in models MADM_p53FRT, NF1Rec_TG; IGF1flox; hGFAP-FlpO; and Gad2-Cre to study its impact on the occurrence and development of glioma. BrdU staining was used to study the effect of knocking out interneuron-derived IGF1 on the proliferation rate of precancerous mutant OPCs. BrdU was administered on consecutive days before mice dissection, the proliferation rate of mutant OPCs was calculated as the number of proliferative mutant cells (BrdU+GFP+MYC−) cells divided by the number of mutant cells (GFP+MYC−). It was found that the proliferation rate of mutant OPCs during the pre-transforming stage was significantly reduced after knocking down the interneuron-derived IGF-1 (FIG. 15). Survival analysis of glioma model mice with knock-down of interneuron-derived IGF1 was performed and it was found that the survival time of the experimental group was significantly prolonged compared to the control group (FIG. 16). This suggests that interneuron derived IGF-1 is important for glioma development and may be an important therapeutic target.

Examples

Methods

Mouse Lines

All animal procedures were based on animal care guidelines approved by the Institutional Animal Care and Use Committee of Zhejiang University School of Medicine. For anatomical experiments, both male and female mice were used. Following strains were used to build up the genetic mouse models in this study: NG2-CreER (B6.Cg-Tg(Cspg4-cre/Esr1*)BAkik/J, JAX:008538), Rosa-tdTomato (Ai9, B6.Cg-Gt(ROSA)26Sor$^{tm9(CAG\text{-}tdTomato)Hze}$/J, JAX: 007909), p$^{53}$KO (B6.129S2-Trp53$^{tm1Tyj}$/J, JAX:002101), p53FRT (B6;129-Trp53$^{tm10.1Dgk}$/J, JAX:017767), p53flox (FVB.129-Trp53$^{tm1Bm}$/Nci, NCIMR:O1XC2), NF1flox (B6; 129-Nfl$^{tmPar}$/Nci, NCIMR:01XM4), IGF1Rflox (B6;129-Igf1r$^{tm2Arge}$/J, JAX:012251), IGF1flox (B6.129(FVB)-Igf1$^{tm1Dlr}$/J JAX:016831), TG11ML (Igs2$^{tm2(ACTB\text{-}tdTomato,\text{-}EGFP)Zng}$/J, JAX:022977), GT11ML (Igs2$^{tm1(ACTB\text{-}EGFP,\text{-}tdTomato)Zng}$/J, JAX:022976), Gad2-Cre (B6N.Cg-Gad2$^{tm2(cre)Zjh}$/J, JAX:019022), Cx3cr1-CreER (B6.129P2(C)-Cx3cr1$^{tm20.1(cre/ERT2)Jung/J}$, JAX:020940), Omp-hM4Di (B6-Tg(Omp-hM4Di)1Chgliu, this study), Omp-hM3Dq (B6-Tg(Omp-hM3Dq)1Chgliu, this study), Igf1-EGFP (FVB/N-Tg(Igf1-EGFP)1Chgliu, this study), hGFAP-FlpO (B6-Tg(hGFAP-FlpO)1Chgliu, this study), Pcdh21-Cre (FVB/N-Tg(Pcdh21-Cre)1Chgliu, this study).

Mouse Housing Conditions

All mice were routinely housed in individual ventilated cages (3-5 mice per cage) in specific pathogen-free animal care facilities under 12 h light: dark cycle and given ad libitum access to food (Lab Mice Growth and Breeding Diet by Jiangsu Xietong Pharmaceutical Bio-engineering Co., Ltd.) and water. Temperature range from 20° C. to 26° C. and humidity range from 40% to 70%. Corn cob was used as bedding.

Mouse Models

The CKO model: p53KO, NF1flox/p53flox, NF1flox; NG2-CreER/WT; Rosa-tdTomato/WT.

The CKO_Omp-hM4Di model: p53KO, NF1flox/p53flox, NF1flox; NG2-CreER/WT; Rosa-tdTomato/WT; Omp-hM4Di/WT.

The CKO_Omp-hM3Dq model: p53KO, NF1flox/p53flox, NF1flox; NG2-CreER/WT; Rosa-tdTomato/WT; Omp-hM3Dq/WT.

The CKO_IGF1R model: p53KO, NF1flox/p53flox, NF1flox; NG2-CreER/WT; Rosa-tdTomato/WT; IGF1Rflox/IGF1Rflox.

The MADM_p53FRT, NF1Rec_TG; hGFAP-FlpO; Pcdh21-Cre model: TG11ML, p53FRT, NF1-rec/GT11ML; hGFAP-FlpO/WT; Pcdh21-Cre/WT; Rosa-tdTomato/WT.

The MADM_p53FRT, NF1Rec_TG; IGF1flox; hGFAP-FlpO; Pcdh21-Cre model: TG11ML, p53FRT, NF1-rec/GT11ML; IGF1flox/IGF1flox; hGFAP-FlpO/WT; Pcdh21-Cre/WT; Rosa-tdTomato/WT.

The MADM_p53FRT, NF1Rec_TG; hGFAP-FlpO; Cx3cr1-CreER model: TG11ML, p53FRT, NF1-rec/GT11ML; hGFAP-FlpO/WT; Cx3cr1-CreER/WT; Rosa-td-Tomato/WT.

The MADM_p53FRT, NF1Rec_TG; IGF1flox; hGFAP-FlpO; Cx3cr1-CreER model: TG11ML, p53FRT, NF1-rec/GT11ML; IGF1flox/IGF1flox; hGFAP-FlpO/WT; Cx3cr1-CreER/WT; Rosa-tdTomato/WT.

The MADM_p53FRT, NF1Rec_TG; IGF1flox; hGFAP-FlpO; Gad2-Cre model: TG11ML, p53FRT, NF1-rec/GT11ML; IGF1flox/IGF1flox; hGFAP-FlpO/WT; Gad2-Cre/WT; Rosa-tdTomato/WT.

The CKO_Igf1-EGFP model: p53KO, NF1flox/p53flox, NF1flox; NG2-CreER/WT; Rosa-tdTomato/WT; Igf1-EGFP/WT.

The CKO_Omp-hM3Dq_IGF1R model: p53KO, NF1flox/p53flox, NF1flox; NG2-CreER/WT; Rosa-tdTomato/WT; Omp-hM3Dq/WT; IGF1Rflox/IGF1Rflox.

Nomenclatures for the symbols used in mouse genotypes: "," alleles positioned on the same chromosome; ";" alleles positioned on the unrelated chromosomes; "/" separate the pair of homologous chromosomes; "WT" wild type allele; "flox" the floxed allele; "KO" the null allele.

Generation of Conventional and BAC Transgenic Mouse Lines hGFAP-FlpO (B6-Tg(hGFAP-FlpO)1Chgliu) Transgene The linearized DNA segment containing the promoter of human GFAP gene (~5 kb) with the FlpO fragment followed by Woodchuck Hepatitis Virus (WHP) Posttranscriptional Regulatory Element (WPRE) and polyadenylation signal (pA) was purified and adjusted to 1.5 ng/ul for pronuclear injection. The microinjection was performed on the pronucleus of C57/BL6 mouse embryos.

Omp-hM4Di (B6-Tg(Omp-hM4Di)1Chgliu), Omp-hM3Dq (B6-Tg(Omp-hM3Dq)1Chgliu) BAC Transgenes The hM4Di/hM3Dq-internal ribosome entry site (IRES)-mTurquoise2-FRT-Neo (EM7-driven neomycin resistance)-FRT-WPRE-pA segment flanked by 50 bp homology arms was amplified through PCR. The purified DNA fragment was electroporated into the *E. coli* DH10B strain carrying the BAC (BMQ-164P15), which contained the genomic region of the Omp gene. Through the homologous recombination of the Red/ET system, the cassette was inserted into the target site of the BAC DNA. The plasmid expressing Flpe recombinase was then electroporated into the strain to remove the Neo segment in the cassette. The BAC was purified (NucleoBond BAC 100, Macherey-Nagel) and linearized by NotI. The pulsed-field gel electrophoresis was performed to verify the modified BAC DNA. The microinjection was performed on the pronucleus of C57/BL6 mouse embryos at 1.5 ng/ul.

Igf1-EGFP (FVB/N-Tg(Igf1-EGFP)1Chgliu) BAC Transgene

The EGFP-FRT-Neo-FRT-WPRE-pA segment flanked by 50 bp homology arms was amplified through PCR. The purified DNA fragment was electroporated into the *E. coli* DH10B strain carrying the BAC vector (BMQ-250J8), which contained the genomic region of the mouse Igf1 gene. The recombination, purification, and pronuclear injection of the linearized BAC fragment was performed as described above. The mouse embryo background was FVB/N.

Pcdh21-Cre (FVB/N-Tg(Pcdh21-Cre)1Chgliu) BAC Transgene

The Cre-FRT-Neo-FRT-WPRE-pA segment flanked by 50 bp homology arms was amplified through PCR. The purified DNA fragment was electroporated into the *E. coli* DH10B strain carrying the BAC vector (BMQ-313K21) for homologous recombination. The recombination, purification, and pronuclear injection of the linearized BAC fragment was performed as described above.

Genotyping Methods

For genotyping methods, primer sequences, and PCR conditions see below:

Cre:

```
Upper primer: SEQ. ID No. 1:
5-CACCCTGTTACGTATAGCCG-3;

Lower primer: SEQ. ID No. 2:
5-GAGTCATCCTTAGCGCCGTA-3.
```

PCR product: KI band: 300bps.

Rosa2:

```
OIMR9020: SEQ. ID No. 3:
5-AAGGGAGCTGCAGTGGAGTA-3;

OIMR9021: SEQ. ID No. 4:
5-CCGAAAATCTGTGGGAAGTC-3;

OIMR9103: SEQ. ID No. 5:
5-GGCATTAAAGCAGCGTATCC-3;

OIMR9105: SEQ. ID No. 6:
5-CTGTTCCTGTACGGCATGG-3;
```

PCR products: Mut band: 196 bp; WT band: 297 bp.

MADM11_Eif (for all MADM cassettes, including TG11ML and GT11ML):

```
Chr11_CS1: SEQ. ID No. 7:
5-TGGAGGAGGACAAACTGGTCAC-3

Rosa4: SEQ. ID No. 8:
5-TCAATGGGGGGGGTCGTT-3

Chr11_CS2: SEQ. ID No. 9:
5-TTCCCTTTCTGCTTCATCTTGC-3
```

PCR products: Knock-in (KI) band: 230bps; WT band: 350bps.

In MADM mouse model, only KI band can be detected.

P53 KO allele:

```
Neo tail: SEQ. ID No. 10:
5-ACCGCTATCAGGACATAGCGTTGG-3

p53 TJW5: SEQ. ID No. 11:
5-CACAGCGTGGTGGTACCTTATG-3

p53 TJW3: SEQ. ID No. 12:
5-GGTATACTCAGAGCCGGCCTG-3
```

PCR products: KI band: 700bps; WT band: 450bps.

NF1Flox and Recombination (KO) Allele:

```
NF01: SEQ. ID No. 13:
5-ACCTCTCTAGCCTCAGGAATGA-3;

NF02: SEQ. ID No. 14:
5-CTTCAGACTGATTGTTGTACCTGA-3;

NF03: SEQ. ID No. 15:
5-TGATTCCCACTTTGTGGTTCTAAG-3
and

P2: SEQ. ID No. 16:
5-CATCTGCTGCTCTTAGAGGAACA-3
```

PCR products: WT band: 479bps; Flox (Neo) band: 350 bp; KO band: 280 bp.

P53 Flox Allele:

```
T008: SEQ. ID No. 17:
5-CACAAAAACAGGTTAAACCCAG-3;

T009: SEQ. ID No. 18:
5-AGCACATAGGAGGCAGAGAC-3;
```

PCR products: WT band: 288bps; Flox band: 370 bp.

IGF1R-Recox:

```
10451: SEQ. ID No. 19:
5-CTTCCCAGCTTGCTACTCTAGG-3;

10452: SEQ. ID No. 20:
5-CAGGCTTGCAATGAGACATGGG-3;

IGF1R-rec-F:
5-TGAGACGTAGCGAGATTGCTGTA-3;
```

PCR products: WT band: 124bps; Mut band: 220bps; Rec band: 320bps.

GFP:

```
FACS G5': SEQ. ID No. 21:
5-CTTCAAGTCCGCCATGCCCGA-3;

GFP2-Hermie: SEQ. ID No. 22:
5- TCCAGCAGGACCATGTGATCGC-3;
```

PCR products: KI band: 420bps.

IGF1flox:

```
10663: SEQ. ID No. 23:
5-CACTAAGGAGTCTGTATTTGGACC-3;

10664: SEQ. ID No. 24:
5-AAACCACACTGCTCGACATTG-3;

11736: SEQ. ID No. 25:
5-GGCAAATGGAAATCCTATGTCT-3;
```

PCR products: WT band: 275bps; Mut band: 398bps.

P53 FRT:

```
14118: SEQ. ID No. 26:
5-TGCAAGAGAACTGTGCCTAAGA-3;

14119: SEQ. ID No. 27:
5-TTTCTAACAGCAAAGGCAAGC-3;

p53FRT-RecF: SEQ. ID No. 28:
5-CAAGAGAACTGTGCCTAAGAG-3;
```

-continued

```
p53FRT-RecR: SEQ. ID No. 29:
5-ACTCGTGGAACAGAAACAGGCAGA-3;
```

PCR products: WT band: 255bps; Mut band: 393bps.

FlpO:

```
Flip5: SEQ. ID No. 30:
5-AGCCAGTTCGACATCCTGTGCAAGACC-3;

FLip406N:
SEQ. ID No. 31:
5-TCACTTACCTTTGTCGGCCTCCTCGCTGCTCTCG-3;
```

PCR products: KI band: 400bps.

PCR conditions for all PCRs: one cycle at 94° C. for 3 minutes; 32 cycles at 94° C. for 15 seconds; 58° C. for 25 seconds; 72° C. for 45 seconds; and then followed by 72° C. for 5 minutes.

Tissue Preparation

To collect tissues used for cryosection, after anesthesia, mice were briefly perfused with cold PBS and then with 4% paraformaldehyde. The brains were then isolated and post-fixed in 4% PFA for 24 hours and dehydrated in 30% sucrose for 48 hours. Fixed brain tissues were embedded into optimal cutting temperature (O.C.T.) and snap-frozen before preserved in a −80° C. refrigerator. To collect fresh tissues for Western Blot, qPCR, RNA-Seq, whole exome sequencing and cell culture, tissues were acutely collected from deeply anesthetized mice without perfusion.

Cell Culture

Glioma Cell Line Cultures

Mouse glioma cell lines were collected form CKO model in our lab and maintained in complete medium (2 mM L-Glutamine, 1 mM Sodium Pyruvate (Gibco, 11360070), 10 ng/mL d-Biotin (Sigma, B4639), 1× Trace Element B (Cellgro, 25-022-CI), 1×B27 minus vitamin A (Gibco, A3353501), 1× pen/strep (Hydone, SV30010), 50 μg/mL gentamycin (Sigma, 46305) in neurobasal medium (Gibco, #12349015)). Cell lines were authenticated by tdTomato marker when histology analyzing. All cell lines tested negative for mycoplasma contamination.

Primary OB Neuron Cultures

OBs were dissected from P2-3 mouse pups and digested in 10 mL papain solution (1×EBSS (Sigma, E7510), 0.5 mM EDTA, 10 mM HEPES, 26 mM $NaHCO_3$, 22.5 mM D(+)-glucose, 0.16 mg/mL L-cycteine, 20 units/mL papain (Worthington Biochem, LS003126), 250 μg/mL DNase I (Sigma, DN-25) in dd-water) for 30 min at 37° C. Papain solution was discarded and the tissue was triturated with 2 mL Diluted Trypsin Inhibitor Buffer (1×EBSS (Sigma, E7510), 10 mM HEPES, 26 mM $NaHCO_3$, 1× ovomucoid (Worthington Biochem, LS003086), 250 μg/mL DNase I (Sigma, DN-25), 1 mg/mL BSA (equitech-bio, BAH62) in dd-water) by 1 mL pipette and was allowed to settle for 2 min. 1 mL upper cell suspension was carefully collected and additional 1 mL Diluted Trypsin Inhibitor Buffer was add to the tissue. The process was repeated until all Diluted Trypsin Inhibitor Buffer was consumed. Cell suspension was layered over the Standard Trypsin Inhibitor Buffer (1×EBSS (Sigma, E7510), mM HEPES, 26 mM $NaHCO_3$, 1× ovomucoid (Worthington Biochem, LS003086), 10 mg/mL BSA (equitech-bio, BAH62) in dd-water) and centrifuged at 1,200 rpm for 10 min. Supernatant was discarded and cells were resuspended with plating medium (25 mM D(+)-glucose, 2.5 mM $NaHCO_3$, 0.1 mg/mL transferrin (Sigma, T-1147), 10% FBS (serapro, s601s), 2 mM L-glutamine, 0.25 mg/mL insulin (Sigma, I-6634), 1× pen/strep (Hydone, SV30010), 50 μg/mL gentamycin (Sigma, 46305) in neurobasal medium (Gibco, #12349015)) for cell culture. 24 h after initial plating, 80% medium was removed and replaced with OARAC medium (25 mM D(+)-glucose, 2.5 mM $NaHCO_3$, 0.1 mg/mL transferrin (Sigma, T-1147), 5% FBS (serapro, s601s), 0.5 mM L-glutamine, 1× pen/strep (Hydone, SV30010), 50 μg/mL gentamycin (Sigma, 46305), 1×B27 (Gibco, 17504044) in neurobasal medium (Gibco, #12349015)). 48-72 h after initial plating, 50% medium was removed and replaced with 4ARAC medium (25 mM D(+)-glucose, 2.5 mM $NaHCO_3$, 0.1 mg/mL transferrin (Sigma, T-1147), 5% FBS (serapro, s601s), 0.5 mM L-glutamine, 1× pen/strep (Hydone, SV30010), 50 μg/mL gentamycin (Sigma, 46305), 1×B27 (Gibco, 17504044), 4 μM AraC (MKbio, MS0237) in neurobasal medium (Gibco, #12349015)). Glioma cells were plating on OB neurons for co-culture on DIV7 with experiment medium (25 mM D(+)-glucose, 2.5 mM $NaHCO_3$, 0.5 mM L-glutamine, 1× pen/strep (Hydone, SV30010), 50 μg/mL gentamycin (Sigma, 46305), 1×B27 minus insulin (Gibco, A1895601), in neurobasal medium (Gibco, #12349015)). Co-cultured cells were stimulated by 20 ng/mL IGF-1.

Naris Occlusion

Mice were anesthetic before surgery. The silica gel plug (No: 63-625, diameter-1: 0.41 mm, diameter-2: 1.60 mm, length: 15.88 mm), trimmed to 1-1.2 cm and tied with surgical suture (5-0(3/0) 60 cm×15, Hangzhou Huawei medical appliance co. LTD), was carefully plugged into the mouse naris.

Xenografting of Glioma Cells

Mice were anaesthetized and fixed in the stereotaxic apparatus. Skull was exposed and drilled with a small hole (anterior, 4.40 mm; lateral, 0.80 mm; depth, 2 mm). Glioma cells resuspended in complete medium (50,000/μL) were implanted into mice OBs. The mice were dissected 21 days later and analyzed by immunofluorescent staining.

Buried Food Tests

The protocol was adapted from Yang et al.[41] with some modifications. Briefly, two-month-old male transgenic mice and their littermates were used for buried food test. On the first day, Want Want Crunchy Rice Balls were added to the home cages for mice being accustomed to the odor of food. Second day afternoon, all foods were removed for an overnight food deprivation. In the morning of the third day, mice were separated into individual testing cage with about 3 cm depth of clean bedding and acclimated for an hour. After acclimation, the subject mouse was moved to a temporary cage and a rice ball was buried into the bedding about 1.5 cm depth in a random corner. Then the subject was reintroduced into the testing cage. The time latency that the subject found the Rice Balls was recorded. After experiment, the mice were reintroduced to their home cages with Rice Balls. And in afternoon of the fourth day, all foods were removed again. Next morning, before acclimation in individual cage, mice received clozapine (1 mg/kg) or vehicle by intraperitoneal injection. Subsequent process was the same as the third day described above. Endpoint of time latency to find the food is 240s.

Olfactory Activity Characterization 2-4 months male transgenic mice and their WT littermates were used in this set of experiments. We made following efforts to maximally remove the odor from living environment during experiments. First, the empty mouse cage was turned upside down and 200 mL distilled water was added on the tray. Wire fence was provided to avoid mice keeping touch with water directly. At the same time, the cage was ventilated by fresh air (~20 L/min) through rubber tube (LongerPump #18) connecting the compressed air container and the mouse cage.

For Omp-hM4Di mice, the subjects were first received clozapine (1 mg/kg) by intraperitoneal injection and then put into the cage for 120 min. Then, the filter paper with 250 μL odor panel (equivalent undiluted ethyl-acetate, butanal, pentanal, ethyltiglate, propanal, methyl-propionate, and ethyl butyrate) was put into the cage with suspended ventilation for 5 min before taken out. After the odor was blown out with large air flow velocity for 1 min, ventilation was continued (~20 L/min) for 30 min before mice was acutely dissected.

For Omp-hM3Dq mice, subjects were first put into the cage for 90 min. Then, mice received clozapine (1 mg/kg) by intraperitoneal injection, after which ventilation (~20 L/min) was continued for 30 min before mice was acutely dissected.

The Evans Blue Dye Assay

The protocol was adapted from Ludewig et al.[42] with some modifications. Mice were administrated with 200 μL Evans Blue (2%) by i.p injection. After six hours of EB injection, the mice were anaesthetized and then perfused with cold PBS. 100 mg tissue for each sample from multiple organs (as indicated in the FIG. 9*g*) was collected in 500 μL PBS and ground into tissue homogenate. 500 μL formamide was then add to the homogenate before being incubated in the 55° C. for 24 hours. After centrifugation, supernatants were collected for optical density detecting at 620 nm.

Immunofluorescence Analyses

Mouse Routine Tissue Staining

All mouse frozen tissues were cryo-sectioned into 20 μm thickness. For routine staining, the slides were fixed in ice-cold 2% PFA for 15 minutes. After washed in 1×PBS (3 times, 10 minutes each), the slides were briefly rinsed with 1×PBT (0.3% Triton X-100 in 1×PBS) and then incubated with the blocking solution (5% normal donkey serum, 0.3% Triton X-100, 0.1% NaN3 in 1×PBS) for 20 minutes. The slides mounted with primary antibodies were then incubated in the wet box at 4° C. overnight. Next day, the slides were washed in 1×PBT (4 times, 10 minutes each) before incubated with secondary antibodies (diluted in 1×PBT) in foil-wrapped wet box at 4° C. overnight. The third day, the slides were washed in 1×PBT (4 times, 10 minutes each) and DAPI solution (25 ng/ml in 1×PBS, 20 minutes). After washing with 1×PBS for 5 minutes, the slides were mounted with the mounting solution (65% glycerol in 1×PBS) and covered with coverslips.

BrdU Staining

In the first day of staining, the tissue sections were immersed in 1.5M HCl (in 1×PBS) for 30 minutes at 37° C. and washed with 1×PBS (3 times, 10 minutes each) before the incubation of the blocking solution. The staining procedure followed is the same as described above.

Four-Channel Staining

The procedures of the first two days are the same as the routine staining, while donkey anti-host animal-Biotin conjugates (diluted in 1×PBT) were used as secondary antibodies. On the third day, after washing in 1×PBT for 5 minutes, the slides were incubated with Streptavidin Alexa Fluor 405 conjugate (diluted in 1×PBT) at room temperature for 3 hours. Then the slides were washed in 1×PBT (3 times, 10 minutes each) and 1×PBS for 5 minutes before mounted.

Antibody Dilution

Chicken anti-GFP, 1: 500; Goat anti-c-Myc, 1: 200; Goat anti-DsRed, 1: 100; Goat anti-Iba1, 1: 250; Goat anti-PDGFRa, 1: 200; Goat anti-PDGFRP, 1: 200; Mouse anti-APC-CC1, 1: 50; Mouse anti-NeuN, 1: 250; Rabbit anti-c-Fos(9F6), 1: 200; Rabbit anti-CD68, 1: 1000; Rabbit anti-GFAP, 1: 800; Rabbit anti-Iba1, 1: 250; Rabbit anti-Ki67, 1: 500; Rabbit anti-Olfactory Marker Protein (OMP), 1: 500; Rabbit anti-Olig2, 1: 1000; Rabbit anti-TBR2 (abl83991), 1: 1000; Rabbit anti-TBR2 (ab216870), 1: 100; Rabbit anti-Tyrosine Hydroxylase (TH); 1: 500; Rat anti-BrdU, 1: 500; Rat anti-CD34, 1: 200; Alexa Fluor 488 Donkey Anti-Chicken, 1: 250; Alexa Fluor 488 Donkey Anti-Goat, 1: 250; Alexa Fluor 488 Donkey Anti-Mouse, 1: 250; Alexa Fluor 488 Donkey Anti-Rabbit, 1: 250; Alexa Fluor 488 Donkey Anti-Rat, 1: 250; Alexa Fluor 555 Donkey Anti-Goat, 1: 500; Alexa Fluor 647 Donkey Anti-Goat, 1: 250; Alexa Fluor 647 Donkey Anti-Mouse, 1: 250; Alexa Fluor 647 Donkey Anti-Rabbit, 1: 250; Biotin-SP AffiniPure Donkey Anti-Mouse, 1: 200; Cy3 AffiniPure Donkey Anti-Mouse, 1: 500; Cy3 AffiniPure Donkey Anti-Rabbit, 1: 500; DyLight 405 Streptavidin, 1: 100.

Single-Molecule Fluorescent In Situ Hybridization (sm-FISH)

The sample pretreatment protocol was adapted from RNAscope® Universal Pretreatment Kit (ACD, No. 322380). The fresh frozen mouse slices were immediately dried at 60° C. baking oven for 20 minutes after taken out from −80° C. refrigerator, then post-fixed in 4% PFA at 4° C. for 10 minutes. The slices were dehydrated in an EtOH series of 50%, 70%, 90%, 100% for 5 minutes each, followed by dried at room temperature for another 5 minutes. A barrier surrounding the tissue was drawn in the slices. Samples were permeabilized in $H_2O_2$ for minutes and then rinsed in dd$H_2O$. The slices were degraded with Protein Plus instead of Protein IV at 40° C. for 30 minutes, followed by washed in 1×PBS.

Probe signals were detected by FISH using RNAscope® 2.5 HD Detection Kit (RED) (ACD, No. 322350), following the protocol of the kit: 1) add probe, incubate at 40° C. for 2 hours and wash slices twice in Wash Buffer at room temperature for 2 minutes, 2) add AMP1-6 solution at slices successively and wash in Wash Buffer each time after incubate slices in Amp solution, 3) add RED-B with RED-A at room temperature for 10 minutes, 4) wash once in distilled $H_2O$. After hybridized the probes and detected the signals, the slices were washed in PBT for 1 minute. The tissue sections were undergone 20 minutes block incubation at room temperature in blocking solution and incubated with primary antibodies. The following staining steps were the same as described in mouse normal staining.

3D Reconstruction of Tumor Brains

Tumor brains were reconstructed by Neurolucida (MBF Bioscience). The fluorescence images of brain sections were imported to the software. The contour of brain, corpus callosum and tumors were traced by lines with different colors manually and then re-constructed automatically.

Brain Clearing with the PEGASOS Procedure

The protocol was adapted from Jing et al.[40] with some modifications. Immediately following transcardiac perfusion with PBS and 30 mL 4% PFA, brains were fixed in 4% PFA overnight at 4° C. Next, brains were decolourized with 25% EDTP (Sigma-Aldrich, 122262) for 2 days at 37° C. under constant shaking. Serial delipidation was then performed at 37° C. under constant shaking for 6 hours with solutions: 30% tert-Butanol (tB, Sigma-Aldrich; 471712) solution, 50% tB solution and 70% tB solutions. Following delipidation, samples were dehydrated in tB-PEG solution at 37° C. for 2 days. Finally, samples were immersed in the BB-PEG clearing medium for 1 day. Samples could be preserved in the BB-PEG clearing medium at room temperature for storage and imaging. The images were obtained using Nuohai LS18 tiling light sheet microscope. Three-dimensional reconstruction was performed with imaris 9.0 (Bitplane).

Administration of Clozapine, Tamoxifen and BrdU

Clozapine

For characterization of Omp-hM4Di and Omp-hM3Dq mice and acute stage analysis of CKO_Omp-hM3Dq model, 1 mg/kg clozapine was administrated by intraperitoneal injection (i.p.). For analysis of tumor stage of CKO_Omp-hM3Dq model, 1 mg/kg clozapine was administrated by i.p. (twice injection per week, from P150 to P210). For analysis of pre-transforming stage and tumor stage of CKO_Omp-hM4Di model, clozapine was administrated by dissolving in drinking water (final 0.01 mg/mL).

Tamoxifen

Tamoxifen was administrated by intragastric administration at the dose of 200 μg/g body weight on consecutive five days.

BrdU

BrdU was administrated by i.p. at the dose of 50 μg/g body weight on consecutive days as indicated. Mice were dissected at least 1 hour after last injection.

Fluorescence-Activated Cell Sorting (FACS)

Blood was collected by intracardial puncture from anaesthetized mice into heparinized 1 ml syringes. Heparin was used in a range of 30 units/ml. Red blood cells were lysed in ACK lysing buffer (Gibco, A10492) at room temperature for 5 min. Cell suspensions were spun down at 300 g for 5 min. The cell pellet was then washed with Hank's balanced salt solution (HBSS) and spun for 5 min at 300 g. The cells in the pellet (1-2×$10^5$ cells) were used in fluorescence assays. Antibodies used for flow cytometry were directed against the following mouse antigens: Pacific Blue anti-mouse CD45(30-F11), PE anti-mouse Ly-6G(1A8), PerCP/Cyanine5.5 anti-mouse CD11c, FITC anti-mouse CD19 (1D3), APC anti-mouse CD3(17A2), APC/Cyanine7 anti-mouse/human CD11b(M1/70) from Biolegend. Dilution: 1: 200.

Real-Time qPCR

OBs, dissected from fresh mouse brains, were lysed in the TRIzol and stored at −80° C. refrigerator before use. Chloroform was added to samples and the tubes must be thoroughly vortexed. The tubes were centrifuged at 12,000 g for 15 min at 4° C. Upper aqueous phase was removed to a new tube and added with 250 μL isopropyl alcohol. After inverted a few times to mix, the samples were incubated for 10 min and centrifuged at 12,000 g for 10 min at 4° C. Supernatant was discarded by 1 mL pipet tip. After washing the RNA pellet with 950 μL 75% ethanol, the tubes were centrifuged at 7,500 g for 5 min at 4° C. The supernatant was discarded by first 1 mL then 10 μL pipet tips. The RNA pellet was dried and resuspended in RNase free water. Purified RNA was converted to cDNA by First Strand cDNA Synthesis Kit (Thermo Scientific, #K1622) and amplified by SYBR Green Master Mix (Yeasen) at Bio-Rad CFX96. All data were normalized to the Gapdh or Actin reference gene control.

Western Blots

OBs were dissected from fresh mouse brains and lysed in the cold RIPA buffer with the protease inhibitor cocktail and phosphatase inhibitor cocktail tablets. Samples were centrifuged at 12,000 g for 2 min at 4° C. and the supernatant was reserved. The concentration of total protein was normalized by the BCA protein quantification kit (Yeasen). Samples mixed with loading buffer were subjected to the SDS-PAGE for electrophoresis and transferred to PVDF membranes as routine procedure. PVDF membranes were incubated with blocking solution (3% skimmed milk powder in 1×TBST) for 1.5 h and primary antibody solution (diluted in blocking solution) overnight. After washes with TBST (4 times, 15 min each), membranes were incubated with secondary antibodies coupled to horseradish peroxidase (diluted in TBST, peroxidase Donkey Anti-Mouse, 1: 5000; peroxidase Donkey Anti-Rabbit, 1: 5000.) for 1 h. WB bands were detected by using ECL detection kit.

RNA-Seq

RNA-Seq was performed by Shanghai Personal Biotechnology Co., Ltd. The quality of library was confirmed by Agilent 2100 Bioanalyzer. After the validation of library quality, sequencing was performed by Illumina NextSeq500 PE150.

For tissue sequencing, raw data was filtered by removing polluted reads with Cutadapt (Version 1.2.1) and quality control (not lower than Q20). Clean reads were aligned to the reference genome Mus_musculus.GRCm38.dna.primary_assembly.fa (38.86) in Ensembl by Tophat2. Quality of alignment was confirmed though insert length and sequence-based duplication by RseQC. Read counts were calculated by HTSeq 0.6.1p2 (http://www huber.embl.de/users/anders/HTSeq) and normalized by RPKM (Reads Per Kilo bases per Million reads). Differential gene expression analysis was performed by DESeq (Version 1.18.0). The screening threshold was fold change >1.5 and P-value<0.05.

For sequencing of tumor cells from co-cultures, raw data was filtered by removing adapter with Cutadapt (Version 3.4) and quality control (not lower than 25). Clean reads were aligned to the reference genome Mus_musculus.GRCm39.dna.primary_assembly.fa (39.103) from Ensembl by STAR (Version 2.7.9a). Read counts were calculated by featureCounts (Version 2.0.1). The feature was selected as Exon, and only reads with mapping quality score greater than 25 were retained. The batch effect was removed by sva (Version 3.63.0) for samples sequenced at different times. Differential gene expression analysis was performed by DESeq2 (Version 1.28.1). The screening threshold was fold change >1.5 and P-adj<0.05.

Whole Exome Sequencing

Six samples from two CKO mice (one normal brain tissue, two tumor tissues per mouse) were used for Whole Exome Sequencing by Novegene. The insert size of library was tested by Agilent 2100. After the validation of library quality, sequencing was performed by Illumina HiSeq PE150. Raw data was filtered by removing reads with adaptor, reads with more than 10% undetermined bases and read with more than 50% low quality bases. Effective sequencing data was aligned by BWA and Samblaster and processed by Samblaster further. Somatic SNV was processed by muTect. Somatic INDEL was performed by Strelka. Somatic CNV was performed by freec (http://bioinfo-out.curie.fr/projects/freec/).

Quantification Schemes

Quantification of $cFos^+$ Cells

For quantification the distribution of $cFos^+$ cells, GL was separated to eight parts (Lateral, Dorsal-Lateral, Dorsal, Dorsal-Medial, Medial, Ventral-Medial, Ventral, Ventral-Lateral) by same angle (45°). The number of $cFos^+$ cells and corresponding areas were recorded. The density of $cFos^+$ cells was calculated by the number of cells dividing by the corresponding area.

For characterization of hM4Di/hM3Dq mice, the density of $cFos^+$ cells in GL was calculated by the number of cells in the Lateral and Medial GL dividing by the corresponding area (Areal Density). The density of $cFos^+$ cells in ML was calculated by the number of cells in the ML dividing by the length of the ML (Linear Density).

Quantification of Proliferation Rate of Mutant OPCs at the Pre-Transforming Stage BrdU was administrated by consecutive days before mice dissection as indicated. Region of interested (ROI) was circled without supervised of proliferation cells and was circled only by different layers through DAPI. Areas of ROIs were recorded and the number of proliferative mutant cells ($BrdU^+$, $Olig2^+$, $Dsred^+$ cells in the CKO model and $BrdU^+$, $GFP^+$, $cMyc^+$ cells in the MADM model) and mutant cells ($Olig2^+$, $Dsred^+$ cells in the CKO model and $GFP^+$, $cMyc^-$ cells in the MADM model) in ROIs were counted. Density of proliferative mutant OPCs was calculated by the number of proliferative mutant OPCs dividing by the relative areas of ROIs. Density of mutant OPCs was calculated by the number of mutant cells dividing by the relative areas of ROIs. Proliferation rate of mutant OPCs was calculated by density of proliferative mutant cells dividing by density of mutant cells.

Quantification of Tumor Position in the Brain

Brains were serially sectioned and every 14 slices were analyzed. Putative tumor areas (defined by mass of $tdT^+$ cells in the CKO model) were outlined. We analyzed all available tumor mice (N=225) from our CKO models, and confirmed that 221 (98.2%) were fully labeled by tdTomato. Only 4 out of 225 (1.8%) were found to contain non-labeled tumors. tdT-labeling efficiency of tumor cells was confirmed by quantification of $tdT^+$ cell percentage in $Ki67^+$ cells, demonstrating that tdT is a reliable marker for tumors. And only when more than two $tdT^+$, $Ki67^+$ cells were found, the putative tumor area could be defined as a bona tumor. Representative tumor areas were further confirmed by H&E staining as showed in FIG. 5.

Quantification of Tumor Volume in the OB

OBs were serially sectioned and every four slices were analyzed (about 40 slices per OB). Putative tumor areas (defined by mass of $tdT^+$ cells in the CKO model and $GFP^+$, $cMyc^-$ cells in the MADM model) were outlined. Only when more than two $tdT^+$, $Ki67^+$ cells or $GFP^+$, $cMyc^+$, $Ki67^+$ cells were found, the putative tumor area could be defined as a bona tumor. Tumor volume was calculated by the sum of tumor areas in every analyzed slice multiplied by the distance between two adjacent slices (80 μm).

Quantification of Tumor Invasiveness

In the CKO model, tumors were frequently found in the OB as showed, leading to the model that tumors arose in the GL layer then migrated to the EPL and GRL, from the outer to the inner side of the OB. Therefore, we only calculated the invasiveness in the inner side. Core tumor area was defined as the $tdT^+$ cell density more than 70%. Normal area was defined as the $tdT^+$ cell density in the granule cell layer far from the tumor. Tumor invasiveness was defined as the distance between the core tumor area and normal area.

Statistical Methods

Statistical analysis was performed using Graphpad Prism 9. Comparisons of two groups were performed by one-sided t-test. Comparisons of more than two groups were performed using one-way ANOVA with Dunnett's multiple comparison post-hoc test. The number of subjects, samples and the specific statistical test performed are indicated in figure legends. Data is presented as mean±SEM. Differences in means were considered statistically significant at $p<0.05$.

Data Availability

Source data files are provided with this paper. The RNA-seq (accession code GEO ID: GSE160659 and GSE189940) and whole exome sequencing (GSE159427) raw data were uploaded to Gene Expression Omnibus. All other data supporting the findings of this study are available from the corresponding author on request.

What is claimed is:

1. A method for treating or alleviating gliomas in a subject by blocking neuron-derived IGF-1 from neurons in the subject, or blocking an IGF-1 receptor;

wherein the neurons are olfactory neurons, the blocking comprises inhibiting olfactory signaling in the subject, and the inhibiting olfactory signaling in the subject comprises one selected from a group consisting of at least one of depriving olfactory experience or administering to the subject in need thereof a therapeutically effective amount of an agent which inhibits activities of an olfactory neuronal circuit in a brain of the subject, inhibiting IGF-1 from M/T cells, inhibiting IGF-1 from Gad2 positive cells, and inhibiting IGF-1 receptor signaling in pre-cancerous mutant oligodendrocyte precursor cells; and the gliomas are gliomas in a neuronal circuit responsible for sensory inputs of external environmental stimuli.

2. The method for treating or alleviating gliomas in a subject according to claim 1, wherein depriving olfactory experience comprises naris occlusion.

3. The method for treating or alleviating gliomas in a subject according to claim 1, wherein the olfactory neuronal circuit comprise neuronal circuits responsible for the sensory inputs of the external environmental stimuli.

4. The method for treating or alleviating gliomas in a subject according to claim 1, wherein the subject is a human.

5. The method for treating or alleviating gliomas in a subject according to claim 1, wherein inhibiting olfactory signaling in the subject comprises pharmaceutically and genetically inhibiting activities of neurons in olfactory neuronal circuits.

6. The method for treating or alleviating gliomas in a subject according to claim 1, wherein inhibiting IGF-1 from M/T cells and Gad2 positive cells comprises pharmaceutical and genetical inhibiting transcription, translation, transportation, modification and secretion of the IGF-1 and IGF-1 in extracellular space.

7. The method for treating or alleviating gliomas in a subject according to claim 1, wherein inhibiting IGF-1 receptor signaling in pre-cancerous mutant oligodendrocyte precursor cells comprises pharmacologically and genetically inhibiting IGF-1 receptor, PI3K/AKT/mTOR signaling and Ras/Raf/MEK/MAPK pathways.

8. The method for treating or alleviating gliomas in a subject according to claim 5, wherein genetically inhibiting comprises one selected from a group consisting of knocking out genes by CRISPR/Cas9, inhibiting RNAs by shRNA, miRNA, siRNA and ASO and inhibiting proteins by neutralization antibody.

* * * * *

SEQUENCE LISTING

```
Sequence total quantity: 31
SEQ ID NO: 1            moltype = AA  length = 20
FEATURE                 Location/Qualifiers
source                  1..20
                        mol_type = protein
                        organism = synthetic construct
SEQUENCE: 1
CACCCTGTTA CGTATAGCCG                                              20

SEQ ID NO: 2            moltype = AA  length = 20
FEATURE                 Location/Qualifiers
source                  1..20
                        mol_type = protein
                        organism = synthetic construct
SEQUENCE: 2
GAGTCATCCT TAGCGCCGTA                                              20

SEQ ID NO: 3            moltype = AA  length = 20
FEATURE                 Location/Qualifiers
source                  1..20
                        mol_type = protein
                        organism = synthetic construct
SEQUENCE: 3
AAGGGAGCTG CAGTGGAGTA                                              20

SEQ ID NO: 4            moltype = AA  length = 20
FEATURE                 Location/Qualifiers
source                  1..20
                        mol_type = protein
                        organism = synthetic construct
SEQUENCE: 4
CCGAAAATCT GTGGGAAGTC                                              20
```

```
SEQ ID NO: 5            moltype = AA  length = 20
FEATURE                 Location/Qualifiers
source                  1..20
                        mol_type = protein
                        organism = synthetic construct
SEQUENCE: 5
GGCATTAAAG CAGCGTATCC                                                   20

SEQ ID NO: 6            moltype = AA  length = 19
FEATURE                 Location/Qualifiers
source                  1..19
                        mol_type = protein
                        organism = synthetic construct
SEQUENCE: 6
CTGTTCCTGT ACGGCATGG                                                    19

SEQ ID NO: 7            moltype = AA  length = 22
FEATURE                 Location/Qualifiers
source                  1..22
                        mol_type = protein
                        organism = synthetic construct
SEQUENCE: 7
TGGAGGAGGA CAAACTGGTC AC                                                22

SEQ ID NO: 8            moltype = AA  length = 19
FEATURE                 Location/Qualifiers
source                  1..19
                        mol_type = protein
                        organism = synthetic construct
SEQUENCE: 8
TCAATGGGCG GGGGTCGTT                                                    19

SEQ ID NO: 9            moltype = AA  length = 22
FEATURE                 Location/Qualifiers
source                  1..22
                        mol_type = protein
                        organism = synthetic construct
SEQUENCE: 9
TTCCCTTTCT GCTTCATCTT GC                                                22

SEQ ID NO: 10           moltype = AA  length = 24
FEATURE                 Location/Qualifiers
source                  1..24
                        mol_type = protein
                        organism = synthetic construct
SEQUENCE: 10
ACCGCTATCA GGACATAGCG TTGG                                              24

SEQ ID NO: 11           moltype = AA  length = 22
FEATURE                 Location/Qualifiers
source                  1..22
                        mol_type = protein
                        organism = synthetic construct
SEQUENCE: 11
CACAGCGTGG TGGTACCTTA TG                                                22

SEQ ID NO: 12           moltype = AA  length = 21
FEATURE                 Location/Qualifiers
source                  1..21
                        mol_type = protein
                        organism = synthetic construct
SEQUENCE: 12
GGTATACTCA GAGCCGGCCT G                                                 21

SEQ ID NO: 13           moltype = AA  length = 22
FEATURE                 Location/Qualifiers
source                  1..22
                        mol_type = protein
                        organism = synthetic construct
SEQUENCE: 13
ACCTCTCTAG CCTCAGGAAT GA                                                22

SEQ ID NO: 14           moltype = AA  length = 24
FEATURE                 Location/Qualifiers
source                  1..24
                        mol_type = protein
                        organism = synthetic construct
SEQUENCE: 14
CTTCAGACTG ATTGTTGTAC CTGA                                              24
```

```
SEQ ID NO: 15          moltype = AA  length = 24
FEATURE                Location/Qualifiers
source                 1..24
                       mol_type = protein
                       organism = synthetic construct
SEQUENCE: 15
TGATTCCCAC TTTGTGGTTC TAAG                                          24

SEQ ID NO: 16          moltype = AA  length = 23
FEATURE                Location/Qualifiers
source                 1..23
                       mol_type = protein
                       organism = synthetic construct
SEQUENCE: 16
CATCTGCTGC TCTTAGAGGA ACA                                           23

SEQ ID NO: 17          moltype = AA  length = 22
FEATURE                Location/Qualifiers
source                 1..22
                       mol_type = protein
                       organism = synthetic construct
SEQUENCE: 17
CACAAAAACA GGTTAAACCC AG                                            22

SEQ ID NO: 18          moltype = AA  length = 20
FEATURE                Location/Qualifiers
source                 1..20
                       mol_type = protein
                       organism = synthetic construct
SEQUENCE: 18
AGCACATAGG AGGCAGAGAC                                               20

SEQ ID NO: 19          moltype = AA  length = 22
FEATURE                Location/Qualifiers
source                 1..22
                       mol_type = protein
                       organism = synthetic construct
SEQUENCE: 19
CTTCCCAGCT TGCTACTCTA GG                                            22

SEQ ID NO: 20          moltype = AA  length = 22
FEATURE                Location/Qualifiers
source                 1..22
                       mol_type = protein
                       organism = synthetic construct
SEQUENCE: 20
CAGGCTTGCA ATGAGACATG GG                                            22

SEQ ID NO: 21          moltype = AA  length = 21
FEATURE                Location/Qualifiers
source                 1..21
                       mol_type = protein
                       organism = synthetic construct
SEQUENCE: 21
CTTCAAGTCC GCCATGCCCG A                                             21

SEQ ID NO: 22          moltype = AA  length = 22
FEATURE                Location/Qualifiers
source                 1..22
                       mol_type = protein
                       organism = synthetic construct
SEQUENCE: 22
TCCAGCAGGA CCATGTGATC GC                                            22

SEQ ID NO: 23          moltype = AA  length = 24
FEATURE                Location/Qualifiers
source                 1..24
                       mol_type = protein
                       organism = synthetic construct
SEQUENCE: 23
CACTAAGGAG TCTGTATTTG GACC                                          24

SEQ ID NO: 24          moltype = AA  length = 21
FEATURE                Location/Qualifiers
source                 1..21
                       mol_type = protein
                       organism = synthetic construct
SEQUENCE: 24
```

-continued

```
AAACCACACT GCTCGACATT G                                              21

SEQ ID NO: 25          moltype = AA  length = 22
FEATURE                Location/Qualifiers
source                 1..22
                       mol_type = protein
                       organism = synthetic construct
SEQUENCE: 25
GGCAAATGGA AATCCTATGT CT                                             22

SEQ ID NO: 26          moltype = AA  length = 22
FEATURE                Location/Qualifiers
source                 1..22
                       mol_type = protein
                       organism = synthetic construct
SEQUENCE: 26
TGCAAGAGAA CTGTGCCTAA GA                                             22

SEQ ID NO: 27          moltype = AA  length = 21
FEATURE                Location/Qualifiers
source                 1..21
                       mol_type = protein
                       organism = synthetic construct
SEQUENCE: 27
TTTCTAACAG CAAAGGCAAG C                                              21

SEQ ID NO: 28          moltype = AA  length = 21
FEATURE                Location/Qualifiers
source                 1..21
                       mol_type = protein
                       organism = synthetic construct
SEQUENCE: 28
CAAGAGAACT GTGCCTAAGA G                                              21

SEQ ID NO: 29          moltype = AA  length = 24
FEATURE                Location/Qualifiers
source                 1..24
                       mol_type = protein
                       organism = synthetic construct
SEQUENCE: 29
ACTCGTGGAA CAGAAACAGG CAGA                                           24

SEQ ID NO: 30          moltype = AA  length = 27
FEATURE                Location/Qualifiers
source                 1..27
                       mol_type = protein
                       organism = synthetic construct
SEQUENCE: 30
AGCCAGTTCG ACATCCTGTG CAAGACC                                        27

SEQ ID NO: 31          moltype = AA  length = 34
FEATURE                Location/Qualifiers
source                 1..34
                       mol_type = protein
                       organism = synthetic construct
SEQUENCE: 31
TCACTTACCT TTGTCGGCCT CCTCGCTGCT CTCG                                34
```